(12) United States Patent
Sell et al.

(10) Patent No.: US 8,841,431 B2
(45) Date of Patent: Sep. 23, 2014

(54) HEPCIDIN BINDING NUCLEIC ACIDS

(75) Inventors: Simone Sell, Berlin (DE); Frank Morich, Berlin (DE); Christian Maasch, Berlin (DE); Sven Klussmann, Berlin (DE); Nicole Dinse, Berlin (DE); Klaus Buchner, Berlin (DE); Frank Schwobel, Berlin (DE)

(73) Assignee: NOXXON Pharma AG, Berlin (DE)

( * ) Notice: Subject to any disclaimer, the term of this patent is extended or adjusted under 35 U.S.C. 154(b) by 0 days.

(21) Appl. No.: 13/318,144

(22) PCT Filed: Apr. 30, 2010

(86) PCT No.: PCT/EP2010/002659
§ 371 (c)(1), (2), (4) Date: Oct. 30, 2011

(87) PCT Pub. No.: WO2010/124874
PCT Pub. Date: Nov. 4, 2010

(65) Prior Publication Data
US 2012/0053234 A1    Mar. 1, 2012

(30) Foreign Application Priority Data

Apr. 30, 2009 (EP) .................................... 09006028
Jan. 22, 2010 (EP) .................................... 10000635

(51) Int. Cl.
*C07H 21/04* (2006.01)
*A61K 31/00* (2006.01)

(52) U.S. Cl.
CPC ..................................... *A61K 31/00* (2013.01)
USPC ........................................ 536/23.1; 536/24.2

(58) Field of Classification Search
None
See application file for complete search history.

(56) References Cited

U.S. PATENT DOCUMENTS

| | | | |
|---|---|---|---|
| 5,475,096 A * | 12/1995 | Gold et al. | 536/23.1 |
| 5,582,981 A | 12/1996 | Toole et al. | |
| 5,840,867 A | 11/1998 | Toole et al. | |
| 2004/0053310 A1 | 3/2004 | Shi et al. | |
| 2007/0275913 A1 | 11/2007 | Monia et al. | |
| 2008/0213277 A1 * | 9/2008 | Sasu et al. | 424/141.1 |
| 2009/0209478 A1 | 8/2009 | Nakayama et al. | |
| 2011/0112172 A1 | 5/2011 | Purschke et al. | |
| 2012/0053234 A1 | 3/2012 | Sell et al. | |

OTHER PUBLICATIONS

Vyoral et al., Int. J. Biochem. Cell Biol. 37(9)1768-1773, 2005.
Leva et al., "GnRH . . . antagonism," Chem Biol 9, 351-359, 2002.
James, "Aptamers," in Ency Anal Chem, Meyers, ed., John Wiley, Chichester, 2000.
Purschke et al., "A DNA . . . enterotoxin B," NAR 31, 3027-3032, 2003.
De Souza et al., "Novel therapeutics . . . targets," Neuropsychopharm Rev, 1-17, 2008.
Eulberg & Klussmann, ChemBioChem 4, 979-983, 2003.
Vater & Klussmann, Curr Opn Drug Disc Develop 6, 253-261, 2003.

* cited by examiner

*Primary Examiner* — Jennifer McDonald
(74) *Attorney, Agent, or Firm* — MDIP LLC

(57) ABSTRACT

The present invention is related to a nucleic acid capable of binding to hepcidin.

17 Claims, 22 Drawing Sheets

Type A Hepcidin binding nucleic acids

| Name | Sequence: 5'-3' | C (APM) |
|---|---|---|
| 223-C5-001 | GCACUCG UAAAGUAGAG GGAC--CCA----GUCC GGCGUGAUAGUGC CGAGUGC | 14.6nM |
| 223-B5-001 | GCACUUG UAAAGUAGAG GGAC--CCA----GUCC GGCGUGAUAGUGC CGAGUGC | - |
| 223-A5-001 | GCAUUCG UAAAGUAGAG GGAC--CCA----GUCC GGCGUGAUAGUGC CGAGUGC | - |
| 223-A3-001 | GCACUCG UAAAGUAGAG GGAC--CUA----GUCC GGCGUGAUAGUGC CGGGUGC | - |
| 223-F5-001 | GCACUCG UAAAGUAGAG GGAC--CUA----GUCC GGCGUGAUAGUGC CGAGUGC | = |
| 223-G4-001 | GCACUCG UAAAGUAGAG GGAC--UCA----GUCC GGCGUGAUAGUGC CGAGUGC | = |
| 223-A4-001 | GCACUCG UAAAGUAGAG GGAU--ACA----GUCC GGCGUGAUAGUGA CGAGUGC | - |
| 229-C2-001 | CGUGUG UAAAGUAGAG GCAG--CAAU--GUGC GGAGUGUUAGUUGC CAGACG | - |
| 229-B4-001 | CGCCUG UAAAGUAGAG GCAG--CAAU--GUGC GGAGUGUUAGUUGC CAGACG | - |
| 229-E2-001 | CGUGUG UAAAGUAGAG GCAG--GCAU--GUGC GGAGUGUUAGUUGC CAGACG | - |
| 229-B1-001 | CGUGUG UAAAGUAGAG GAG---AAUU----GUC GGCGUGAUAGUGC CACACG | + |
| 229-G1-001 | CGUGUG UAAAGUAGAG CAG---AAUA----GUC GGCGUGAGAGUGC CACACG | = |
| 229-C4-001 | CGUG AAAGUAGAG ACUCCU CGAAUCCAACUA GCGUGAUAGUGC CACG | - |
| 238-A1-001 | AGGCG UAAAGUAGAG GGGC--UGA----GCCC GGCGUGUUAGUGC CGCCU | - |
| 238-E2-001 | AGGCG UAAAGUAGAG GGAC--CUA----GUCC GGCGUGAUAGUGC CGCCU | - |
| 237-A7-001 | CGUGUG UAAAGUAGAG GCAG--AAAU--GUGC GGAGUGUUAGUUC CAGACG | - |
| 236-G2-001 | CGUG AAAGUAGAA AGUUCU CGAAUCCAAUC AGCGUGAUAGUGC CACG | - | terminal nucleotides that may hybridize to each other (bold)

nucleotides that may hybridize to each other (underlined)

*nucleotides that may form a loop structure (italic)*

Box A + Box B: nucleotides which may mainly comprise a Hepcidin-binding motif nt.: nucleotides      variable position C: Results of competition binding assay vs. the reference molecule 223-C5-001 or 229-G1-001 respectively +: better binding affinity than 223-C5-001

=: similar binding affinity as 223-C5-001

-: weaker binding affinity than 223-C5-001

APM: aptamer

Fig. 1

Type A Hepcidin binding nucleic acids

| Name | Sequence: 5'-3' | C (APM) |
|---|---|---|
| 223-C5-001 | GCACUCGUAAAGUAGAGGGAC--CCA----GUCCGGCGUGAUAGUGCCGAGUGC | |
| | | |
| 229-D1-001 | CGUGCUGGCGUGAUAGUGCUCCAG*GUU*CUGGAUAAAGUAGAGCCACG | = |
| 229-E1-001 | CGUGCGAAGGAGUGAUAGUGUUUCUGACUUUCUUCCAGACUCCCACG | n.b. |
| 236-D1-001 | CGUGAAAGUGGAAAUUUGUUGGAAUCAAGCAGGCGAGAUAGUGCCACG | - | terminal nucleotides that may hybridize to each other (bold)

nucleotides that may hybridize to each other (underlined)

*nucleotides that may form a loop structure (italic)*

Box A + Box B: nucleotides which may mainly comprise a Hepcidin -binding motif nt.: nucleotides     variable position

C: Results of competition binding assay vs. the reference molecule 223-C5-001

=: similar binding affinity as 223-C5-001

-: weaker binding affinity than 223-C5-001 n.b.: no binding observed

APM: aptamer

Fig. 2

Type A Hepcidin binding nucleic acids: Derivatives of 223-C5-001

| Name | Sequence: 5'-3' | C (APM) |
|---|---|---|
| 223-C5-001 | GCACUCG UAAAGUAGAG GGAC--CCA----GUCC GGCGUGAUAGUGC CGAGUGC | |
| 223-C5-002 | CACUCG UAAAGUAGAG GCAC--CCA----GUCC GGCGUGAUAGUGC CGAGUG | - |
| 223-C5-006 | CGCGCG UAAAGUAGAG GGAC--CCA----GUCC GGCGUGAUAGUGC CGCGCG | = |
| 223-C5-007 | GCGCCG UAAAGUAGAG GGAC--CCA----GUCC GGCGUGAUAGUGC CGGGC | - |
| 223-C5-008 | GCACUCG UAAAGUAGAG GGA?--CCA----GUCC GGCGUGAUAGUGC CGAGUGC | - | terminal nucleotides that may hybridize to each other (bold)

nucleotides that may hybridize to each other (underlined)

*nucleotides that may form a loop structure (italic)*

Box A + Box B: nucleotides which may mainly comprise a Hepcidin-binding motif nt.: nucleotides    variable position

C: Results of competition binding assay vs. the reference molecules 223-C5-001

=: similar binding affinity as 223-C5-001

-: weaker binding affinity than 223-C5-001

APM: aptamer

Fig. 3

Type A Hepcidin binding nucleic acids:
Derivatives of 229-B1-001

| | | C(APM) | C(SPM) |
|---|---|---|---|
| 229-B1-001 | CGUGUG UAAAGUAGAG GAC---AAUU----GUC GGCGUGAUAGUGC CACACG | 13 nM | |
| 229-B1-002 | GCUGUG UAAAGUAGAG GAC---AAUU----GUC GGCGUGAUAGUGC CACAGC | 16 nM | 41 nM |
| 229-B1-003 | GUGUG UAAAGUAGAG GAC---AAUU----GUC GGCGUGAUAGUGC CACAC | – | |
| 229-B1-004 | GGGUG UAAAGUAGAG GAC---AAUU----GUC GGCGUGAUAGUGC CACGC | – | |
| 229-B1-005 | GCGCG UAAAGUAGAG GAC---AAUU----GUC GGCGUGAUAGUGC CGCGC | – | |
| 229-B1-006 | CGUGUG UAAAGUAGAG GAC---AAUU----GUC GGCGUGAUAGUGC CACAC | – | |
| 229-B1-007 | GGGGUG UAAAGUAGAG GAC---AAUU----GUC GGCGUGAUAGUGC CACGGC | | + |
| 229-B1-008 | GGGGUG UAAAGUAGAG GAC---AAUU----GUC GGCGUGAUAGUGC CACGCC | | 12 nM |
| 229-B1-009 | GCUGCG UAAAGUAGAG GAC---AAUU----GUC GGCGUGAUAGUGC CGCAGC | | = |
| 229-B1-010 | GCUGCG UAAAGUAGAG GAC---AAUU----GUC GGCGUGAUAGUGC CGCAGC | | + |
| 229-B1-011 | GGGGCG UAAAGUAGAG GAC---AAUU----GUC GGCGUGAUAGUGC CGCCGC | | + | terminal nucleotides that may hybridize to each other (bold)

nucleotides that may hybridize to each other (underlined)

*nucleotides that may form a loop structure (italic)*

Box A + Box B: nucleotides which may mainly comprise a Hepcidin-binding motif nt.: nucleotides   variable position

C: Results of competition binding assay vs. the reference molecules 229-B1-001

=: similar binding affinity as 229-B1-001 (C(APM)) or 229-B1-002 (C(SPM)) respectively –: weaker binding affinity than 229-B1-001 (C(APM)) or 229-B1-002 (C(SPM)) respectively +: improved binding affinity in comparison to 229-B1-001 (C(APM)) or 229-B1-002 (C(SPM)) respectively

APM: aptamer

SPM: spiegelmer

Fig. 4

Type B Hepcidin binding nucleic acids

| Name | Sequence: 5'-3' | C(APM) | Biacore |
|---|---|---|---|
| 238-D2-001 | AGCGUGUC GUAUGGGAU-AAGUAAAUGAGGAGUUGGAGGAAG GGUGCGCU | + | |
| 238-D4-001 | AGCGUGUC GUAUGGGAU AAGUAAAUGAGGAGUUGGAGGAAG GGAUGCU | + | 0.51 nM |
| 238-H1-001 | AGUGUGUC GUAUGGGAU-AAGUAAAUGAGGGUUGGAGGAAG GAUGCGCU | + | |
| 238-A2-001 | AGUGUGUC UAUGGGAU-AAGUAAAUGAGGAGUUGGAGGAAA GGAUGCU | + | |
| 238-G2-001 | AGCGUGCC GAUGGGAU-AAGUAAAUGAGGAGUUGGAGGAAG GGUGCGCU | + | |
| 238-G4-001 | AGCGUGCC GUAUGGGAU-AAGUAAAUGAGGAGUGGAGGAAG GGUACGCU | - | -/n.b. |
| 238-G3-001 | AGCGCGCC GUAUGGGAG-AAGUAAAUGAGGAGUUGGAGGAAG GGCGCGCU | + | | terminal nucleotides that may hybridize to each other (bold)

[central stretch] nucleotides which may mainly comprise a Hepcidin-binding motif nt.: nucleotides        variable position

C: Results of competition binding assay vs. the reference molecules 229-B1-001

Biacore: Results of Biacore measurement of Spiegelmers binding to immobilized Hepcidin

+: better binding affinity than 229-B1-001

-: weaker binding affinity than 229-B1-001

APM: aptamer n.b.: no binding observed

Fig. 5

Type B Hepcidin binding nucleic acids: Derivatives of 238-D4-001

| Name | Sequence: 5'-3' | C(APM) | C(SPM) | Biacore |
|---|---|---|---|---|
| 238-D4-001 | AGCGUGUC GUAUGGGAUUAAGUAAAUGAGGAGUUGGAGGAAG GGCAUGCU | 4.2 nM | 3 nM | 0.51 nM |
| 238-D4-002 | GCGCGC GUAUGGGAUUAAGUAAAUGAGGAGUUGGAGGAAG GCGCGC | | 3,9 nM | 0.59 nM |
| 238-D4-003 | GCGCGC GUAUGGGAU-AAGUAAAUGAGGAGUUGGAGGAAG GCGCGC | | - | |
| 238-D4-004 | GCGC GUAUGGGAUUAAGUAAAUGAGGAGUUGGAGGAAG GCGC | | = | |
| 238-D4-005 | GCGC GUAUGGGAU-AAGUAAAUGAGGAGUUGGAGGAAG GCGC | | - | |
| 238-D4-006 | GGUGUC GUAUGGGAUUAAGUAAAUGAGCAGUUGGAGGAAC GGCAUC | | 5,3 nM | 0.48 nM |
| 238-D4-007 | GGUGUC GUAUGGGAU-AAGUAAAUGAGGAGUUGGAGGAAG GGCAUC | | | - |
| 238-D4-008 | GGGC GUAUGGGAUUAAGUAAAUGAGCAGUUGGAGGAAG GGCGC | | 2,6 nM | 0.48 nM |
| 238-D4-009 | GGGC GUAUGGGAU-AAGUAAAUGAGGAGUUGGAGGAAG GGCGC | | - | - |
| 238-D4-010 | GGCGC GUAUGGGAUUAAGUAAAUGAGCAGUUGGAGGAAG GGCGCC | | | - |
| 238-D4-011 | GGCGC GUAUGGGAU-AAGUAAAUGAGCAGUUGGAGGAAG GGCGCC | | 5,5 nM | - |
| 238-D4-012 | GGCGUC GUAUGGGAUUAAGUAAAUGAGGAGUUGGAGGAAG GGCGCC | | = | = |
| 238-D4-013 | GGCGUC GUAUGGGAU-AAGUAAAUGAGGAGUUGGAGGAAG GGCGCC | | - | | terminal nucleotides that may hybridize to each other (bold)

central stretch nucleotides which may mainly comprise a Hepcidin-binding motif nt.: nucleotides        variable position

C: Results of competition binding assay vs. the reference molecules 238-D4-001

Biacore: Results of Biacore measurement of Spiegelmers binding to immobilized Hepcidin =: similar binding affinity as 238-D4-001

-: weaker binding affinity than 238-D4-001

APM: aptamer

SPM: spiegelmer

Fig. 6

Type C Hepcidin binding nucleic acids

| Name | Sequence: 5'-3' | C(APM) | Biacore |
|---|---|---|---|
| 238-C4-001 | AGGCUCG GACAGCCGGGGGACACCAUAUACAGACUACGAUA CGGGCCU | + | 0.89 nM |
| 238-E3-001 | AGGCUCG GACGGCCGGGGGACACCAUAUACAGACUACGAUA CGGGCCU | + | |
| 238-F2-001 | AGGCGCG GACAGCCGGGGGACACCAUAUACAGACUACGAUA CGGGCCU | + | |
| 238-A4-001 | AGGCUUGGGCGGCCGGGGGACACCAUAUACAGACUACGAUA CGAGCCU | + | |
| 238-E1-001 | AGACUUGGGCCAGCCGGGGGACACCAUAUACAGACUACGAUA CGAGUCU | + | | terminal nucleotides that may hybridize to each other (bold)

central stretch nucleotides which may mainly comprise a Hepcidin-binding motif nt.: nucleotides          variable position

C: Results of competition binding assay vs. the reference molecules 229-B1-001

Biacore: Results of Biacore measurement of Spiegelmers binding to immobilized Hepcidin

+: better binding affinity than 229-B1-001

APM: aptamer

Fig. 7

SEQUENCE LISTING

```
<160> NUMBER OF SEQ ID NOS: 218

<210> SEQ ID NO 1
<211> LENGTH: 25
<212> TYPE: PRT
<213> ORGANISM: Homo sapiens

<400> SEQUENCE: 1

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 2
<211> LENGTH: 25
<212> TYPE: PRT
<213> ORGANISM: Macaca mulatta

<400> SEQUENCE: 2

Asp Thr His Phe Pro Ile Cys Ile Phe Cys Cys Gly Cys Cys His Arg
1               5                   10                  15
```

Ser Lys Cys Gly Met Cys Cys Lys Thr
            20                  25

<210> SEQ ID NO 3
<211> LENGTH: 25
<212> TYPE: PRT
<213> ORGANISM: Macaca fascicularis

<400> SEQUENCE: 3

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 4
<211> LENGTH: 25
<212> TYPE: PRT
<213> ORGANISM: Sus scrofa

<400> SEQUENCE: 4

Asp Thr His Phe Pro Ile Cys Ile Phe Cys Cys Gly Cys Cys Arg Lys
1               5                   10                  15

Ala Ile Cys Gly Met Cys Cys Lys Thr
            20                  25

<210> SEQ ID NO 5
<211> LENGTH: 25
<212> TYPE: PRT
<213> ORGANISM: Mus musculus

<400> SEQUENCE: 5

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25

<210> SEQ ID NO 6
<211> LENGTH: 25
<212> TYPE: PRT
<213> ORGANISM: Rattus norvegicus

<400> SEQUENCE: 6

Asp Thr Asn Phe Pro Ile Cys Leu Phe Cys Cys Lys Cys Cys Lys Asn
1               5                   10                  15

Ser Ser Cys Gly Leu Cys Cys Ile Thr
            20                  25

<210> SEQ ID NO 7
<211> LENGTH: 25
<212> TYPE: PRT
<213> ORGANISM: Homo sapiens

<400> SEQUENCE: 7

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 8
<211> LENGTH: 20
<212> TYPE: PRT
<213> ORGANISM: Homo sapiens

```
<400> SEQUENCE: 8

Ile Cys Ile Phe Cys Cys Gly Cys Cys His Arg Ser Lys Cys Gly Met
1               5                   10                  15

Cys Cys Lys Thr
            20

<210> SEQ ID NO 9
<211> LENGTH: 22
<212> TYPE: PRT
<213> ORGANISM: Homo sapiens

<400> SEQUENCE: 9

Phe Pro Ile Cys Ile Phe Cys Cys Gly Cys Cys His Arg Ser Lys Cys
1               5                   10                  15

Gly Met Cys Cys Lys Thr
            20

<210> SEQ ID NO 10
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 10
gcacucguaa aguagaggga cccaguccgg cgugauagug ccgagugc                 48

<210> SEQ ID NO 11
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 11
gcacuuguaa aguagaggga cccaguccgg cgugauagug ccgagugc                 48

<210> SEQ ID NO 12
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 12
gcauucguaa aguagaggga cccaguccgg cgugauagug ccgagugc                 48

<210> SEQ ID NO 13
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 13
```

```
gcacucguaa aguagaggga ccuaguccgg cgugauagug ccggguc            48
```

<210> SEQ ID NO 14
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 14

```
gcacucguaa aguagaggga ccuaguccgg cgugauagug ccgagugc           48
```

<210> SEQ ID NO 15
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 15

```
gcacucguaa aguagaggga cucaguccgg cgugauagug ccgagugc           48
```

<210> SEQ ID NO 16
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 16

```
gcacucguaa aguagaggga uacaguccgg cgugauagug acgagugc           48
```

<210> SEQ ID NO 17
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 17

```
cguguguaaa guagaggcag guaaucugcg gaguguuagu uccacacg           48
```

<210> SEQ ID NO 18
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 18

```
cgcguguaaa guagaggcag guaaucugcg gaguguuagu uccacacg           48
```

```
<210> SEQ ID NO 19
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 19
cguguguaaa guagaggcag gcaaucugcg gaguguuagu uccacacg                48

<210> SEQ ID NO 20
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 20
cguguguaaa guagaggaca auugucggcg ugauagugcc acacg                   45

<210> SEQ ID NO 21
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 21
gcuguguaaa guagaggaca auugucggcg ugauagugcc acagc                   45

<210> SEQ ID NO 22
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 22
cguguguaaa guagaggaca auagucggcg ugagagugcc acacg                   45

<210> SEQ ID NO 23
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 23
cgugaaaagu agaaacuugu cgaaagcaag uagcgugaua gugccacg                48

<210> SEQ ID NO 24
<211> LENGTH: 48
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 24
cgugcuggcg ugauagugcu ccagguucug gauaaaguag agagcacg                    48

<210> SEQ ID NO 25
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 25
cgugcgaagg agugauaagu guuucugacu uucuuccaga cucccacg                    48

<210> SEQ ID NO 26
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 26
cacucguaaa guagagggac ccaguccggc gugauagugc cgagug                      46

<210> SEQ ID NO 27
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 27
cgcgcguaaa guagagggac ccaguccggc gugauagugc cgcgcg                      46

<210> SEQ ID NO 28
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 28
gcgcguaaag uagagggacc caguccggcg ugauagugcc gcgc                        44

<210> SEQ ID NO 29
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: L-RNA

<400> SEQUENCE: 29
gcacucguaa aguagaggga cccaguccgg cgugauagug ccgagugc            48

<210> SEQ ID NO 30
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 30
gcacuuguaa aguagaggga cccaguccgg cgugauagug ccgagugc            48

<210> SEQ ID NO 31
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 31
gcauucguaa aguagaggga cccaguccgg cgugauagug ccgagugc            48

<210> SEQ ID NO 32
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 32
gcacucguaa aguagaggga ccuaguccgg cgugauagug ccggguge            48

<210> SEQ ID NO 33
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 33
gcacucguaa aguagaggga ccuaguccgg cgugauagug ccgagugc            48

<210> SEQ ID NO 34
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 34
```

```
gcacucguaa aguagaggga cucaguccgg cgugauagug ccgagugc         48
```

<210> SEQ ID NO 35
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 35

```
gcacucguaa aguagaggga uacaguccgg cgugauagug acgagugc         48
```

<210> SEQ ID NO 36
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 36

```
cguguguaaa guagaggcag guaaucugcg gaguguuagu uccacacg         48
```

<210> SEQ ID NO 37
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 37

```
cgcguguaaa guagaggcag guaaucugcg gaguguuagu uccacacg         48
```

<210> SEQ ID NO 38
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 38

```
cguguguaaa guagaggcag gcaaucugcg gaguguuagu uccacacg         48
```

<210> SEQ ID NO 39
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 39

```
cguguguaaa guagaggaca auugucggcg ugauagugcc acacg            45
```

<210> SEQ ID NO 40

```
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 40
gcuguguaaa guagaggaca auugucggcg ugauagugcc acagc            45

<210> SEQ ID NO 41
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 41
cguguguaaa guagaggaca auagucggcg ugagagugcc acacg            45

<210> SEQ ID NO 42
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 42
cgugaaaagu agaaacuugu cgaaagcaag uagcgugaua gugccacg         48

<210> SEQ ID NO 43
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 43
cgugcuggcg ugauagugcu ccagguucug gauaaaguag agagcacg         48

<210> SEQ ID NO 44
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 44
cgugcgaagg agugauaagu guuucugacu uucuuccaga cucccacg         48

<210> SEQ ID NO 45
<211> LENGTH: 46
<212> TYPE: RNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: L-RNA

<400> SEQUENCE: 45
cacucguaaa guagagggac ccaguccggc gugauagugc cgagug                    46

<210> SEQ ID NO 46
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 46
cgcgcguaaa guagagggac ccaguccggc gugauagugc cgcgcg                    46

<210> SEQ ID NO 47
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 47
gcgcguaaag uagagggacc caguccggcg ugauagugcc gcgc                      44

<210> SEQ ID NO 48
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 48
gcacucguaa aguagaggga cccaguccgg cgugauagug ccgagugc                  48

<210> SEQ ID NO 49
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 49
aggcguaaag uagaggggcu gagcccggcg uguuagugcc gccu                      44

<210> SEQ ID NO 50
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

```
<400> SEQUENCE: 50
aggcguaaag uagagggacg uaguccggcg ugauagugcc gccu              44

<210> SEQ ID NO 51
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 51
cguguguaaa guagaggcag auaaucugcg gaguguuagu uccacacg          48

<210> SEQ ID NO 52
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 52
cgugaaaagu agaaacuugu cgaaagcaag cagcgugaua gugccacg          48

<210> SEQ ID NO 53
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 53
cgugaaaagu ugaaauuugu uggaaucaag cagggauaua gugccacg          48

<210> SEQ ID NO 54
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 54
agcgugucgu augggauaag uaaaugagga guuggaggaa gggugcgcu         49

<210> SEQ ID NO 55
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 55
agcgugucgu augggauuaa guaaaugagg aguuggagga aggcaugcu         50
```

```
<210> SEQ ID NO 56
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 56
agugugucgu augggauaag uaaaugaggg guuggaggaa ggaugcgcu            49

<210> SEQ ID NO 57
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 57
agugugucau augggauaag uaaaugagga guuggaggaa aggcaugcu            49

<210> SEQ ID NO 58
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 58
agcgugccgg augggauaag uaaaugagga guuggaggaa gggugcgcu            49

<210> SEQ ID NO 59
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 59
agcgugccgu augggauaag uaaaugagga guaggaggaa ggguacgcu            49

<210> SEQ ID NO 60
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 60
agcgcgccgu auggagaaag uaaaugagga guuggaggaa gggcgcgcu            49

<210> SEQ ID NO 61
<211> LENGTH: 48
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 61
aggcucggac agccggggga caccauauac agacuacgau acgggccu                48

<210> SEQ ID NO 62
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 62
aggcucggac ggccggggga caccauauac agacuacuau acgggccu                48

<210> SEQ ID NO 63
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 63
aggcccggac agccggggga caccauauac agacuacuau acgggccu                48

<210> SEQ ID NO 64
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 64
aggcuugggc ggccggggga caccauauac agacuacuau acgagccu                48

<210> SEQ ID NO 65
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 65
agacuugggc agccggggga caccauauac agacuacgau acgagucu                48

<210> SEQ ID NO 66
<211> LENGTH: 49
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: D-RNA

<400> SEQUENCE: 66
cgggcgccau agaccguuau uaagcacugu aacuaccgaa ccgcgcccg        49

<210> SEQ ID NO 67
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 67
cgggcgccau agaccguuaa cuacauaacu accgaaccgu gcccg             45

<210> SEQ ID NO 68
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 68
cgggcgcuac cgaacccacu aaaaccagug cauagaccgc gcccg             45

<210> SEQ ID NO 69
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 69
cgggcgcuac cgaaccguca cgaagaccau agaccgcgcc g                 41

<210> SEQ ID NO 70
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 70
cgagcgcaac cgaaccucua cccagacaua gaccgcgccc g                 41

<210> SEQ ID NO 71
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA
```

<400> SEQUENCE: 71
gcacucguaa aguagaggga ccaguccggc gugauagugc cgagugc        47

<210> SEQ ID NO 72
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 72
guguguaaag uagaggacaa uugucggcgu gauagugcca cac        43

<210> SEQ ID NO 73
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 73
gcguguaaag uagaggacaa uugucggcgu gauagugcca cgc        43

<210> SEQ ID NO 74
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 74
gcgcguaaag uagaggacaa uugucggcgu gauagugccg cgc        43

<210> SEQ ID NO 75
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 75
cguguguaaa guagaggaca auugucggcg ugauagugcc acac        44

<210> SEQ ID NO 76
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 76
gccguguaaa guagaggaca auugucggcg ugauagugcc acggc        45

```
<210> SEQ ID NO 77
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 77
gcgguguaaa guagaggaca auugucggcg ugauagugcc accgc               45

<210> SEQ ID NO 78
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 78
gcugcguaaa guagaggaca auugucggcg ugauagugcc gcagc               45

<210> SEQ ID NO 79
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 79
gcuggguaaa guagaggaca auugucggcg ugauagugcc ccagc               45

<210> SEQ ID NO 80
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 80
gcggcguaaa guagaggaca auugucggcg ugauagugcc gccgc               45

<210> SEQ ID NO 81
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 81
gcgcgcguau gggauuaagu aaaugaggag uuggaggaag gcgcgc              46

<210> SEQ ID NO 82
<211> LENGTH: 45
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 82
gcgcgcguau gggauaagua aaugaggagu uggaggaagg cgcgc                45

<210> SEQ ID NO 83
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 83
ggcgcguaug ggauuaagua aaugaggagu uggaggaagg cgcc                 44

<210> SEQ ID NO 84
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 84
ggcgcguaug ggauaaguaa augaggaguu ggaggaaggc gcc                  43

<210> SEQ ID NO 85
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 85
ggugucguau gggauuaagu aaaugaggag uuggaggaag gcauc                46

<210> SEQ ID NO 86
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 86
ggugucguau gggauaagua aaugaggagu uggaggaagg gcauc                45

<210> SEQ ID NO 87
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: D-RNA

<400> SEQUENCE: 87
gcgccguaug ggauuaagua aaugaggagu uggaggaagg cgcc            44

<210> SEQ ID NO 88
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 88
gcgccguaug ggauaaguaa augaggaguu ggaggaaggg cgc             43

<210> SEQ ID NO 89
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 89
ggcgccguau gggauuaagu aaaugaggag uuggaggaag gcgcc           46

<210> SEQ ID NO 90
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 90
ggcgccguau gggauaagua aaugaggagu uggaggaagg cgcc            45

<210> SEQ ID NO 91
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 91
ggcgucguau gggauuaagu aaaugaggag uuggaggaag gcgcc           46

<210> SEQ ID NO 92
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 92
```
ggcgucguau gggauaagua aaugaggagu uggaggaagg cgcc         45

<210> SEQ ID NO 93
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 93
ggcucggaca gccgggggac accauauaca gacuacgaua cgggcc       46

<210> SEQ ID NO 94
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 94
gcucggacag ccgggggaca ccauauacag acuacgauac gggc         44

<210> SEQ ID NO 95
<211> LENGTH: 42
<212> TYPE: RNA
<213> ORGANISM: Artificial Sequence
<220> FEATURE:
<223> OTHER INFORMATION: Description of Artificial Sequence: Synthetic
      oligoneotide
<220> FEATURE:
<223> OTHER INFORMATION: D-RNA

<400> SEQUENCE: 95
cucggacagc cgggggacac cauauacaga cuacgauacg gg           42

<210> SEQ ID NO 96
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 96
gcccggacag ccgggggaca ccauauacag acuacgauac gggc         44

<210> SEQ ID NO 97
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 97
ggccggacag ccgggggaca ccauauacag acuacgauac ggcc         44

```
<210> SEQ ID NO 98
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 98
gcggagacag ccgggggaca ccauauacag acuacgauau ccgu                    44

<210> SEQ ID NO 99
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 99
aggcugacag ccgggggaca ccauauacag acuacgauag gccu                    44

<210> SEQ ID NO 100
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 100
ggccugacag ccgggggaca ccauauacag acuacgauaa ggcu                    44

<210> SEQ ID NO 101
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 101
gcgcggacag ccgggggaca ccauauacag acuacgauac gcgc                    44

<210> SEQ ID NO 102
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 102
gccggacagc cgggggacac cauauacaga cuacgauacg gc                      42

<210> SEQ ID NO 103
<211> LENGTH: 42
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 103
ggcggacagc cggggacac cauauacaga cuacgauacg cc                          42

<210> SEQ ID NO 104
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 104
ggccgacagc cggggacac cauauacaga cuacgauagg cc                          42

<210> SEQ ID NO 105
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 105
gcgcgacagc cggggacac cauauacaga cuacgauagc gc                          42

<210> SEQ ID NO 106
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 106
ggccggacag ccggaggaca ccauauacag acuacgauac ggcc                       44

<210> SEQ ID NO 107
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: D-RNA

<400> SEQUENCE: 107
ggccggacag ccggcggaca ccauauacag acuacgauac ggcc                       44

<210> SEQ ID NO 108
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: D-RNA

<400> SEQUENCE: 108
ggccggacag ccgggaggac accauauaca gacuacgaua cggcc        45

<210> SEQ ID NO 109
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 109
uccagguucu gga        13

<210> SEQ ID NO 110
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 110
aggcguaaag uagaggggcu gagcccggcg uguuagugcc gccu        44

<210> SEQ ID NO 111
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 111
aggcguaaag uagagggacg uaguccggcg ugauagugcc gccu        44

<210> SEQ ID NO 112
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 112
cguguguaaa guagaggcag auaaucugcg gaguguuagu uccacacg        48

<210> SEQ ID NO 113
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 113
cgugaaaagu agaaacuugu cgaaagcaag cagcgugaua gugccacg       48

<210> SEQ ID NO 114
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 114
cgugaaaagu ugaaauuugu uggaaucaag cagggauaua gugccacg       48

<210> SEQ ID NO 115
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 115
agcgugucgu augggauaag uaaaugagga guuggaggaa gggugcgcu      49

<210> SEQ ID NO 116
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 116
agcgugucgu augggauuaa guaaaugagg aguuggagga agggcaugcu     50

<210> SEQ ID NO 117
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 117
agugugucgu augggauaag uaaaugaggg guuggaggaa ggaugcgcu      49

<210> SEQ ID NO 118
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 118
agugugucau augggauaag uaaaugagga guuggaggaa aggcaugcu      49

<210> SEQ ID NO 119

```
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 119
agcgugccgg augggauaag uaaaugagga guuggaggaa gggugcgcu            49

<210> SEQ ID NO 120
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 120
agcgugccgu augggauaag uaaaugagga guaggaggaa ggguacgcu            49

<210> SEQ ID NO 121
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 121
agcgcgccgu augggagaag uaaaugagga guuggaggaa gggcgcgcu            49

<210> SEQ ID NO 122
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 122
aggcucggac agccggggga caccauauac agacuacgau acgggccu             48

<210> SEQ ID NO 123
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 123
aggcucggac ggccggggga caccauauac agacuacuau acgggccu             48

<210> SEQ ID NO 124
<211> LENGTH: 48
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: L-RNA

<400> SEQUENCE: 124
aggcccggac agccggggga caccauauac agacuacuau acgggccu                 48

<210> SEQ ID NO 125
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 125
aggcuugggc ggccggggga caccauauac agacuacuau acgagccu                 48

<210> SEQ ID NO 126
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 126
agacuugggc agccggggga caccauauac agacuacgau acgagucu                 48

<210> SEQ ID NO 127
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 127
cgggcgccau agaccguuau uaagcacugu aacuaccgaa ccgcgcccg                49

<210> SEQ ID NO 128
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 128
cgggcgccau agaccguuaa cuacauaacu accgaaccgu gcccg                    45

<210> SEQ ID NO 129
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA
```

<400> SEQUENCE: 129
cgggcgcuac cgaacccacu aaaaccagug cauagaccgc gcccg        45

<210> SEQ ID NO 130
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 130
cgggcgcuac cgaaccguca cgaagaccau agaccgcgcc g        41

<210> SEQ ID NO 131
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 131
cgagcgcaac cgaaccucua cccagacaua gaccgcgccc g        41

<210> SEQ ID NO 132
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 132
gcacucguaa aguagaggga ccaguccggc gugauagugc cgagugc        47

<210> SEQ ID NO 133
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 133
guguguaaag uagaggacaa uugucggcgu gauagugcca cac        43

<210> SEQ ID NO 134
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 134
gcguguaaag uagaggacaa uugucggcgu gauagugcca cgc        43

<210> SEQ ID NO 135
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 135
gcgcguaaag uagaggacaa uugucggcgu gauagugccg cgc          43

<210> SEQ ID NO 136
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 136
cguguguaaa guagaggaca auugucggcg ugauagugcc acac         44

<210> SEQ ID NO 137
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 137
gccguguaaa guagaggaca auugucggcg ugauagugcc acggc        45

<210> SEQ ID NO 138
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 138
gcgguguaaa guagaggaca auugucggcg ugauagugcc accgc        45

<210> SEQ ID NO 139
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 139
gcugcguaaa guagaggaca auugucggcg ugauagugcc gcagc        45

<210> SEQ ID NO 140
<211> LENGTH: 45

-continued

<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 140
gcuggguaaa guagaggaca auugucggcg ugauagugcc ccagc          45

<210> SEQ ID NO 141
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 141
gcggcguaaa guagaggaca auugucggcg ugauagugcc gccgc          45

<210> SEQ ID NO 142
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 142
gcgcgcguau gggauuaagu aaaugaggag uuggaggaag gcgcgc         46

<210> SEQ ID NO 143
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 143
gcgcgcguau gggauaagua aaugaggagu uggaggaagg cgcgc          45

<210> SEQ ID NO 144
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 144
ggcgcguaug ggauuaagua aaugaggagu uggaggaagg cgcc           44

<210> SEQ ID NO 145
<211> LENGTH: 43
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: L-RNA

<400> SEQUENCE: 145
ggcgcguaug ggauaaguaa augaggaguu ggaggaaggc gcc                43

<210> SEQ ID NO 146
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 146
ggugucguau gggauuaagu aaaugaggag uuggaggaag ggcauc             46

<210> SEQ ID NO 147
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 147
ggugucguau gggauaagua aaugaggagu uggaggaagg gcauc              45

<210> SEQ ID NO 148
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 148
gcgccguaug ggauuaagua aaugaggagu uggaggaagg gcgc               44

<210> SEQ ID NO 149
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 149
gcgccguaug ggauaaguaa augaggaguu ggaggaaggg cgc                43

<210> SEQ ID NO 150
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

```
<400> SEQUENCE: 150
ggcgccguau gggauuaagu aaaugaggag uuggaggaag ggcgcc                    46

<210> SEQ ID NO 151
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 151
ggcgccguau gggauaagua aaugaggagu uggaggaagg cgcc                     45

<210> SEQ ID NO 152
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 152
ggcgucguau gggauuaagu aaaugaggag uuggaggaag ggcgcc                    46

<210> SEQ ID NO 153
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 153
ggcgucguau gggauaagua aaugaggagu uggaggaagg cgcc                     45

<210> SEQ ID NO 154
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 154
ggcucggaca gccgggggac accauauaca gacuacgaua cgggcc                    46

<210> SEQ ID NO 155
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 155
gcucggacag ccgggggaca ccauauacag acuacgauac gggc                     44
```

<210> SEQ ID NO 156
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 156
cucggacagc cggggggacac cauauacaga cuacgauacg gg                            42

<210> SEQ ID NO 157
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 157
gacaauaguc                                                                10

<210> SEQ ID NO 158
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 158
gcccggacag ccgggggaca ccauauacag acuacgauac gggc                          44

<210> SEQ ID NO 159
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 159
ggccggacag ccgggggaca ccauauacag acuacgauac ggcc                          44

<210> SEQ ID NO 160
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 160
gcggagacag ccgggggaca ccauauacag acuacgauau ccgu                          44

<210> SEQ ID NO 161
<211> LENGTH: 44
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 161
aggcugacag ccgggggaca ccauauacag acuacgauag gccu                    44

<210> SEQ ID NO 162
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 162
ggccugacag ccgggggaca ccauauacag acuacgauaa ggcu                    44

<210> SEQ ID NO 163
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 163
gcgcggacag ccgggggaca ccauauacag acuacgauac gcgc                    44

<210> SEQ ID NO 164
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 164
gccggacagc cggggacac cauauacaga cuacgauacg gc                       42

<210> SEQ ID NO 165
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 165
ggcggacagc cggggacac cauauacaga cuacgauacg cc                       42

<210> SEQ ID NO 166
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: L-RNA

<400> SEQUENCE: 166
ggccgacagc cggggggacac cauauacaga cuacgauagg cc        42

<210> SEQ ID NO 167
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 167
gcgcgacagc cggggggacac cauauacaga cuacgauagc gc        42

<210> SEQ ID NO 168
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 168
ggccggacag ccggaggaca ccauauacag acuacgauac ggcc       44

<210> SEQ ID NO 169
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 169
ggccggacag ccggcggaca ccauauacag acuacgauac ggcc       44

<210> SEQ ID NO 170
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 170
ggccggacag ccgggaggac accauauaca gacuacgaua cggcc      45

<210> SEQ ID NO 171
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 171
```
gcuguguaaa guagaggaca auugucggcg ugauagugcc acagc     45

<210> SEQ ID NO 172
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 172
gcacucguaa aguagaggga cccaguccgg cgugauagug ccgagugc     48

<210> SEQ ID NO 173
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 173
gcuguguaaa guagaggaca auugucggcg ugauagugcc acagc     45

<210> SEQ ID NO 174
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 174
ggccggacag ccgggggaca ccauauacag acuacgauac ggcc     44

<210> SEQ ID NO 175
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 175
gcgcgcguau gggauuaagu aaaugaggag uuggaggaag gcgcgc     46

<210> SEQ ID NO 176
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 176
gcgccguaug ggauuaagua aaugaggagu uggaggaagg gcgc     44

```
<210> SEQ ID NO 177
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 177
ccauacggcg c                                                               11

<210> SEQ ID NO 178
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 178
gcgcccuucc ucc                                                             13

<210> SEQ ID NO 179
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 179
gcgcgcguau gggauuaagu aaaugaggag uuggaggaag gcgcgc                         46

<210> SEQ ID NO 180
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 180
gcgccguaug ggauuaagua aaugaggagu uggaggaagg gcgc                           44

<210> SEQ ID NO 181
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 181
ggccggacag ccgggggaca ccauauacag acuacgauac ggcc                           44

<210> SEQ ID NO 182
<211> LENGTH: 34
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 182
rkaugggaku aaguaaauga ggrguwggag gaar                                    34

<210> SEQ ID NO 183
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 183
rkaugggaka aguaaaugag grguwggagg aar                                     33

<210> SEQ ID NO 184
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 184
guaugggauu aaguaaauga ggaguuggag gaag                                    34

<210> SEQ ID NO 185
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 185
grcrgccggv ggacaccaua uacagacuac kaua                                    34

<210> SEQ ID NO 186
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 186
grcrgccgga rggacaccau auacagacua ckaua                                   35

<210> SEQ ID NO 187
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: L-RNA

<400> SEQUENCE: 187
gacagccggg ggacaccaua uacagacuac gaua                    34

<210> SEQ ID NO 188
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 188 waaaguwgar                                               10

<210> SEQ ID NO 189
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 189
rgmgugwkag ukc                                           13

<210> SEQ ID NO 190
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 190
gggcugagcc c                                             11

<210> SEQ ID NO 191
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 191
gcagauaauc ugc                                           13

<210> SEQ ID NO 192
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 192

```
ggaccagucc                                                              10

<210> SEQ ID NO 193
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 193
ggacccaguc c                                                            11

<210> SEQ ID NO 194
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 194
ggaccuaguc c                                                            11

<210> SEQ ID NO 195
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 195
ggacucaguc c                                                            11

<210> SEQ ID NO 196
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 196
gcagguaauc ugc                                                          13

<210> SEQ ID NO 197
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 197
gcaggcaauc ugc                                                          13

<210> SEQ ID NO 198
```

```
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 198
gacaauuguc                                                            10

<210> SEQ ID NO 199
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 199
uaaaguagag                                                            10

<210> SEQ ID NO 200
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 200
aaaaguagaa                                                            10

<210> SEQ ID NO 201
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 201
aaaaguugaa                                                            10

<210> SEQ ID NO 202
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 202
gggauauagu gc                                                         12

<210> SEQ ID NO 203
<211> LENGTH: 13
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: L-RNA

<400> SEQUENCE: 203
ggcgugauag ugc                                                              13

<210> SEQ ID NO 204
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 204
ggaguguuag uuc                                                              13

<210> SEQ ID NO 205
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 205
ggcgugagag ugc                                                              13

<210> SEQ ID NO 206
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 206
agcgugauag ugc                                                              13

<210> SEQ ID NO 207
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 207
ggcguguuag ugc                                                              13

<210> SEQ ID NO 208
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA
```

```
<400> SEQUENCE: 208
ggacbyaguc c                                                        11

<210> SEQ ID NO 209
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 209
ggauacaguc c                                                        11

<210> SEQ ID NO 210
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 210
gcaggyaauc ugc                                                      13

<210> SEQ ID NO 211
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 211 gacaauwguc                                                          10

<210> SEQ ID NO 212
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: L-RNA

<400> SEQUENCE: 212
acuugucgaa agcaagyu                                                 18

<210> SEQ ID NO 213
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
rkaugggaku aaguaaauga ggrguuggag gaar                               34
```

```
<210> SEQ ID NO 214
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
grcrgccggg ggacaccaua uacagacuac kaua                                 34

<210> SEQ ID NO 215
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
ggacguaguc c                                                          11

<210> SEQ ID NO 216
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
acuugucgaa agcaagy                                                    17

<210> SEQ ID NO 217
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
auuuguugga aucaagca                                                   18

<210> SEQ ID NO 218
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
grcrgccggv aggacaccau auacagacua ckaua                                35
```

Hepcidin binding nucleic acids:
Derivatives of 238-C4-001

| Name | Sequence: 5'-3' | C(APM) | C(SPM) | Biacore |
|---|---|---|---|---|
| 238-C4-001 | AGGCUCG GACAGCCGGG-GGACACCAUAUACAGACUACGAUA CGGGCCU | 3,3 nM | | 0.89 nM |
| 238-C4-002 | GGCUCG GACAGCCGGG-GGACACCAUAUACAGACUACGAUA CGGGCC | 2,9 nM | | 0.91 nM |
| 238-C4-003 | GCUCG GACAGCCGGG-GGACACCAUAUACAGACUACGAUA CGGGC | - | | |
| 238-C4-004 | CUCG GACAGCCGGG-GGACACCAUAUACAGACUACGAUA CGGG | - | | |
| 238-C4-005 | GCGCG GACAGCCGGG-GGACACCAUAUACAGACUACGAUA CGGGC | - | | |
| 238-C4-006 | GGGCG GACAGCCGGG-GGACACCAUAUACAGACUACGAUA CGGGC | 3,6 nM | 4,8 nM | 0.91 nM |
| 238-C4-007 | GGGCA GACAGCCGGG-GGACACCAUAUACAGACUACGAUA UGCCU | - | | |
| 238-C4-008 | AGGCU GACAGCCGGG-GGACACCAUAUACAGACUACGAUA GGCCU | - | | |
| 238-C4-009 | GGGCU GACAGCCGGG-GGACACCAUAUACAGACUACGAUA AGCCU | - | | |
| 238-C4-010 | GGGCG GACAGCCGGG-GGACACCAUAUACAGACUACGAUA CGGGC | = | | |
| 238-C4-011 | GGCG GACAGCCGGG-GGACACCAUAUACAGACUACGAUA CGGC | - | | |
| 238-C4-012 | GGCG GACAGCCGGG-GGACACCAUAUACAGACUACGAUA CGCC | - | | |
| 238-C4-013 | GGCG GACAGCCGGG-GGACACCAUAUACAGACUACGAUA GGCC | - | | |
| 238-C4-014 | GGCG GACAGCCGGG-GGACACCAUAUACAGACUACGAUA GCGC | - | | |
| 238-C4-024 | GGGCG GACAGCCGGA-GGACACCAUAUACAGACUACGAUA CGGGC | | 11 nM | 2.8 nM |
| 238-C4-025 | GGGCG GACAGCCGGG-GGACACCAUAUACAGACUACGAUA CGGGC | | 17 nM | - |
| 238-C4-062 | GGGCG GACAGCCGGG AGGACACCAUAUACAGACUACGAUA CGGGC | | - | - | terminal nucleotides that may hybridize to each other (bold)

central stretch nucleotides which may mainly comprise a Hepcidin-binding motif nt.: nucleotides      variable position

C: Results of competition binding assay vs. the reference molecules 238-C4-001

Biacore: Results of Biacore measurement of Spiegelmers binding to immobilized Hepcidin

=: similar binding affinity as 238-C4-001 (C(APM)) or 238-C4-006 (C(SPM)) respectively

-: weaker binding affinity than 238-C4-001 (C(APM)) or 238-C4-006 (C(SPM)) respectively n.b.: no binding      APM: aptamer      SPM: spiegelmer

Fig. 8

Other Hepcidin binding nucleic acids

| Name | Sequence: 5'-3' | C(APM) | Biacore |
|---|---|---|---|
| 237-A5-001 | CGGGCGCCAUAGA-CCGUUAUUAAGCACUGUAACUACCGAACCGCGCCCG | - | 2.81 nM |
| 237-C5-001 | CGGGCGCCAUAGA-CCGUUAACUACA----UAACUACCGAACCGUGCCCG | - | 16.9 nM |
| 236-F2-001 | CGGGCGCUACCGAACCCACUAAAACCAGUGCAUAG-----ACCGCGCCCG | - | 25.4 nM |
| 236-G4-001 | CGGGCGCUACCGAACCGUCACGAAGAC    CAUAG    ACCGCGCC-G | - | 25.1 nM |
| 236-E3-001 | CGAGCGCAACCGAACCUCUACCCAGAC    AUAG    ACCGCGCCCG | - | 39.1nM |

C: Results of competition binding assay vs. the reference molecule 229-G1-001 (similar binding affinity as 223-C5-001)

Biacore: Results of Biacore measurement of Spiegelmers binding to immobilized Hepcidin -: weaker binding affinity than 229-G1-001 (similar binding affinity as 223-C5-001)

APM: aptamer

Fig. 9

Specificity of Hepcidin binding Spiegelmers

| Name | Human Hepcidin-25 | | Cynomolgus Hepcidin-25 | | Marmoset Hepcidin-25 | | Mouse Hepcidin-25 | Rat Hepcidin-25 | |
|---|---|---|---|---|---|---|---|---|---|
| | Biacore | Comp. Pull-down | Biacore | Comp. Pull-down | Biacore | Comp. Pull-down | Biacore | Biacore | Comp. Pull-down |
| 223-C5-001 | 2.70 nM | | | | | | | | |
| 229-B1-002 | 1.47 nM | 22 nM | | 17 nM | | | n.b. | n.b. | n.b. |
| 238-C4-006 | 0.89 nM | 2.3 nM | | 4.2 nM | | n.b. | n.b. | n.b. | n.b. |
| 238-D4-001 | 0.51 nM | 1.8 nM | | 2 nM | | | n.b. | n.b. | |
| 238-D4-008 | 0.48 nM | 1.7 nM | | 2 nM | | 7.7 nM | n.b. | n.b. | | n.b.: no binding

Fig. 10

Binding of Spiegelmers to Hepcidin-22 and Hepcidin-20

| Name | Human Hepcidin-25 | | Human Hepcidin-22 | | Human Hepcidin-20 | |
|---|---|---|---|---|---|---|
| | Biacore | Comp. Pull-down | Biacore | Comp. Pull-down | Biacore | Comp. Pull-down |
| 223-C5-001 | 2.70 nM | | n.d. | | 3.33 nM | |
| 229-B1-002 | 1.47 nM | 22 nM | n.d. | 19.2 nM | 1.80 nM | 16.2 nM |
| 238-C4-006 | 0.89 nM | 2.3 nM | n.d. | 2.2 nM | 0.92 nM | 2.3 nM |
| 238-D4-001 | 0.51 nM | 1.8 nM | n.d. | 1.2 nM | 0.55 nM | 1 nM |
| 238-D4-008 | 0.48 nM | 1.7 nM | | | 0.50 nM | 1.7 nM |

Fig. 11

Binding of PEGylated Spiegelmers to Hepcidin

| Name | Biacore | Comp. Pull-down |
|---|---|---|
| 223-C5-001-5'-PEG | 4.44 nM | |
| 229-B1-002-5'-PEG | 1.92 nM | 11 nM |
| 238-C4-006-5'-PEG | 0.76 nM | 2.8 nM |
| 238-D4-002-5'-PEG | 0.53 nM | 3.1 nM |
| 238-D4-008-5'-PEG | 0.64 nM | 1.6 nM |

Fig. 12

Fe/NTA:= FE/ nitrilotriacetate
HEP:= human Hepcidin
C5-PEG:= Spiegelmer 223-C5-001-5'-PEG

HEPCIDIN BINDING NUCLEIC ACIDS

SEQUENCE LISTING

The instant application contains a Sequence Listing which has been submitted electronically In ASCII format and is hereby incorporated by reference in its entirety. Said ASCII copy, Created on Apr. 4, 2014, is named 021315-08791600_SL.txt and is 57,151 bytes in size.

The present invention is related to nucleic acids binding to hepcidin, and the use thereof for the manufacture of a medicament, a diagnostic agent, and a detecting agent respectively.

The primary structure of hepcidin (HEPC-HUMAN, SwissProt entry P81172) was determined in 2000 (Krause, 2000). Hepcidin was discovered independently by another group investigating anti-microbial peptides (Park, 2001). Synonyms of the protein are liver-expressed anti-microbial peptide (abbreviation: LEAP-1) and Putative liver tumour regressor (abbreviation: PLTR). Hepcidin is a cysteine-rich cationic peptide and consists of 25 amino acids accounting for a molecular weight of 2,790 Dalton. The eight cysteines form four disulfide bonds and confer a stable, rigid structure to the molecule.

The tertiary structure of hepcidin was determined by NMR analysis (Hunter, 2002). The protein consists of a distorted beta-sheet with an unusual vicinal disulphide bridge found at the turn of the hairpin (Hunter, 2002).

The amino acid sequence of hepcidin from different mammalian species has generally been well conserved during evolution. Human hepcidin shares the following percentage of identical amino acids with hepcidin from:

| | |
|---|---|
| Macaca mulatta (rhesus monkey) | 100% |
| Macaca fascularis (cynomolgus monkey) | 100% |
| Sus scrofa (pig) | 84% |
| Mus musculus (mouse) | 76% |
| Rattus norvegicus (rat) | 68% |

In addition to bioactive hepcidin consisting of 25 amino acids (also referred to as hepcidin-25) two truncated inactive variants with 20 and 22 amino acids were identified: hepcidin-20 and hepcidin 22 (Rivera, 2005). All these peptides are generated on the basis of a 84 amino acid prepropeptide in human and rat and an 83 amino acid prepropeptide in mice (Pigeon, 2001). The 84 amino acid hepcidin prepropeptide contains a typical endoplasmic reticulum targeting 24-amino acid signal peptide that is removed, and a consensus cleavage site for the prohormone convertase furin (Valore, 2008). These processing steps generate the active 25 amino acids peptide hormone, found in blood and urine.

Hepcidin is the key signal regulating iron homeostasis. High levels of human hepcidin result in reduced serum iron levels whereas low levels result in increased serum iron levels as shown in hepcidin-deficiency and hepcidin overexpressing mouse models (Nicolas, 2001; Nicolas, 2002; Nicolas, 2003). In addition, mutations in the hepcidin gene which result in lack of hepcidin activity are associated with juvenile hemochromatosis, a severe iron overload disease (Roetto, 2003). After intraperitoneal injection of hepcidin a dose dependent and long lasting reduction in serum iron was observed (Rivera, 2005).

Iron is an essential element required for growth and development of all living organisms. Iron content in mammals is regulated by controlling iron absorption, iron recycling, and release of iron from cells in which it is stored. Iron is absorbed predominantly in the duodenum and upper jejunum by enterocytes.

A feedback mechanism enhances iron adsorption in individuals who are iron deficient, and reduces iron absorption in individuals with iron overload. A key compound of this mechanism is the iron transporter ferroportin which also acts as hepcidin receptor (Abboud, 2000; Donovan, 2000; McKie, 2000). Ferroportin is a 571-amino acid protein with 90% amino acid sequence identity between mice, rats, and humans which contrails the release of iron (McKie, 2000). This major iron export protein is located on the basal membrane of placental syncytiotrophoblasts and enterocytes, and on the cell surface of macrophages and hepatocytes.

Hepcidin inhibits iron release from these different ceil types by binding to ferroportin expressed on the above mentioned cell types and induces its phosphorylation, internalisation, ubiquitylation and lysosomal degradation thereby reducing ferroportin mediated release of iron into the blood (Nemeth, 2004; De Domenico, 2007). As plasma iron continues to be consumed for haemoglobin synthesis, plasma iron levels decrease and hepcidin production abates in healthy subjects.

In situations of acute and chronic systemic inflammation cytokines induce hepcidin production. Hepcidin gene expression has been observed to be increased significantly after inflammatory stimuli, such as infections, which induce the acute phase response of the innate immune system of vertebrates. In mice hepcidin gene expression was shown to be upregulated by lipopolysaccharide (Constante, 2006), turpentine (Nemeth, 2004) and Freund's complete adjuvant (Frazer, 2004), and adenoviral infections. In humans hepcidin expression is induced by the inflammatory cytokine interleukine-6 and LPS (Nemeth, 2004). A strong correlation between hepcidin expression and anemia of inflammation was also found in patients with chronic inflammatory diseases, including bacterial, fungal and viral infections. In all these conditions increased concentrations of hepcidin inhibit iron efflux from macrophages, from hepatic storage and from duodenum into plasma. Hypoferremia develops, and erythropoiesis becomes iron-limited and results in anaemia under conditions of chronic inflammation (Weiss, 2005; Weiss, 2008; Andrews, 2008).

The problem underlying the present invention is to provide a means which specifically interacts with hepcidin. More specifically, the problem underlying the present invention is to provide for a nucleic acid based means which specifically interacts with hepcidin.

A further problem underlying the present invention is to provide a means for the manufacture of a medicament for the treatment of a human or non-human diseases, whereby the disease is characterized by hepcidin being either directly or indirectly involved in the pathogenetic mechanism of such disease.

A still further problem underlying the present invention is to provide a means for the manufacture of a diagnostic agent for the treatment of a disease, whereby the disease is characterized by hepcidin being either directly or indirectly involved in the pathogenetic mechanism of such disease.

These and other problems underlying the present invention are solved by the subject matter of the attached independent claims. Preferred embodiments may be taken from the dependent claims.

Furthermore, the problem underlying the invention is solved in a first aspect which is also the first embodiment of the first aspect by a nucleic acid capable of binding to hepcidin.

In a second embodiment of the first aspect which is also an embodiment of the first embodiment of the first aspect, the nucleic acid is an antagonist of hepcidin.

In a third embodiment of the first aspect which is also an embodiment of the first and the second embodiment of the first aspect, the nucleic acid is an inhibitor of the hepcidin-ferroportin system.

In a fourth embodiment of the first aspect which is also an embodiment of the first, the second and the third embodiment of the first aspect, the nucleic acid comprises in 5'→3' direction a first terminal stretch of nucleotides, a central stretch of nucleotides and a second terminal stretch of nucleotides, wherein the central stretch of nucleotides comprises 32 to 40 nucleotides, preferably 32 to 35 nucleotides.

In a fifth embodiment of the first aspect which is also an embodiment of the first and the second embodiment of the first aspect, the nucleic acid comprises in 5'→3' direction a second terminal stretch of nucleotides, a central stretch of nucleotides and a first terminal stretch of nucleotides, wherein the central stretch of nucleotides comprises 32 to 40 nucleotides, preferably 32 to 35 nucleotides.

In a sixth embodiment of the first aspect which is also an embodiment of the fourth and the fifth embodiment of the first aspect, the central stretch of nucleotides is essential for binding to hepcidin.

In a seventh embodiment of the first aspect which is also an embodiment of the fourth, the fifth and the sixth embodiment of the first aspect, the central stretch of nucleotides comprises a nucleotide sequence of 5' RKAUGG-GAKUAAGUAAAUGAGGRGUWGGAGGAAR 3' (SEQ ID NO: 182) or 5' RKAUGGGAKAAGUAAAUGAGGR-GUWGGAGGAAR 3' (SEQ ID NO: 183).

In an eight embodiment of the first aspect which is also an embodiment of the fourth to seventh embodiment of the first aspect, the central stretch of nucleotides comprises a nucleotide sequence of 5' RKAUGGGAKUAAGUAAAUGAG-GRGUUGGAGGAAR 3' (SEQ ID NO: 213), preferably 5' GUAUGGGAUUAAGUAAAUGAGGAGUUG-GAGGAAG 3' (SEQ OD NO; 184).

In a ninth embodiment of the first aspect which is also an embodiment of the seventh and eighth embodiment of the first aspect, the first terminal stretch of nucleotides and the second terminal stretch of nucleotides optionally hybridize with each other, wherein upon hybridization a double-stranded structure is formed, the first terminal stretch of nucleotides comprises five to eight nucleotides, and the second terminal stretch of nucleotides comprises five to eight nucleotides.

In a tenth embodiment of the first aspect which is also an embodiment of the ninth embodiment of the first aspect, the double-stranded structure consists of five to eight basepairs.

In an eleventh embodiment of the first aspect which is also an embodiment of the seventh to the tenth embodiment of the first aspect,, preferably of the eight to tenth embodiment of the first aspect the first terminal stretch of nucleotides comprises a nucleotide sequence of 5' $X_1X_2X_3$SBSBC3' and the second terminal stretch of nucleotides comprises a nucleotide sequence of 5' GVBVY$X_4X_5X_6$ 3', wherein $X_1$ is A or absent, $X_2$ is G or absent, $X_3$ is B or absent, $X_4$ is S or absent, $X_5$ is C or absent, and $X_6$ is U or absent.

In a twelvth embodiment of the first aspect which is also an embodiment of the seventh to the eleventh embodiment of the first aspect, the First terminal stretch of nucleotides comprises a nucleotide sequence of 5' $X_1X_2X_3$SBSB$C_3$' and the second terminal stretch of nucleotides comprises a nucleotide sequence of 5' GVBVB$X_4X_5X_6$ 3', wherein a) $X_1$ is A, $X_2$ is G, $X_3$ is B, $X_4$ is S, $X_5$ is C, and $X_6$ is U or b) $X_1$ is absent, $X_2$ is G, $X_3$ is B, $X_4$ is S, $X_5$ is C, and $X_6$ is U or c) $X_1$ is A, $X_2$ is G, $X_3$ is B, $X_4$ is S, $X_5$ is C, and $X_6$ is absent.

In a 13$^{th}$ embodiment of the first aspect which is also an embodiment of the seventh embodiment to the twelvth embodiment of the first aspect, a) the first terminal stretch of nucleotides comprises a nucleotide sequence of 5' AGCGUGUC 3' and the second terminal stretch of nucleotides comprises a nucleotide sequence of 5' GGUGCGCU 3' or, b) the first terminal stretch of nucleotides comprises a nucleotide sequence of 5' AGCGUGUC 3' and the second terminal stretch of nucleotides comprises a nucleotide sequence of 5' GGCAUGCU 3' or c) the first terminal stretch of nucleotides comprises a nucleotide sequence of 5' AGUGUGUC 3' and the second terminal stretch of nucleotides comprises a nucleotide sequence of 5' GAUGCGCU 3' or d) the first terminal stretch of nucleotides comprises a nucleotide sequence of 5' AGUGUGUC 3' and the second terminal stretch of nucleotides comprises a nucleotide sequence of 5' GGCAUGCU 3' or e) the first terminal stretch of nucleotides comprises a nucleotide sequence of 5' AGCGUGCC 3' and the second terminal stretch of nucleotides comprises a nucleotide sequence of 5' GGUGCGCU 3' or f) the first terminal stretch of nucleotides comprises a nucleotide sequence of 5' AGCGCGCC 3' and the second terminal stretch of nucleotides comprises a nucleotide sequence of 5' GGCGCGCU 3'.

In a 14$^{th}$ embodiment of the first aspect which is also an embodiment of the seventh embodiment to the tenth embodiment of the first aspect, preferably of the eitghth to the tenth embodiment, the first terminal stretch of nucleotides comprises a nucleotide sequence of 5' $X_1X_2X_3$SBSBC3' and the second terminal stretch of nucleotides comprises a nucleotide sequence of 5' GVBVY$X_4X_5X_6$ 3', wherein a) $X_1$ is absent, $X_2$ is G, $X_3$ is B, $X_4$ is S, $X_5$ is C, and $X_6$ is absent or b) $X_1$ is absent, $X_2$ is absent, $X_3$ is B, $X_4$ is S, $X_5$ is C, and $X_6$ is absent or c) $X_1$ is absent, $X_2$ is G, $X_3$ is B, $X_4$ is S, $X_5$ is absent, and $X_6$ is absent.

In a 15$^{th}$ embodiment of the first aspect which is also an embodiment of the seventh embodiment to the twelvth and 14$^{th}$ embodiment of the first aspect, the first terminal stretch of nucleotides comprises a nucleotide sequence of 5' $X_1X_2X_3$SBSBCS3' and the second terminal stretch of nucleotides comprises a nucleotide sequence of 5' GVBVY$X_4X_5X_6$ 3', wherein $X_1$ is absent, $X_2$ is absent, $X_3$ is B or absent, $X_4$ is S or absent, $X_5$ is absent, and $X_6$ is absent.

In a 16$^{th}$ embodiment of the first aspect which is also an embodiment of the 15$^{th}$ embodiment of the first aspect, a) the first terminal stretch of nucleotides comprises a nucleotide sequence of 5' GCGCGC 3' and the second terminal stretch of nucleotides comprises a nucleotide sequence of 5' GCGCGC 3' or b) the first terminal stretch of nucleotides comprises a nucleotide sequence of 5' GGUGUC 3' and the second terminal stretch of nucleotides comprises a nucleotide sequence of 5' GGCAUC 3' or c) the first terminal stretch of nucleotides comprises a nucleotide sequence of 5' GCCGUC 3' and the second terminal stretch of nucleotides comprises a nucleotide sequence of 5' GGCGCC 3' or d) the first terminal stretch of nucleotides comprises a nucleotide sequence of 5' GCGCC 3' and the second terminal stretch of nucleotides comprises a nucleotide sequence of 5' GGCGC 3' or e) the first terminal stretch of nucleotides comprises a nucleotide sequence of 5' GGCGC 3' and the second terminal stretch of nucleotides comprises a nucleotide sequence of 5' GCGCC 3'.

In a 17$^{th}$ embodiment of the first aspect which is also an embodiment of the seventh embodiment to the 16$^{th}$ embodiment of the first aspect, the nucleic acid comprises a nucleic acid sequence according to any one of SEQ.ID.Nos. 115 to 119, SEQ.ID.No. 121, SEQ.ID.No. 142, SEQ.ID.No. 144, SEQ.ID.No. 146, SEQ.ID.No. 148, SEQ.ID.No. 151, SEQ.ID.No. 152, SEQ.ID.No. 175 or SEQ.ID.No. 176.

In an 18$^{th}$ embodiment of the first aspect which is also an embodiment of the fourth to the sixth embodiment of the first aspect, the central stretch of nucleotides comprises a nucleotide sequence of 5' GRCRGCCGGVGGACACCAUAUA-CAGACUACKAUA 3' (SEQ ID NO: 185) or 5' GRCRGC-CGGARGGACACCAUAUACAGACUACKAUA 3' (SEQ ID NO: 186).

In a 19$^{th}$ embodiment of the first aspect which is also an embodiment of the fourth to the sixth embodiment and the 18$^{th}$ embodiment of the first aspect, the central stretch of nucleotides comprises a nucleotide sequence of 5' GRCRGC-CGGGGGACACCAUAUACAGACUACKAUA 3' (SEQ ID NO: 214), preferably 5' GACAGCCGGGGGACAC-CAUAUACAGACUACGAUA 3' (SEQ ID NO: 187).

In a 20$^{th}$ embodiment of the first aspect which is also an embodiment of the 18$^{th}$ and 19$^{th}$ embodiment of the first aspect,
the first terminal stretch of nucleotides and the second terminal stretch of nucleotides optionally hybridize with each other, wherein upon hybridization a double-stranded structure is formed,
the first terminal stretch of nucleotides comprises four to seven nucleotides, and the second terminal stretch of nucleotides comprises four to seven nucleotides.

In a 21$^{st}$ embodiment of the first aspect which is also an embodiment of the 20$^{th}$ embodiment of the first aspect, the double-stranded structure consists of four to seven basepairs.

In a 22$^{nd}$ embodiment of the first aspect which is also an embodiment of the 18$^{th}$ to the 21$^{st}$ embodiment of the first aspect, the first terminal stretch of nucleotides comprises a nucleotide sequence of 5' $X_1X_2X_3$SBSN 3' and the second terminal stretch of nucleotides comprises a nucleotide sequence of 5' NSVS$X_4X_5X_6$ 3',
wherein $X_1$ is A or absent, $X_2$ is G or absent, $X_3$ is R or absent, $X_4$ is Y or absent, $X_5$ is C or absent, $X_6$ is U or absent.

In a 23$^{rd}$ embodiment of the first aspect which is also an embodiment of the 18 to the 22$^{nd}$ embodiment of the first aspect, preferably of the 19$^{th}$ to the 22$^{nd}$ embodiment of the first aspect, the first terminal stretch of nucleotides comprises a nucleotide sequence of 5' $X_1X_2X_3$SBSN 3' and the second terminal stretch of nucleotides comprises a nucleotide sequence of 5' NSVS$X_4X_5X_6$ 3',
wherein
a) $X_1$ is A, $X_2$ is G, $X_3$ is R, $X_4$ is Y, $X_5$ is C, and $X_6$ is U or
b) $X_1$ is absent, $X_2$ is G, $X_3$ is R, $X_4$ is Y, $X_5$ is C, and $X_6$ is U or
c) $X_1$ is A, $X_2$ is G, $X_3$ is R, $X_4$ is Y, $X_5$ is C, and $X_6$ is absent.

In a 24$^{th}$ embodiment of the first aspect which is also an embodiment of the 18$^{th}$ to the 23$^{rd}$ embodiment of the first aspect,
a) the first terminal stretch of nucleotides comprises a nucleotide sequence of 5' AGGCUCG 3' and the second terminal stretch of nucleotides comprises a nucleotide sequence of 5' CGGGCCU 3' or
b) the first terminal stretch of nucleotides comprises a nucleotide sequence of 5' AGGCCCG 3' and the second terminal stretch of nucleotides comprises a nucleotide sequence of 5' CGGGCCU 3' or
c) the first terminal stretch of nucleotides comprises a nucleotide sequence of 5' AGGCUUG 3' and the second terminal stretch of nucleotides comprises a nucleotide sequence of 5' CGAGCCU 3' or
d) the first terminal stretch of nucleotides comprises a nucleotide sequence of 5' AGACUUG 3' and the second terminal stretch of nucleotides comprises a nucleotide sequence of 5' CGAGUCU 3'.

In a 25$^{th}$ embodiment of the first aspect which is also an embodiment of the 18$^{th}$ to the 22$^{nd}$ embodiment of the first aspect, preferably of the 19$^{th}$ to the 22$^{nd}$ embodiment of the first aspect the first terminal stretch of nucleotides comprises a nucleotide sequence of 5' $X_1X_2X_3$SBSN3' and the second terminal stretch of nucleotides comprises a nucleotide sequence of 5' NSVS$X_4X_5X_6$ 3',
wherein
a) $X_1$ is absent, $X_2$ is G, $X_3$ is R, $X_4$ is Y, $X_5$ is C, and $X_6$ is absent or
b) $X_1$ is absent, $X_2$ is absent, $X_3$ is R, $X_4$ is Y, $X_5$ is C, and $X_6$ is absent or
c) $X_1$ is absent, $X_2$ is G, $X_3$ is R, $X_4$ is Y, $X_5$ is absent, and $X_6$ is absent.

In a 26$^{th}$ embodiment of the first aspect which is also an embodiment of the 18$^{th}$ to the 22$^{nd}$ and 25$^{th}$ embodiment of the first aspect, the first terminal stretch of nucleotides comprises a nucleotide sequence of 5' GGCUCG 3' and the second terminal stretch of nucleotides comprises a nucleotide sequence of 5' CGGGCC 3'.

In a 27$^{th}$ embodiment of the first aspect which is also an embodiment of the 18$^{th}$ to the 22$^{nd}$ embodiment of the first aspect, the first terminal stretch of nucleotides comprises a nucleotide sequence of 5' $X_1X_2X_3$SBSN 3' and the second terminal stretch of nucleotides comprises a nucleotide sequence of 5' NSVS$X_4X_5X_6$ 3',
wherein
$X_1$ is absent, $X_2$ is absent, $X_3$ is R or absent, $X_4$ is Y or absent, $X_5$ is absent, and $X_6$ is absent.

In a 28$^{th}$ embodiment of the first aspect which is also an embodiment of the 18$^{th}$ to the 22$^{nd}$ and 27$^{th}$ embodiment of the first aspect,
the first terminal stretch of nucleotides comprises a nucleotide sequence of 5' GGCCG 3' and the second terminal stretch of nucleotides comprises a nucleotide sequence of 5' CGGCC 3' or
the first terminal stretch of nucleotides comprises a nucleotide sequence of 5' GCGCG 3' and the second terminal stretch of nucleotides comprises a nucleotide sequence of 5' CGCGC 3'.

In a 29$^{th}$ embodiment of the first aspect which is also an embodiment of the first to the sixth and 18$^{th}$ to the 28$^{th}$ embodiment of the first aspect, the nucleic acid comprises a nucleic acid sequence according to any one of SEQ.ID.Nos. 122 to 126, SEQ.ID.No. 154, SEQ.ID.No. 159, SEQ.ID.No. 163 or SEQ.ID.No. 174.

In a 30th embodiment of the first aspect which is also an embodiment of the fourth to the sixth embodiment of the first aspect, the central stretch of nucleotides comprises in 5'→3' direction the following stretches of nucleotides: a Box A, a linking stretch of nucleotides and a Box B; alternatively, the central stretch of nucleotides comprises in 5'→3' direction the following stretches of nucleotides: a Box B, a linking stretch of nucleotides and a Box A, wherein the Box A comprises a nucleotide sequence of 5' WAAAGUWGAR 3' (SEQ ID NO: 188), the linking stretch of nucleotides comprises ten to eighteen nucleotides and the Box B comprises a nucleotide sequence of 5' RGMGUGWKAGUKC 3' (SEQ ID NO: 189).

In a 31st embodiment of the first aspect which is also an embodiment of the 30th embodiment of the first aspect, the Box A comprises a nucleotide sequence selected from the group of 5' UAAAGUAGAG 3' (SEQ ID NO: 199), 5' AAAAGUAGAA 3' (SEQ ID NO: 200), 5' AAAAGUUGAA 3' (SEQ ID NO: 201) and 5' GGGAUAUAGUGC 3' (SEQ ID NO: 202); preferably Box A comprises 5' UAAAGUAGAG 3' (SEQ ID NO:199).

In a 32nd embodiment of the first aspect which is also an embodiment of the 30th of the 31st embodiment of the first aspect, the Box B comprises a nucleotide sequence selected from the group of 5' GGCGUGAUAGUGC 3' (SEQ ID NO: 203), 5' GGAGUGUUAGUUC 3' (SEQ ID NO: 204), 5' GGCGUGAGAGUGC 3' (SEQ ID NO: 205), 5' AGCGUGAUAGUGC 3' and 5' GGCGUGUUAGUGC 3' (SEQ ID NO: 206) and 5' GGCGUGUUAGUGC 3' (SEQ ID NO: 207), preferably Box B comprises 5' GGCGUGAUAGUGC 3' (SEQ ID NO: 203).

In a 33rd embodiment of the first aspect which is also an embodiment of the 30th of the 32nd embodiment of the first aspect, the linking stretch of nucleotides comprises in 5'→3' direction a first linking substretch of nucleotides, a second linking substretch of nucleotides and a third linking substretch of nucleotides, wherein preferably the first linking substretch of nucleotides and the third linking substretch of nucleotides optionally hybridize to each other, wherein upon hybridization a double-stranded structure is formed.

In a 34th embodiment of the first aspect which is also an embodiment of the 33rd embodiment of the first aspect, the first linking substretch of nucleotides and the third linking substretch of nucleotides each and independently from each other comprise three to six nucleotides.

In a 35th embodiment of the first aspect which is also an embodiment of the 32nd to the 34th embodiment of the first aspect, the double-stranded structure consists of three to six base pairs.

In a 36th embodiment of the first aspect which is also an embodiment of the 32nd to the 35th embodiment of the first aspect, a) the first linking substretch of nucleotides comprises a nucleotide sequence of selected from the group of 5' GGAC 3', 5' GGAU 3' and 5' GGA 3', and the third linking substretch of nucleotides comprises a nucleotide sequence of 5' GUCC 3' or b) the first linking substretch of nucleotides comprises a nucleotide sequence of 5' GCAG 3' and the third linking substretch of nucleotides comprises a nucleotide sequence of 5' CUGC 3' or c) the first linking substretch of nucleotides comprises a nucleotide sequence of 5' GGGC 3' and the third linking substretch of nucleotides comprises a nucleotide sequence of 5' GCCC 3' or d) the first linking substretch of nucleotides comprises a nucleotide sequence of 5' GAC 3' and the third linking substretch of nucleotides comprises a nucleotide sequence of 5' GUC 3' or e) the first linking substretch of nucleotides comprises a nucleotide sequence of 5' ACUUGU 3' and the third linking substretch of nucleotides comprises a nucleotide sequence selected from the group of 5' GCAAGU 3' and 5' GCAAGC 3' or f) the first linking substretch of nucleotides comprises a nucleotide sequence of 5' UCCAG 3' and the third linking substretch of nucleotides comprises a nucleotide sequence of 5' CUGGA 3', preferably the first linking substretch of nucleotides comprises a nucleotide sequence of 5' GAC 3' and the third linking substretch of nucleotides comprises a nucleotide sequence of 5' GUC 3'.

In a 37th embodiment of the first aspect which is also an embodiment of the 33rd to the 36th embodiment of the first aspect, the second linking substretch of nucleotides comprises three to five nucleotides.

In a 38th embodiment of the first aspect which is also an embodiment of the 33rd to the 37th embodiment of the first aspect, the second linking substretch of nucleotides comprises a nucleotide sequence selected from the group of 5' VBAAW 3', 5' AAUW 3' and 5' NBW 3'.

In a 39th embodiment of the first aspect which is also an embodiment of the 38th embodiment of the first aspect, the second linking substretch of nucleotides comprises a nucleotide sequence of 5' VBAAW 3', preferably a nucleotide sequence selected from the group of 5' CGAAA 3', 5' GCAAU 3', 5' GUAAU 3' and 5' AUAAU 3'.

In a 40th embodiment of the first aspect which is also an embodiment of the 38th embodiment of the first aspect, the second linking substretch of nucleotides comprises a nucleotide sequence of 5' AAUW 3', preferably a nucleotide sequence of 5' AAUU3' or 5' AAUA 3', more preferably 5' AAUA 3'.

In a 41st embodiment of the first aspect which is also an embodiment of the 38th embodiment the second linking substretch of nucleotides comprises a nucleotide sequence of 5' NBW 3', preferably selected from the group of 5' CCA 3', 5' CUA 3', 5'UCA 3', 5'ACA 3', 5' GUU 3', 5' UGA 3' and 5' GUA 3', more preferably 5' CCA 3', 5' CUA 3', 5' UCA 3', 5' ACA 3' and 5' GUU 3'.

In a 42nd embodiment of the first aspect which is also an embodiment of the 30th to the 41st embodiment of the first aspect, the linking stretch of nucleotides comprises a nucleotide sequence selected from the group of 5' GGACBYAGUCC 3' (SEQ ID NO: 208), 5' GGAUACAGUCC 3' (SEQ ID NO: 209), 5═ GCAGGYAAUCUGC 3' ((SEQ ID NO: 210), 5' GACAAUWGUC 3' (SEQ ID NO: 211), 5' ACUUGUCGAAAGCAAGYU 3' (SEQ ID NO: 212), 5' UCCAGGUUCUGGA 3' (SEQ ID NO: 109), 5' GGGCUGAGCCC 3' (SEQ ID NO: 190), 5' GCAGAUAAUCUGC 3' (SEQ ID NO: 191) and 5' GGACCAGUCC 3' (SEQ ID NO: 192), preferably selected from the group of 5' GGACCCAGUCC 3' (SEQ ID NO: 193), 5' GGACCUAGUCC 3' (SEQ ID NO: 194), 5' GGACUCAGUCC 3' (SEQ ID NO: 195), 5' GCAGGUAAUCUGC 3' (SEQ ID NO: 196), 5' GCAGGCAAUCGC 3' (SEQ ID NO: 197), 5' GACAAUUGUC 3' (SEQ ID NO: 198) and 5" GACAAUAGUC 3' (SEQ ID NO: 157).

In a 43rd embodiment of the first aspect which is also an embodiment of the 30th to the 42nd embodiment of the first aspect the first terminal stretch of nucleotides and the second terminal stretch of nucleotides optionally hybridize with each other, wherein upon hybridization a double-stranded structure is formed,
the first terminal stretch of nucleotides comprises four to seven nucleotides, and
the second terminal stretch of nucleotides comprises four to seven nucleotides.

In a 44th embodiment of the first aspect which is also an embodiment of the 43rd embodiment of the first aspect, the double-stranded structure consists of four to seven base pairs.

In a 45th embodiment of the first aspect which is also an embodiment of the 30th to the 44th embodiment of the first aspect, the first terminal stretch of nucleotides comprises a nucleotide sequence of 5' $X_1X_2X_3BKBK$ 3' and the second terminal stretch of nucleotides comprises a nucleotide sequence of 5' $MVVVX_4X_5X_6$ 3'.
wherein $X_1$ is G or absent, $X_2$ is S or absent, $X_3$ is V or absent, $X_4$ is B or absent, $X_5$ is S or absent, $X_6$ is C or absent.

In a 46th embodiment of the first aspect which is also an embodiment of the 30th to the 44th embodiment of the first aspect, the first terminal stretch of nucleotides comprises a nucleotide sequence of 5' $X_1X_2X_3BKBK$ 3' and the second terminal stretch of nucleotides comprises a nucleotide sequence of 5' $MVVVX_4X_5X_6$ 3',
wherein
a) $X_1$ is G, $X_2$ is S, $X_3$ is V, $X_4$ is B, $X_5$ is S, and $X_6$ is C or
b) $X_1$ is absent, $X_2$ is S, $X_3$ is V, $X_4$ is B, $X_5$ is S, and $X_6$ is C or
c) $X_1$ is G, $X_2$ is S, $X_3$ is V, $X_4$ is B, $X_5$ is S, and $X_6$ is absent.

In a 47th embodiment of the first aspect which is also an embodiment of the 30th to the 46th embodiment of the first aspect, preferably of the 46th embodiment of the first aspect, the first terminal stretch of nucleotides comprises a nucleotide sequence of 5' GCACUCG 3' and the second terminal stretch of nucleotides comprises a nucleotide sequence of 5' CGAGUGC 3'.

In a 48th embodiment of the first aspect which is also an embodiment of the 30th to the 45th embodiment of the first aspect, the first terminal stretch of nucleotides comprises a nucleotide sequence of 5' $X_1X_2X_3BKBK$ 3' and the second terminal stretch of nucleotides comprises a nucleotide sequence of 5" $MVVX_4X_5X_6$ 3',
wherein
a) $X_1$ is absent, $X_2$ is S, $X_3$ is V, $X_4$ is B, $X_5$ is S, and $X_6$ is absent or
b) $X_1$ is absent, $X_2$ is absent, $X_3$ is V, $X_4$ is B, $X_5$ is S, and $X_6$ is absent or
c) $X_1$ is absent, $X_2$ is S, $X_3$ is V, $X_4$ is B, $X_5$ is absent, and $X_6$ is absent.

In a 49th embodiment of the first aspect which is also an embodiment of the 30th to the 45th and 48th embodiment of the first aspect,
a) the first terminal stretch of nucleotides comprises a nucleotide sequence of 5' GCUGUG 3' and the second terminal stretch of nucleotides comprises a nucleotide sequence of 5' CACAGC 3' or
b) the first terminal stretch of nucleotides comprises a nucleotide sequence of 5' CGUGUG 3' and the second terminal stretch of nucleotides comprises a nucleotide sequence of 5' CACACG 3' or
c) the first terminal stretch of nucleotides comprises a nucleotide sequence of 5' CGUGCU 3' and the second terminal stretch of nucleotides comprises a nucleotide sequence of 5' AGCACG 3' or
d) the first terminal stretch of nucleotides comprises a nucleotide sequence of 5' CGCGCG 3' and the second terminal stretch of nucleotides comprises a nucleotide sequence of 5' CGCGCG 3' or e) the first terminal stretch of nucleotides comprises a nucleotide sequence of 5' GCCGUG 3' and the second terminal stretch of nucleotides comprises a nucleotide sequence of 5' CACGCG 3' or
f) the first terminal stretch of nucleotides comprises a nucleotide sequence of 5' GCGGUG 3' and the second terminal stretch of nucleotides comprises a nucleotide sequence of 5' CACCGC 3' or
g) the first terminal stretch of nucleotides comprises a nucleotide sequence of 5' GCUGCG 3' and the second terminal stretch of nucleotides comprises a nucleotide sequence of 5' CGCAGC 3' or
h) the first terminal stretch of nucleotides comprises a nucleotide sequence of 5' GCUGGG 3' and the second terminal stretch of nucleotides comprises a nucleotide sequence of 5' CCCAGC 3' or
i) the first terminal stretch of nucleotides comprises a nucleotide sequence of 5' GCGGCG 3' and the second terminal stretch of nucleotides comprises a nucleotide sequence of 5' CGCCGC 3'.

In a 50th embodiment of the first aspect which is also an embodiment of the 30th to the 45th embodiment of the first aspect, the first terminal stretch of nucleotides comprises a nucleotide sequence of 5' $X_1X_2X_3BKBK$ 3' and the second terminal stretch of nucleotides comprises a nucleotide sequence of 5' $MVVVX_4X_5X_6$ 3',
wherein
$X_1$ is absent, $X_2$ is absent, $X_3$ is V or absent, $X_4$ is B or absent, $X_5$ is absent, and $X_6$ is absent.

In a 51st embodiment of the first aspect which is also an embodiment of the 30th to the 45th and 50th embodiment of the first aspect,
the first terminal stretch of nucleotides comprises a nucleotide sequence of 5' CGUG 3' and the second terminal stretch of nucleotides comprises a nucleotide sequence of 5' CACG 3'.

In a 52nd embodiment of the first aspect which is also an embodiment of the first to the sixth and of the 30th to the 11st embodiment of the first aspect, the nucleic acid comprises a nucleic acid sequence according to any one of SEQ.ID.No. 29, SEQ.ID.No. 33, SEQ.ID.No. 34, SEQ.ID.Nos. 39 to 41, SEQ.ID.No. 43, SEQ.ID.No. 46, SEQ.ID.Nos 137 to 141 or SEQ.ID.No. 173.

In a 53nd embodiment of the first aspect which is also an embodiment of the first to the sixth embodiment of the first aspect, the nucleic acid comprises a nucleic acid sequence according to any one of SEQ.ID.Nos 127 to 131.

In a 54th embodiment of the first aspect which is also an embodiment of the first to the 53rd embodiment of the first aspect, the nucleic acid is capable of binding to hepcidin, wherein hepcidin is human hepcidin-25, human hepcidin-22, human hepcidin-20, monkey hepcidin-25, monkey hepcidin-22, monkey hepcidin-20, preferably human hepcidin-25.

In a 55th embodiment of the first aspect which is also an embodiment of the first to the 54th embodiment of the first aspect, preferably of the 54th embodiment of the first aspect, the hepcidin has an amino acid sequence according to SEQ ID No. 1.

In a 56th embodiment of the first aspect which is also an embodiment of the first to the 55th embodiment of the first aspect, the nucleic acid comprises a modification group, wherein excretion rate of the nucleic acid molecule comprising the modification group from an organism is decreased compared to a nucleic acid not comprising the modification group.

In a 57th embodiment of the first aspect which is also an embodiment of the first to the 55th embodiment of the first aspect, the nucleic acid comprises a modification group, wherein the nuceic acid molecule comprising the modification group has an increased retention time in an organism compared to a nucleic acid not comprising the modification group.

In a 58$^{th}$ embodiment of the first aspect which is also an embodiment of the 56$^{th}$ and 57$^{th}$ embodiment of the first aspect, the modification group is selected from the group comprising biodegradable and non-biodegradable modifications, preferably the modification group is selected from the group comprising of linear poly (ethylene) glycol, branched poly (ethylene) glycol, hydroxyethyl starch, a peptide, a protein, a polysaccharide, a sterol, polyoxypropylene, polyoxyamidate, poly (2-hydroxyethyl)-L-glutamine and polyethylene glycol.

In a 59$^{th}$ embodiment of the first aspect which is also an embodiment of the 58$^{th}$ embodiment of the first aspect, the modification group is a PEG moiety consisting of a straight or branched PEG, wherein the molecular weight of the PEG moiety is preferably from about 20,000 to about 120,000 Da, more preferably from about 30,000 to about 80,000 Da and most preferably about 40,000 Da.

In a 60$^{th}$ embodiment of the first aspect which is also an embodiment of the 58$^{th}$ embodiment of the first aspect, the modification group is a HES moiety, wherein preferably the molecular weight of the HES moiety is from about 10,000 to 200,000 Da, more preferably from about 30,000 to 170,000 Da and most preferably about 150,000 Da.

In a 61$^{st}$ embodiment of the first aspect which is also an embodiment of the 56$^{th}$ to the 60$^{th}$ embodiment of the first aspect, the modification group is coupled to the nucleic acid via a linker, whereby preferably the linker is a biodegradable linker.

In a 62$^{nd}$ embodiment of the first aspect which is also an embodiment of the 56$^{th}$ to the 61$^{st}$ embodiment of the first aspect, the modification group is coupled to the 5'-terminal nucleotide and/or the 3'-terminal nucleotide of the nucleic acid and/or to a nucleotide of the nucleic acid between the 5'-terminal nucleotide of the nucleic acid and the 3'-terminal nucleotide of the nucleic acid.

In a 63$^{rd}$ embodiment of the first aspect which is also an embodiment of the 56$^{th}$ to the 62$^{nd}$ embodiment of the first aspect, the organism is an animal or a human body, preferably a human body.

In a 64$^{th}$ embodiment of the first aspect which is also an embodiment of the first to the 63$^{rd}$ embodiment of the first aspect, the nucleotides of or the nucleotides forming the nucleic acid are L-nucleotides.

In a 65$^{th}$ embodiment of the first aspect which is also an embodiment of the 1$^{st}$ to the 64$^{th}$ embodiment of the first aspect, the nucleic acid is an L-nucleic acid.

In a 66$^{th}$ embodiment of the first aspect which is also an embodiment of the first to the 65$^{th}$ embodiment of the first aspect, the nucleic acid comprises at least one binding moiety which is capable of binding hepcidin, wherein such binding moiety consists of L-nucleotides.

In a 67$^{th}$ embodiment of the first aspect which is also an embodiment of the first to the 66$^{th}$ embodiment of the first aspect, the nucleic acid is or is suitable for use in a method for the treatment and/or prevention of a disease.

The problem underlying the invention is solved in a second aspect which is also the first embodiment of the second aspect by a pharmaceutical composition comprising a nucleic acid according to any embodiment of the first aspect and optionally a farther constituent, wherein the further constituent is selected from the group comprising pharmaceutically acceptable excipients, pharmaceutically acceptable carriers and pharmaceutically active agents.

In a second embodiment of the second aspect which is also an embodiment of the first embodiment of the second aspect, the pharmaceutical composition comprises a nucleic acid according to any embodiment of the first aspect and a pharmaceutically acceptable carrier.

The problem underlying the invention is solved in a third aspect which is also the first embodiment of the third aspect by the use of a nucleic acid according to any embodiment of the first aspect for the manufacture of a medicament.

In a second embodiment of the third aspect which is also an embodiment of the first embodiment of the third aspect, the medicament is for use in human medicine or for use in veterinary medicine.

The problem underlying the invention is solved in a fourth aspect which is also the first embodiment of the fourth aspect by the se of a nucleic acid according to any embodiment of the first aspect for the manufacture of a diagnostic means.

In a third embodiment of the third aspect which is also an embodiment of the first and the second embodiment of the third aspect, the medicament is for the treatment and/or prevention of anemia, hypoferremia, plea, conditions with elevated hepcidin level, conditions with elevated iron level or conditions with iron overload.

In a fourth embodiment of the third aspect which is also an embodiment of the third embodiment of the third aspect, the anemia is selected from the group consisting of sideroblastic anemia, hypochromic microcytic anemia, anemia caused by chronic disease and/or disorder, anemia caused by inflammation, anemia caused by genetic disorders, anemia caused by acute infections, anemia caused by mutation in genes of iron metabolism and/or homeostasis, and anemia caused by cancer treatment.

In a fifth embodiment of the third aspect which is also an embodiment of the fourth embodiment of the third aspect, the chronic disease and/or disorder is selected from the group of chronic inflammation, cancer, auoimmune disease and/or disorder, chronic infection, arteriosclerosis, atherosclerosis, and cirrhosis of the liver.

In a sixth embodiment of the third aspect which is also an embodiment of the fifth embodiment of the third aspect, chronic inflammation is selected from the group of chronic kidney disease, chronic obstructive pulmonary disease, multiple sclerosis, osteoarthritis, diabetes, obesity, cerebrovascular disease, congestive heart disease, congestive heart failure, myocardial infarction, coronary artery disease, peripheral occlusive arterial disease, pancreatitis and vasculitis, wherein preferably chronic kidney disease is selected from the group of renal diseases, chronic renal failure and chronic kidney failure and wherein chronic kidney disease is caused by kidney dialysis or kidney transplantation.

In a seventh embodiment of the third aspect which is also an embodiment of the fifth embodiment of the third aspect, auoimmune disease and/or disorder is selected from the group of rheumatoid arthritis, irritable bowel syndrome, systemic lupus erythematosus and Chrohn's disease.

In an eight embodiment of the third aspect which is also an embodiment of the firth embodiment of the third aspect, chronic infection is selected from the group of viral infection, viral illness, bacterial infection and fungal infections, wherein preferably the viral infections comprise hepatitis and HIV infection and the bacterial infections comprise H. pyelori infection.

In a ninth embodiment of the third aspect which is also an embodiment of the first to the fourth embodiment of the third aspect, andemia caused by inflammation is normocytic to microlytic and/or characterized by a low reticulocyte production index and/or increased markers of inflammation.

In a tenth embodiment of the third aspect which is also an embodiment of the fourth embodiment of the third aspect, the genetic disorder is the Castleman disease, Schnitzler's syndrome, iron refractory iron deficiency anemia (matriptase-2 (TMPRSS6) mutation, atransferrinemia, congenital dyserythropoietic anemia or hemoglobinopathies.

In an eleventh embodiment of the third aspect which is also an embodiment of the fourth embodiment of the third aspect, the acute infection is selected from the group of viral infection, bacterial infection fungal infection, preferably sepsis.

In a twelfth embodiment of the third aspect which is also an embodiment of the fifth embodiment of the third aspect, the cancer is selected from the group of hepatocellular carcinoma, lymphoma, multiple myeloma, head-and-neck cancer, breast cancer, colarectal cancer, nonmycloid cancers, renal cell carcinoma, non-small-cell lung cancer, tumors and brain tumors.

In a $13^{th}$ embodiment of the third aspect which is also an embodiment of the third embodiment of the third aspect, the medicament is for the treatment of conditions with elevated iron level, whereby the conditions are selected from the group of ataxia, Friedrich's ataxia, age-related macular degeneration, age-related cataract, age-related retinal diseases and neurodegenerative disease, whereby such neurodegenerative disease is preferably selected from the group comprising Alzheimer's disease, Parkinson's disease, pantothenate kinase-associated neurodegeneration, restless leg syndrom and Huntington's disease.

In a $14^{th}$ embodiment of the third aspect which is also an embodiment of the third embodiment of the third aspect, the medicament is for the treatment of iron overload, whereby the hepcidin plasma level is not elevated.

In a $15^{th}$ embodiment of the third aspect which is also an embodiment of the $14^{th}$ embodiment of the third aspect, iron overload is selected from the group of transfusional iron overload, iron intoxication, pulmonary hemosiderosis, osteopenia, insulin resistense, African iron overload, Hallervordan Spatz disease, hyperferritinemia, ceruloplasmin deficiency, neonatal hemochromatosis and red blood cell disorder comprising thalassemia, alpha thalassemia, thalassemia intermedia, sickle cell disease and myelodyplastic syndrome.

In a $16^{th}$ embodiment of the third aspect which is also an embodiment of the twelfth to the $15^{th}$ embodiment of the third aspect, the medicament is used in combination with an iron chelating compound.

In a $17^{th}$ embodiment of the third aspect which is also an embodiment of the $16^{th}$ embodiment of the third aspect, the iron chelating compound is selected from the group of curcumin, deferoxamine, deferasirox and deferiprone.

In an $18^{th}$ embodiment of the third aspect which is also an embodiment of the first embodiment of the third aspect, the medicament is used for or is for use in combination with a further medicament or method of treatment, wherein such medicament or method of treatment comprises a further pharmaceutically active compound or the administration of such further pharmaceutically active compound, wherein such further pharmaceutically active compound is selected from the group of iron supplements, vitamin supplements, red cell production stimulators, antibiotics, anti-inflammatory biologies, suppressors of the immune system, anti-thrombolytics, statins, vasopressors and inotropic compounds.

The problem underlying the invention is solved in a fifth aspect which is also the first embodiment of the fifth aspect by a complex comprising a nucleic acid according to any embodiment of the first aspect and hepcidin, wherein preferably the complex is a crystalline complex.

In a second embodiment of the fifth aspect which is also an embodiment of the first embodiment of the fifth aspect, hepcidin is selected from the group comprising human hepcidin, monkey hepcidin, more preferably hepcidin is human hepcidin.

The problem underlying the invention is solved in a sixth aspect which is also the first embodiment of the sixth aspect by the use of a nucleic acid according to any embodiment of the first aspect for the detection of hepcidin.

In a second embodiment of the sixth aspect which is also an embodiment of the first embodiment of the sixth aspect, the hepcidin is selected from the group comprising human hepcidin, monkey hepcidin, more preferably hepcidin is human hepcidin.

The problem underlying the invention is solved in a seventh aspect which is also the first embodiment of the seventh aspect by a method for the screening of an antagonist or a agonist of hepcidin comprising the following steps:
  providing a candidate antagonist and/or a candidate agonist of hepcidin,
  providing a nucleic acid according to any embodiment of the first aspect,
  providing a test system which provides a signal in the presence of an antagonist and/or an agonist of hepcidin, and
  determining whether the candidate antagonist is an antagonist of hepcidin and/or whether the candidate agonist is an agonist of hepcidin.

In a second embodiment of the seventh aspect which is also an embodiment of the first embodiment of the seventh aspect, the hepcidin is selected from the group comprising human hepcidin, monkey hepcidin, more preferably hepcidin is human hepcidin.

The problem underlying the invention is solved in an eighth aspect which is also the first embodiment of the eighth aspect by a kit for the detection of hepcidin comprising a nucleic acid according to any embodiment of the first aspect, wherein preferably the hepcidin is human hepcidin.

The problem underlying the invention is solved in a ninth aspect which is also the first embodiment of the ninth aspect by a method for the detection of the nucleic acid according to any embodiment of the first aspect in a sample, wherein the method comprises the steps of:
  a) providing a sample containing the nucleic acid according to the present invention;
  b) providing a capture probe, wherein the capture probe is at least partially complementary to a first part of the nucleic acid according to any embodiment of the first aspect, and a detection probe, wherein the detection probe is at least partially complementary to a second part of the nucleic acid according to any embodiment of the first aspect, or, alternatively, the capture probe is at least partially complementary to a second part of the nucleic acid according to any embodiment of the first aspect and the detection probe is at least partially complementary to the first part of the nucleic acid according to any embodiment of the first aspect;
  c) allowing the capture probe and the detection probe to react either simultaneously or in any order sequentially with the nucleic acid according to any embodiment of the first aspect or part thereof;
  d) optionally detecting whether or not the capture probe is hybridized to the nucleic acid according to the nucleic acid according to any embodiment of the first aspect provided in step a); and e) detecting the complex formed in step c) consisting of the nucleic acid according to any embodiment of the first aspect and the capture probe and the detection probe.

In a second embodiment of the ninth aspect which is also an embodiment of the first embodiment of the ninth aspect, the detection probe comprises a detection means, and/or wherein the capture probe can be immobilized to a support, preferably a solid support.

In a third embodiment of the ninth aspect which is also an embodiment of the first and second embodiment of the ninth aspect, any detection probe which is not part of the complex is removed from the reaction so that in step e) only a detection probe which is part of the complex, is detected.

In a fourth embodiment of the ninth aspect which is also an embodiment of the first, second and third embodiment of the ninth aspect, step e) comprises the step of comparing the signal generated by the detection means when the capture probe and the detection probe are hybridized in the presence of the nucleic acid according to any embodiment of the first aspect or part thereof, and in the absence of said nucleic acid or part thereof.

The features of the nucleic acid according to the present invention as described herein can be realised in any aspect of the present invention where the nucleic acid is used, either alone or in any combination.

In connection with the present invention, preferably, the term "providing a sample" is different from and does not comprise a method of treatment or diagnosis of a human or animal body.

Human hepcidin-25 is a basic protein having the amino acid sequence according to SEQ. ID. Nos. 1 and a pI of 8.2.

The present invention is based on the surprising finding that it is possible to generate nucleic acids binding specifically and with high affinity to hepcidin. Such nucleic acids are preferably also referred to herein as the nucleic acid molecules according to the present invention, the nucleic acids according to the present invention, the inventive nucleic acids or the inventive nucleic acid molecules.

The finding that short high affinity binding nucleic acids to human hepcidin could be identified, is insofar surprising as Eaton et al. (1997) observed that the generation of aptamers, i.e. D-nucleic acids binding to a target molecule, directed to a basic protein is in general very difficult because this kind of target produces a high but non-specific signal-to-noise ratio. This high signal-to-noise ratio results from the high non-specific affinity shown by nucleic acids for basic targets such as human hepcidin.

As outlined in more detail in the claims and example 1, the present inventors could mere surprisingly identify a number of different human hepcidin binding nucleic acid molecules, whereby most of the nucleic acids could be characterised in terms of stretches of nucleotide which are also referred to herein as Boxes. The various human hepcidin binding nucleic acid molecules can be categorised as Type A, Type B and Type C hepcidin binding nucleic acids based on said Boxes and some additional structural features and elements, respectively.

The different types of hepcidin binding nucleic acids comprise different stretches of nucleotides. Accordingly, the different types of hepcidin binding nucleic acids show a different binding behaviour to the different hepcidin peptides. As demonstrated in the Examples hepcidin binding nucleic acids according to the present invention bind to human hepcidin-25, human hepcidin-22, human hepcidin-20, cynomolgus hepcidin-25 and marmoset hepcidin-25.

It is to be acknowledged that whenever it is referred herein to hepcidin, such hepcidin is hepcidin-25, if not indicated to the contrary.

It is within the present invention that the nucleic acids according to the present invention comprise two or more stretches or part(s) thereof can, in principle, hybridise with each other. Upon such hybridisation a double-stranded structure is formed. It will be acknowledged by the ones skilled in the art that such hybridisation may or may not occur, particularly under in vitro and/or in vivo conditions. Also, in case of such hybridisation, it is not necessarily the case that the hybridisation occurs over the entire length of the two stretches where, at least based on the rules for base pairing, such hybridisation and thus formation of a double-stranded structure may, in principle, occur. As preferably used herein, a double-stranded structure is a part of a nucleic acid molecule or a structure formed by two or more separate strands or two spatially separated stretches of a single strand of a nucleic acid molecule, whereby at least one, preferably two or more base pairs exist which are base pairing preferably in accordance with the Watson-Crick base pairing rules. It will also be acknowledged by the one skilled in the art that other base pairing such as Hoogsten base pairing may exist in or form such double-stranded structure. It is also to be acknowledged that the feature that two stretches hybridize preferably indicates that such hybridization is assumed to happen due to base complementarity of the two stretches.

In a preferred embodiment the term arrangement as used herein, means the order or sequence of structural or functional features or elements described herein in connection with the nucleic acids disclosed herein.

It will be acknowledged by the person skilled in the art that the nucleic acids according to the present invention are capable of binding to hepcidin. Without wishing to be bound by any theory, the present inventors assume that the hepcidin binding results from a combination of three-dimensional structural traits or elements of the claimed nucleic acid molecule, which are caused by orientation and folding patterns of the primary sequence of nucleotides forming such traits or elements. It is evident that the individual trait or element may be formed by various different individual sequences the degree of variation of which may vary depending on the three-dimensional structure such element or trait has to form. The overall binding characteristic of the claimed nucleic acid results from the interplay of the various elements and traits, respectively, which ultimately results in the interaction of the claimed nucleic acid with its target, i. e. hepcidin. Again without being wished to be bound by any theory, the central stretch that is characteristic for Type B and Type C hepcidin binding nucleic acids, and the first stretch Box A and the second stretch Box B that are characteristic for Type A hepcidin binding nucleic acids, seem to be important for mediating the binding of the claimed nucleic acid with hepcidin. Accordingly, the nucleic acids according to the present invention are suitable for the interaction with and detection of hepcidin. Also, it will be acknowledged by the person skilled in the art that the nucleic acids according to the present invention are antagonists to hepcidin. Because of this the nucleic acids according to the present invention are suitable for the treatment and prevention, respecticely, of any disease or condition which is associated with or caused by hepcidin. Such diseases and conditions may be taken from the prior art which establishes that hepcidin is involved or associated with said diseases and conditions, respectively, and which is incorporated herein by reference providing the scientific rationale for the therapeutic and diagnostic use of the nucleic acids according to the invention.

It is within the present invention that the nucleic acid according to the present invention is a nucleic acid molecule. Insofar the terms nucleic acid and nucleic acid molecule are used herein in a synonymous manner if not indicated to the contrary. In one embodiment of the present application the nucleic acid and thus the nucleic acid molecule comprises a nucleic acid molecule which is characterized in that all of the consecutive nucleotides forming the nucleic acid molecule are linked with or connected to each other by one or more than one covalent bond. More specifically, each of such nucleotides is linked with or connected to two other nucleotides, preferably through phosphodiester bonds or other bonds, forming a stretch of consecutive nucleotides. In such arrangement, however, the two terminal nucleotides, i.e. preferably the nucleotide at the 5' end and at the 3' end, are each linked to a single nucleotide only under the proviso that such arrangement is a linear and not a circular arrangement and thus a linear rather than a circular molecule.

In another embodiment of the present application the nucleic acid and thus the nucleic acid molecule comprises at least two groups of consecutive nucleotides, whereby within each group of consecutive nucleotides each nucleotide is linked with or connected to two other nucleotides, preferably through phosphodiester bonds or other bonds, forming a stretch of consecutive nucleotides. In such arrangement, however, the two terminal nucleotides, i.e. preferably the nucleotide at the 5' end and at the 3' end, of each of said at least two groups of consecutive nucleotides are each linked to a single nucleotide only. In such embodiment, the two groups of consecutive nucleotides, however, are not linked with or connected to each other through a covalent bond which links one nucleotide of one group and one nucleotide of another or the other group through a covalent bond, preferably a covalent bond formed between a sugar moiety of one of said two nucleotides and a phosphor moiety of the other of said two nucleotides or nucleosides- In an alternative embodiment, the two groups of consecutive nucleotides, however, are linked with or connected to each other through a covalent bond which links one nucleotide of one group and one nucleotide of another or the other group through a covalent bond, preferably a covalent bond formed between a sugar moiety of one of said two nucleotides and a phosphor moiety of the other of said two nucleotides or nucleosides. Preferably, the at least two groups of consecutive nucleotides are not linked through any covalent bond. In another preferred embodiment, the at least two groups are linked through a covalent bond which is different from a phosphodiester bond. In still another embodiment, the at least two groups are linked through a covalent bond which is a phosphodiester bond. Furthermore, preferably, the two groups of consecutive nucleotides are linked or connected to each other through a covalent bond whereby the covalent bond is formed between the nucleotide at the 3'-end of the first of the two groups of consecutive nucleotides and the nucleotide at the 5'-end of the second of the two groups of consecutive nucleotides or the covalent bond is formed between the nucleotide at the 5'-end of the first of the two groups of consecutive nucleotides and the nucleotide at the 3'-end of the second of the two groups of consecutive nucleotides.

The nucleic acids according to the present invention shall also comprise nucleic acids which are essentially homologous to the particular sequences disclosed herein. The term substantially homologous shall preferably be understood such that the homology is at least 75%, preferably 85%, more preferably 90% and most preferably more than 95%, 96%, 97%, 98% or 99%.

The homology between two nucleic acid molecules can be determined as known to the person skilled in the art. More specifically, a sequence comparison algorithm may be used for calculating the percent sequence homology for the test sequence(s) relative to the reference sequence, based on the designated program parameters. The test sequence is preferably the sequence or nucleic acid molecule which is said to be homologous or to be tested whether it is homologous, and if so, to what extent, to a different nucleic acid molecule, whereby such different nucleic acid molecule is also referred to as the reference sequence. In an embodiment, the reference sequence is a nucleic acid molecule as described herein, more preferably a nucleic acid molecule having a sequence according to any one of SEQ.ID.No. 29 to 43, SEQ.ID.No. 45 to 48, SEQ.ID.No. 110 to 156, SEQ.ID.No. 158 to 176 or SEQ.ID.No. 179 to 181. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST "), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al., 2004).

The term inventive nucleic acid or nucleic acid according to the (present) invention, whereby both terms are used in an interchangeable manner, shall also comprise those nucleic acids comprising the nucleic acids sequences disclosed herein or part thereof, preferably to the extent that the nucleic acids or said parts are involved in the binding to human hepcidin. Such nucleic acid is, in an embodiment, one of the nucleic acid molecules described herein, or a derivative and/or a metabolite thereof, whereby such derivative and/or metabolite are preferably a truncated nucleic acid compared to the nucleic acid molecules described herein. Truncation may be related to either or both of the ends of the nucleic acids as disclosed herein. Also, truncation may be related to the inner sequence of nucleotides of the nucleic acid, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention can be determined by the ones skilled in the art using routine experiments or by using or adopting a method as described herein, preferably as described herein in the example part.

The nucleic acids according to the present invention may be either D-nucleic acids or L-nucleic acids. Preferably, the inventive nucleic acids are L-nucleic acids. In addition it is possible that one or several parts of the nucleic acid are present as D-nucleic acids or at least one or several parts of the nucleic acids are L-nucleic acids. The term "part" of the nucleic acids shall mean as little as one nucleotide. Therefore, in a particularly preferred embodiment, the nucleic acids according to the present invention consist of L-nucleotides and comprise at least one D-nucleotide. Such D-nucleotide is preferably attached to a part different from the stretches defining the nucleic acids according to the present invention, preferably those parts thereof, where an interaction with other parts of the nucleic acid or with the target, i.e. hepcidin, is involved. Preferably, such D-nucleotide is attached at a terminus of any of the stretches or at a terminus of any nucleic acid according to the present invention, respectively. In a further preferred embodiment, such D-nucleotides may act as a spacer or a linker, preferably attaching modifications or modification groups, such as PEG and HES to the nucleic acids according to the present invention.

It is also within an embodiment of the present invention that each and any of the nucleic acid molecules described herein in their entirety in terms of their nucleic acid sequence(s) are limited to the particular nucleotide sequence(s). In other words, the terms "comprising" or "comprise(s)" shall be interpreted in such embodiment in the meaning of containing or consisting of.

It is also within the present invention that the nucleic acids according to the present invention are part of a longer nucleic acid whereby this longer nucleic acid comprises several parts whereby at least one such part is a nucleic acid according to the present invention, or a part thereof. The other part(s) of these longer nucleic acids can be either one or several D-nucleic acid(s) or one or several L-nucleic acid(s). Any combination may be used in connection with the present invention. These other part(s) of the longer nucleic acid either alone or taken together, either in their entirety or in a particular combination, can exhibit a function which is different from binding, preferably from binding to hepcidin. One possible function is to allow interaction with other molecules, whereby such other molecules preferably are different from hepcidin, such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

L-nucleic acids or L-nucleic acid molecules as used herein are nucleic acids or nucleic acid molecules consisting of L-nucleotides, preferably consisting completely of L-nucleotides.

D-nucleic acids or D-nucleic acid molecules as used herein are nucleic acids or nucleic acid molecules consisting of D-nucleotides, preferably consisting completely of D-nucleotides.

Also, if not indicated to the contrary, any nucleotide sequence is set forth herein in 5'→3' direction.

As preferably used herein any position of a nucleotide is determined or referred to relative to the 5' end of a sequence, a stretch or a substretch. Accordingly, a second nucleotide is the second nucleotide counted from the 5' end of the sequence, stretch and substretch, respectively. Also, in accordance therewith, a penultimate nucleotide is the second nucleotide counted from the 3' end of a sequence, stretch and substretch, respectively.

Irrespective of whether the inventive nucleic acid consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

Designing the inventive nucleic acids as L-nucleic acids is advantageous for several reasons. L-nucleic acids are enantiomers of naturally occurring nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this the biological half-life of the L-nucleic acid is significantly increased in such a system, including the animal and human body. Due to the lacking degradability of L-nucleic acids no nuclease degradation products are generated and thus no side effects arising therefrom observed. This aspect delimits the L-nucleic acids of factually all other compounds which are used in the therapy of diseases and/or disorders involving the presence of hepcidin. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called Spiegelmers. Aptamers as such are known to a person skilled in the art and are, among others, described in 'The Aptamer Handbook' (eds. Klussmann, 2006).

It is also within the present invention that the nucleic acids according to the invention, regardless whether they are present as D-nucleic acids, L-nucleic acids or D, L-nucleic acids or whether they are DNA or RNA, may be present as single-stranded or double-stranded nucleic acids. Typically, the inventive nucleic acids are single-stranded nucleic acids which exhibit defined secondary structures due to the primary sequence and may thus also form tertiary structures. The inventive nucleic acids, however, may also be double-stranded in the meaning that two strands regardless whether they are two separate strands or whether they are bound, preferably covalently, to each other, which are complementary or partially complementary to each other are hybridised to each other.

The inventive nucleic acids may be modified. Such modifications may be related to a single nucleotide of the nucleic acid and are well known in the art. Examples for such modification are described in, among others, Venkatesan (2003); Kusser (2000); Aurup (1994); Cummins (1995); Eaton (1995); Green (1995); Kawasaki (1993); Lesnik (1993); and Miller (1993). Such modification can be a H atom, a F atom or O—CH3 group or NH2-group at the 2' position of an individual nucleotide which is part of the nucleic acid of the present invention. Also, the nucleic acid according to the present invention can comprises at least one LNA nucleotide. In an embodiment the nucleic acid according to the present invention consists of LNA nucleotides.

In an embodiment, the nucleic acids according to the present invention may be a multipartite nucleic acid. A multipartite nucleic acid as used herein, is a nucleic acid which consists of at least two separate nucleic acid strands. These at least two nucleic acid strands form a functional unit whereby the functional unit is a ligand to a target molecule. The at least two nucleic acid strands may be derived from any of the inventive nucleic acids by either cleaving the nucleic acid molecule to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two separate nucleic acid strands are typically different from two strands being complementary and hybridising to each other although a certain extent of complementarity between said at least two separate nucleic acid strands may exist and whereby such complementarity may result in the hybridisation of said separate strands.

Finally it is also within the present invention that a fully closed, i.e. circular structure for the nucleic acids according to the present invention is realized, i.e. that the nucleic acids according to the present invention are closed in an embodiment, preferably through a covalent linkage, whereby more preferably such covalent linkage is made between the 5' end and the 3' end of the nucleic acid sequences as disclosed herein or any derivative thereof.

A possibility to determine the binding constants of the nucleic acid molecules according to the present invention is the use of surface plasmon resonance as described in example 4 which confirms the above finding that the nucleic acids according to the present invention exhibit a favourable $K_D$ value range. An appropriate measure in order to express the intensity of the binding between the individual nucleic acid molecule and the target which is in the present case hepcidin, is the so-called $K_D$ value which as such as well the method for its determination are known to the one skilled in the art.

Preferably, the $K_D$ value shown by the nucleic acids according to the present invention is below 1 µM. A $K_D$ value of about 1 µM is said to be characteristic for a non-specific binding of a nucleic acid to a target. As will be acknowledged by the ones skilled in the art, the $K_D$ value of a group of compounds such as the nucleic acids according to the present invention is within a certain range. The above-mentioned $K_D$ of about 1 µM is a preferred upper limit for the $K_D$ value. The lower limit for the $K_D$ of target binding nucleic acids can be as little as about 10 picomolar or can be higher. It is within the present invention that the $K_D$ values of individual nucleic acids binding to hepcidin is preferably within this range. Preferred ranges can be defined by choosing any first number within this range and any second number within this range. Preferred upper $K_D$ values are 250 nM and 100 nM, preferred lower $K_D$ values are 50 nM, 10 nM, 1 nM, 100 pM and 10 pM. The more preferred upper $K_D$ value is 2.5 nM, the more preferred lower $K_D$ value is 400 pM.

The nucleic acid molecules according to the present invention may have any length provided that they are still able to bind to the target molecule. It will be acknowledged by a person skilled in the art that there are preferred lengths for the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 30 to 50 nucleotides.

It is within the present invention that the nucleic acids disclosed herein comprise a moiety which preferably is a high molecular weight moiety and/or which preferably allows to modify the characteristics of the nucleic acid in terms of, among others, residence time in an animal body, preferably a human body. A particularly preferred embodiment of such modification is PEGylation and HESylation of the nucleic acids according to the present invention. As used herein PEG stands for poly(ethylene glycole) and HES for hydroxyethly starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. The modifications such as linear poly (ethylene) glycol, branched poly (ethylene) glycol, hydroxyethyl starch, a peptide, a protein, a polysaccharide, a sterol, polyoxypropylene, polyoxyamidate, poly (2-hydroxyethyl)-L-glutamine and polyethylene glycol as well as the process of modifying a nucleic acid using such modifications, are described in European patent application EP 1 306 382, the disclosure of which is herewith incorporated in its entirety by reference.

Preferably, the molecular weight of a modification consisting of or comprising a high molecular weight moiety is about from 2,000 to 250,000 Da, preferably 20,000 to 200,000 Da. In the case of PEG being such high molecular weight moiety the molecular weight is preferably 20,000 to 120,000 Da, more preferably 40,000 to 80,000 Da. In the case of HES being such high molecular weight moiety the molecular weight is preferably 20,000 to 200,000 Da, more preferably 40,000 to 150,000 Da. The process of HES modification is, e.g., described in German patent application DE 1 2004 006 249.8 the disclosure of which is herewith incorporated in its entirety by reference.

It is within the present invention that either of PEG and HES may be used as either a linear or branched form as further described in patent applications WO2005/074993 WO2003/035665 and EP1496076. Such modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule according to the invention.

The modification and preferably the PEG and/or HES moiety can be attached to the nucleic acid molecule of the present invention either directly or indirectly, preferably through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in patent applications WO2005/074993, WO2003/035665 and EP1496076.

In a preferred embodiment the linker is a biodegradable linker. The biodegradable linker allows to modify the characteristics of the nucleic acid according to the present invention in terms of, among other, residence time in an animal body, preferably in a human body, due to release of the modification from the nucleic acid according to the present invention. Usage of a biodegradable linker may allow a better control of the residence time of the nucleic acid according to the present invention. A preferred embodiment of such biodegradable linker is a biodegradable linker as described in, but not limited to, international patent applications WO2006/052790, WO2008/034122, WO2004/092191 and WO2005/099768.

It is within the present invention that the modification or modification group is a biodegradable modification, whereby the biodegradable modification can be attached to the nucleic acid molecule of the present invention either directly or indirectly, preferably through a linker. The biodegradable modification allows to modify the characteristics of the nucleic acid according to the present invention in terms of, among other, residence time in an animal body, preferably in a human body, due to release or degradation of the modification from the nucleic acid according to the present invention. Usage of biodegradable modification may allow a better control of the residence time of the nucleic acid according to the present invention. A preferred embodiment of such biodegradable modification is biodegradable as described in, but not restricted to, international patent applications WO2002/065963, WO2003/070823, WO2004/113394 and WO2000/41647, preferably in WO2000/41647, page 18, line 4 to 24.

Beside the modifications as described above, other modifications can be used to modify the characteristics of the nucleic acids according to the present invention, whereby such other modifications may be selected from the group of proteins, lipids such as cholesterol and sugar chains such as amylase, dextran etc.

Without wishing to be bound by any theory, it seems that by modifying the nucleic acids according to the present invention with high molecular weight moiety such as a polymer and more particularly one or several of the polymers disclosed herein, which are preferably physiologically acceptable, the excretion kinetic is changed. More particularly, it seems that due to the increased molecular weight of such modified inventive nucleic acids and due to the nucleic acids of the invention not being subject to metabolism particularly when in the L form, excretion from an animal body, preferably from a mammalian body and more preferably from a human body is decreased. As excretion typically occurs via the kidneys, the present inventors assume that the glomerular filtration rate of the thus modified nucleic acids is significantly reduced compared to the nucleic acids not having this kind of high molecular weight modification which results in an increase in the residence time in the animal body. In connection therewith it is particularly noteworthy that, despite such high molecular weight modification the specificity of the nucleic acids according to the present invention is not affected in a detrimental manner. Insofar, the nucleic acids according to the present invention have among others, the surprising characteristic—which normally cannot be expected from pharmaceutically active compounds—such that a pharmaceutical formulation providing for a sustained release is not necessarily required to provide for a sustained release of the nucleic acids according to the present invention. Rather the nucleic acids according to the present invention in their modified form comprising a high molecular weight moiety, can as such already be used as a sustained release-formulation as they act, due to their modification, already as if they were released from a sustained-release formulation. Insofar, the modification(s) of the nucleic acid molecules according to the present invention as disclosed herein and the thus modified nucleic acid molecules according to the present invention and any composition comprising the same may provide for a distinct, preferably controlled pharmacokinetics and biodistribution thereof. This also includes residence time in circulation and distribution to tissues. Such modifications are further described in the patent application WO2003/035665.

However, it is also within the present invention that the nucleic acids according to the present invention do not comprise any modification and particularly no high molecular weight modification such as PEGylation or HESylation. Such embodiment is particularly preferred when the nucleic acid according to the present invention shows preferential distribution to any target organ or tissue in the body or when a fast clearance of the nucleic acid according to the present invention from the body after administration is desired. Nucleic acids according to the present invention as disclosed herein with a preferential distribution profile to any target organ or tissue in the body would allow establishment of effective local concentrations in the target tissue while keeping systemic concentration of the nucleic acids low. This would allow the use of low doses which is not only beneficial from an economic point of view, but also reduces unnecessary exposure of other tissues to the nucleic acid agent, thus reducing the potential risk of side effects. Fast clearance of the nucleic acids according to the present invention from the body after administration might be desired, among others, in case of in vivo imaging or specific therapeutic dosing requirements using the nucleic acids according to the present invention or medicaments comprising the same.

The nucleic acids according to the present invention and/or the antagonists according to the present invention may be used for or in the generation or manufacture of a medicament or pharmaceutical composition. Such medicament or a pharmaceutical composition according to the present invention contains at least one of the inventive nucleic acids, optionally together with at least one further pharmaceutically active compound, whereby the inventive nucleic acid preferably acts as pharmaceutically active compound itself. Such medicament or pharmaceutical composition comprises in a preferred embodiment at least a pharmaceutically acceptable carrier. Such carrier may be, e.g., water, buffer, PBS, glucose solution, preferably a 5% glucose salt balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indication, diseases and disorders for the treatment and/or prevention of which the nucleic acids, the pharmaceutical compositions and medicaments each in accordance with or prepared in accordance with the present invention are used or are intended to be used, result from the involvement, either direct or indirect, of hepcidin in the respective pathogenetic mechanism.

As mentioned in the introductory part, hepcidin is the key signal regulating iron homeostasis whereas high levels of human hepcidin result in reduced serum iron levels and low levels result in increased serum iron levels as shown in hepcidin-deficiency and hepcidin overexpressing mouse models (Nicolas, 2001; Nicolas, 2002; Nicolas, 2003).

As also mentioned herein, binding of hepcidin to ferroportin results in immediate internalisation of ferroportin and a subsequent and long lasting decrease of serum iron (Rivera, 2005), whereby the decrease of serum iron is a cause of anemia. Anemia is defined as an absolute reduction in the quantity of haemoglobin in the circulating blood and is often a symptom of a disease manifested by low haemoglobin and not an isolated diagnosis in itself. Anemia results from a medical condition that negatively impairs production and/or lifespan of red blood cells. Additionally, anemia can be a result of blood loss.

Therefore and to understand the development of anemia, based on the underlying mechanism anemia is grouped into three etiologic categories:
 a) decreased red blood cell production,
 b) increased red blood cell destruction, and
 c) blood loss.

However, the three categories—decreased red blood cell production, increased red blood cell destruction and blood loss—are not strictly separated from each other but can occur concomitantly or independantly from each other.

In many diseases a combination of said mechanisms can lead to anemia. Thus, neutralisation of hepcidin might be beneficial in many conditions of anemia.

As the hepcidin binding nucleic acids according to the present invention interact with or bind to human hepcidin, a skilled person will understand that the hepcidin binding nucleic acids according to the present invention can be used for the treatment, prevention and/or diagnosis of any disease of humans and animals as described herein. In connection therewith, it is to be acknowledged that the nucleic acid molecules according to the present invention can be used for the treatment and prevention of any of the diseases, disorders or conditions described herein.

In the following, and without wishing to be bound by any theory, the rationale for the use of the nucleic acid molecules according to the present invention in connection with the various diseases, disorders and conditions is provided, thus rendering the claimed therapeutic, preventive and diagnostic applicability of the nucleic acid molecules according to the present invention plausible. In order to avoid any unnecessary repetition, it should be acknowledged that due to the involvement of the hepcidin—ferroportin interaction as known to a person skilled in the art and as also outlined herein said interaction may be addressed by the nucleic acid molecules according to the present invention such that the claimed therapeutic and/or preventive effect is achieved.

Accordingly, diseases and/or disorders and/or diseased conditions for the treatment and/or prevention of which the medicament according to the present invention may be used include, but are not limited to anemia, hypoferremia, pica, conditions with elevated hepcidin level, conditions with elevated iron level and/or conditions with iron overload.

Preferably anemia is selected from the group of sideroblastic anemia, hypochromic microcytic anemia, anemia caused by chronic disease and/or disorder, anemia caused by inflammation, anemia caused by genetic disorders, anemia caused by acute infections and/or anemia caused by mutation in genes of iron metabolism and/or homeostasis.

The various chronic diseases and/or disorders that can cause anemia are selected from the group of chronic inflammation, cancer, autoimmune disease and/or autoimmune disorder, chronic infection, arteriosclerosis, atherosclerosis, and cirrhosis of the liver. Insofar, anemia which may be treated by a nucleic acid of the present invention, is an anemia which is caused by or associated with any one of said various chronic diseases and/or disorders. Moreover anemia can be one which is caused by cancer treatment, preferably chemotherapy.

Subgroups of chronic inflammation are chronic kidney disease, chronic obstructive pulmonary disease, multiple sclerosis, osteoarthritis, diabetes, obesity, cerebrovascular disease, congestive heart disease, congestive heart failure, myocardial infarction, coronary artery disease, peripheral occlusive arterial disease, pancreatitis, vasculitis, whereby such chronic kidney disease comprises renal disease, chronic renal failure, chronic kidney failure and/or caused by kidney dialysis, or kidney transplantation.

Subgroups of cancer are hepatocellular carcinoma, lymphoma, multiple myeloma, head-and-neck cancer, breast cancer, colarectal cancer, nonmycloid cancers, renal cell carcinoma, non-small-cell lung cancer, tumors and brain tumors.

Subgroups of autoimmune diseases and/or disordes are rheumatoid arthritis, irritable bowel syndrome, systemic lupus erythrematosus and Chrohn's disease.

Subgroups of chronic infection are viral infections, viral illness, bacterial infections and fungal infections, whereby the viral infections comprise, but arc not limited to, hepatitis and HIV infection and the bacterial infections comprise, but are not limited to, H. pylori infection.

Anemia caused by inflammation is normocytic to microcytic, characterised by a low reticulocyte production index, total iron binding capacity (TIBC) is low or normal. Hepcidin, acute phase proteins and other markers of inflammation (for example: C-reative protein) are increased in the case of anemia caused by inflammation. Anemia caused by inflammation is also referred to as anemia by inflammation.

The various genetic disorders that can cause anemia are selected from the group of the Castleman disease, Schnitzler's syndrome, iron refractory iron deficiency anemia (matriptase-2 (TMPRSS6) mutation, atransferrinemia, congenital dyserythropoietic anemia and hemoglobinopathies The various acute infection that can cause anemia are selected from the group of viral infection, bacterial infection and fungal infection, whereby viral infection, bacterial infection and fungal infection individually or in combination with each other can lead to sepsis.

The term "conditions with elevated hepcidin level" refers to a condition in a mammal, preferably a human, wherein the level of hepcidin in the body is elevated compared to the normal level of hepcidin for such a mammal, such as an elevated hepcidin scrum level compared to the normal hepcidin serum level for the mammal (approximately 120 ngl/mL in case of a human being). Elevated serum hepcidin levels can, among others, be determined by enzyme-linked immunoassay (commercially available kit by DRG Diagonstics, Marburg, Germany).

Accordingly, the patients for which the medicament according to the present invention may preferably be used include, but are not limited to patients which are treated with erythropoietin and other red cell stimulating therapies and preferably show a hypo-responsiveness to erythropoietin, whereby more preferably the patients have a chronic kidney disease or suffering from cancer, whereby cancer is selected from the group of hepatocellular carcinoma, lymphoma, multiple myeloma, head-and-neck cancer, breast cancer, colarectal cancer, nonmyeloid cancers, renal cell carcinoma, non-small-cell lung cancer, tumors and brain tumors.

In a further embodiment, the medicament according to the invention comprises a further pharmaceutically active compound. Such further pharmaceutically active compound is preferably one that can modulate the activity, concentration or expression of hepcidin or ferroportin. Such compound is preferably a pro-hepcidin cleaving protease inhibitor, a pro-hepcidin antibody, a ferroportin-antagonist such as, e.g. a ferroportin-antibody, a JAK2 inhibitor, GDF15, a BMP modulator, a soluble haemojuvelin or TGF-beta inhibitor.

Other further pharmaceutically active compounds which may be used together with or contained in the medicament comprising a nucleic acid according to the invention are those that are known and/or used for treating anemia and/or inflammatory conditions, whereby the treatment of the inflammatory conditions positively influences anemia. Such pharmaceutically active compounds are selected from the group comprising iron supplements, vitamin supplements, red cell production stimulators, antibiotics, anti-inflammatory biologies, suppressors of the immune system, anti-thrombolytics, statins, vasopressors and inotropic compounds.

Non-limiting examples of iron supplements are ferrous sulphate, ferrous gluconate, iron dextran, sodium ferric gluconate, ferric carboxymaltose, iron-hydroxide polymaltose, iron fumarat, iron saccharose and iron-hydroxide sucrose.

Non-limiting examples of vitamin supplements are vitamin C, folic acid, vitamin B12, vitamin B6 and vitamin D Non-limiting examples of red cell production stimulators are erythropoietin, Epoctin, Darbepoetin, CERA, HIF prolylhydroxylase inhibitors (for example FG-2216 and FG-4592) and other erythropoiesis stimulating agents.

Non-limiting examples of antibiotics are aminoglycosides, beta-lactam antibiotics, eptide antibiotics, gryase inhibitors, lincosamide, macrolide antibiotics, nitroimidazole derivates, polypeptide antibiotics, sulfonamides, tetracycline and trimethoprim.

Non-limiting examples of anti-inflammatory biologies are
a) IL-6-receptor antagonists such as, e.g., Tocilizumab or Atlizumab,
b) TNF-antagonists such as, e.g., Etanercept, Infliximab, Adalimumab, Certolizumab,
c) IL-1 receptor antagonists such as, e.g., Anakinra, and
d) CD20 binding molecules such as, e.g., Rituximab and Ibritumab.

Non-limiting examples of suppressors of the immune system are azathioprin, brequinar, calcineurin inhibitors, chlorambucil, cyclosporin A, deoxyspergualin, leflunomide, methotrexate, mizoribin, mycophenolate mofetil, rapamycin, tacrolimus and thalidomide.

Non-limiting examples of anti-inflammatory agents are PDE4 inhibitors such as roflumilast and corticosteroids such as prednisolone, methylprednisolone, hydrocortisone, dexamethason, triamcinolone, betamethasone, effervescent, budesonide, ciclesonide and fluticasone.

Non-limiting of anti-thrombolytics are activated human protein C such as Drotrecogin alfa.

Non-limiting examples of statins are Alorvastatin, Cerivastatin, Fluvastatin, Lovastatin, Mevastatin, Pitavastatin, Pravastatin, Rosuvastatin and Simvastatin.

Non-limiting examples of vasopressors and/or inotropic compounds are noradrenalin, vasopressin and dobutamin.

In addition to situations with elevated hepcidin plasma level, the nucleic molecules according to the present invention can also be used to antagonize hepcidin in patients with elevated iron level and/or conditions with iron overload and non-elevated hepcidin plasma level. The treatment of such patients with the nucleic molecules according to the present invention is preferably done in order to decrease cellular iron concentration, whereby the treatment is preferably in combination with iron chelating compounds. The neutralisation of physiological hepcidin by the nucleic acid according to the present invention protects ferroportin expression and thereby supports a further iron release from intracellular stores. Ferroportin protection in combination with iron chelating compounds eliminates iron via the urin and reduces the of whole body iron content.

In medical art, iron overload indicates accumulation of iron in the body due to any cause. Characteric for iron overload is a total body content of >5 mg iron in case of man. Iron overload is also referred to as hemochromatosis.

The term "conditions with iron overload" refers to a condition in a mammal, preferably a human, wherein the level of iron in the mammalian body is elevated compared to the normal level of iron for such a mammal, such as an elevated iron serum level compared to the normal iron serum level for the mammal (approximately 20 µmol/L in case of a human being) or an increased level of iron in the liver of the mammal as compared to the normal level of iron in the liver in the mammal. Elevated serum iron levels can be determined by direct measurement of serum iron using, among others, a colorimetric assay, by the standard transferrin saturation assay (which reveals how much iron is bound to the protein that carries iron in the blood), or by the standard serum ferritin assay (for example: Ferritin Blood Test ELISA kit form Cal-biotech, USA). For example, transferrin saturation levels of 45% or higher are usually indicative of abnormally high levels of iron in the serum. Elevated iron levels in the liver can, among others, be determined measuring the iron content of the liver from tissue obtained by a liver biopsy or by imaging technique such as MRI and/or SQUID. The degree of iron levels in other tissues such as e.g. brain, heart may also be estimated using these and other imaging techniques.

Subgroups of iron overload are transfusional iron overload, iron intoxication, pulmonary hemosiderosis, osteopenia, insulin resistense, African iron overload, Hallervordan Spatz disease, hyperferritinemia, ceruloplasmin deficiency, neonatal hemochromatosis and red blood cell disorders comprising thalassemia, alpha thalassemia, thalassemia intermedia, sickle cell disease and myelodyplastic syndrome.

Patients suffering from other disorders/disease associated with elevated iron level should also benefit from a therapy with the nucleic molecules according to the present invention, preferably in combination with an iron chelating compound. Accordingly, disease and/or disorders and/or diseased conditions for the treatment and/or prevention of which the medicament according to the present invention may be used include, but are not limited to disease with elevated iron level, comprising ataxia, Friedrich's ataxia, age-related macular degeneration, age-related cataract, age-related retinal diseases and neurodegenrative disease, whereby such neurodegenrative disease comprises Alzheimer's disease, Parkinson's disease, pantothenate kinase-associated neurodegeneration, restless leg syndrom and Huntington's disease.

In a further embodiment, the medicament accodirding to the invention comprises a further pharmaceutically active compound which is preferably one that can bind iron and removes iron from tissue or from circulation of an mammalian body and a human body in particular. Such pharmaceutically active compound is preferably selected from the group of iron chelating compounds. Combination of such a compound with a nucleic acid molecule according to the present invention will further reduce the physiological hepcidin concentration and thereby reduce cellular iron load.

Non-limiting examples iron chelating compounds are curcumin, deferoxamine, deferasirox and deferiprone.

Finally, the further pharmaceutically active agent may be a modulator of the iron metabolism and/or iron homoestasis. Alternatively, or additionally, such further pharmaceutically active agent is a further, preferably a second species of the nucleic acids according to the present invention. Alternatively, the medicament comprises at least one more nucleic acid which binds to a target molecule different from hepcidin or exhibits a function which is different from the one of the nucleic acids according to the present invention. Preferably such at least one more nucleic acid exhibits a function similar or identical to the one of the one or several of the further pharmaceutically active compound(s) disclosed herein.

It is within the present invention that the medicament comprising a nucleic acid according to the invention, also referred to herein as the medicament of the (present) invention, is alternatively or additionally used, in principle, for the prevention of any of the disease disclosed in connection with the use of the medicament for the treatment of said diseases. Respective markers therefore, i.e. for the respective diseases are known to the ones skilled in the art. Preferably, the respective marker is hepcidin.

In one embodiment of the medicament of the present invention, such medicament is for use in combination with other treatments for any of the diseases disclosed herein, particularly those for which the medicament of the present invention is to be used.

"Combination therapy" or "co-therapy" as preferably used herein, includes the administration of a medicament of the invention and at least a second agent as part of a treatment regimen intended to provide a beneficial effect from the co-action of these therapeutic agents, i. e. the medicament of the present invention and said second agent. Administration of these therapeutic agents as or in combination typically is carried out over a defined time period (usually minutes, hours, days or weeks depending upon the combination selected).

"Combination therapy" may, but generally is not, intended to encompass the administration of two or more of therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of a therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example. a first therapeutic agent of a specific combination of therapeutically effective agents may be administered by injection while the or an other therapeutic agent of the combination may be administered topically.

Alternatively, for example, all therapeutic agents may be administered topically or all therapeutic agents may be administered by injection. The sequence in which the therapeutic agents are administered is not critical unless noted otherwise. Where the combination therapy further comprises a non-drug treatment, the non-drug treatment may be conducted at any suitable time as long as a beneficial effect from the combination of the therapeutic agents and the non-drug treatment is achieved. For example, in appropriate cases, the beneficial effect may still be achieved when the non-drug treatment is temporally stayed, perhaps by days or even weeks whereas the therapeutic agents are still administered.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, subcutaneous, per orum, intranasal, intratracheal and pulmonary with preference given to the route of administration that is the least invasive while ensuring efficiancy.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained and which are well known to the ordinary skill in the art.

Furthermore, preferred medicaments of the present invention can be administered by the intranasal route via topical use of suitable intranasal vehicles, inhalants, or via transdermal routes, using those forms of transdermal skin patches well known to those of ordinary skill in that art. To be administered in the form of a transdermal delivery system, the dosage administration will typically be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

The medicament of the present invention will generally comprise an amount of the active component(s) effective for the therapy, including, but not limited to, a nucleic acid molecule of the present invention, preferably dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable vehicle. Such vehicle can be any vehicle or any binder used and/or known in the art. More particularly such binder or vehicle is any binder or vehicle as discussed in connection with the manufacture of the medicament disclosed herein. In a further embodiment, the pharmaceutical composition comprises a further pharmaceutically active agent.

The preparation of a medicament and a pharmaceutical composition, respectively, is known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via a microdevice, microparticles or a sponge.

In this context, the quantity of active ingredient and volume of composition to be administered depends on the individual or the subject to be treated. Specific amounts of active compound required for administration depend on the judgment of the practitioner and are peculiar to each individual.

A minimal volume of a medicament required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component, i. e. a nucleic acid molecule according to the present invention and/or any further pharmaceutically active agent, also referred to herein as therapeutic agent(s) or active compound(s) in their entirety, can be combined with an oral, non-toxic, pharmaceutically acceptable and preferably inert carrier such as ethanol, glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starchy methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The medicament according to the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament according to the invention may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form an injectable solution or suspension. Additionally, solid forms suitable for dissolving in liquid prior to injection can be formulated.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to form a lipid layer encapsulating the drug, which is well known to the ordinary person skilled in the art. For example, the nucleic acid molecules according to the invention can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues Furthermore, the medicaments and nucleic acid molecules, respectively, of the present invention may be coupled to a class of biodegradable polymers useful in achieving controlled release of a drug, for example, polylactic acid, polyepsilon capro lactone, polyhydroxy butyric acid, polyorthoesters, polyacetals, polydihydropyrans, polycyanoacrylatcs and cross-linked or amphipathic block copolymers of hydrogels.

If desired, the pharmaceutical composition and medicament, respectively, to be administered may also contain amounts, typically minor amounts, of non-toxic auxiliary substances such as wetting or emulsifying agents, pH buffering agents, and other substances such as for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular nucleic acid according to the invention or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 500 µM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is in need of such treatment, whereby the method comprises the administration of a pharmaceutically effective amount of at least one of the nucleic acids according to the present invention. In an embodiment, the subject suffers from a disease or is at risk to develop such disease, whereby the disease is any one of those disclosed herein, particularly any one of those diseases disclosed in connection with the use of any of the nucleic acids according to the present invention for the manufacture of a medicament.

It is to be understood that the nucleic acid as well as the antagonists according to the present invention can be used not only as a medicament or for the manufacture of a medicament, but also for cosmetic purposes, particularly with regard to the involvement of hepcidin in inflamed regional skin lesions. Therefore, a further condition or disease for the treatment or prevention of which the nucleic acid, the medicament and/or the pharmaceutical composition according to the present invention can be used, is inflamed regional skin lesions.

As preferably used herein a diagnostic or diagostic agent or diagnostic means is suitable to detect, either directly or indirectly, hepcidin, preferably hepcidin as described herein and more preferably hepcidin as described herein in connection with the various disorders and diseases described herein. The diagnostic is suitable for the detection and/or follow-up of any of the disorders and diseases, respectively, described herein. Such detection is possible through the binding of the nucleic acids according to the present invention to hepcidin. Such binding can either directly or indirectly be detected. The respective methods and means are known to a person skilled in the art. Among others, the nucleic acids according to the present invention may comprise a label which allows the detection of the nucleic acids according to the present invention, preferably the nucleic acid being bound to hepcidin. Such a label is preferably selected from the group comprising radioactive, enzymatic and fluorescent labels. In principle, all known assays developed for antibodies can be adopted and adapted for the nucleic acids according to the present invention whereby the target-binding antibody is substituted to a target-binding nucleic acid of the present invention. In antibody-assays using unlabeled target-binding antibodies the detection is preferably done by a secondary antibody which is modified with radioactive, enzymatic and fluorescent labels and which binds to the target-binding antibody at the Fc-fragment of the target-binding antibody. In case of a nucleic acid, preferably a nucleic acid according to the present invention, the nucleic acid is modified with such a label, whereby preferably such a label is selected from the group comprising biotin, Cy-3 and Cy-5, and such label is detected by an antibody directed against such label. e.g. an anti-biotin antibody, an anti-Cy3 antibody or an anti-Cy5 antibody, or—in the case the label is biotin—the label is detected by streptavidin or avidin which naturally binds to biotin. Such antibody, streptavidin or avidin in turn is preferably modified with a respective label, e.g. a radioactive, enzymatic or fluorescent label like an secondary antibody allowing its detection.

In a further embodiment the nucleic acid molecules according to the invention are detected or analysed by a second detection means, wherein the second detection means is a molecular beacon. The methodology of molecular beacon is known to persons skilled in the art.

In brief, nucleic acids probes which are also referred to as molecular beacons, are a reverse complement to the nucleic acids to be detected and hybridise because of this to a part or the entirety of the nucleic acid to be detected. Upon binding to the nucleic acid to be detected the fluorophoric groups of the molecular beacon are separated which results in a change of the fluorescence signal, preferably a change in intensity. This change correlates with the amount of nucleic acids to be detected.

It will be acknowledged that the detection of hepcidin using the nucleic acids according to the present invention will particularly allow the detection of hepcidin as defined herein.

In connection with the detection of hepcidin a preferred method comprises the following steps:
(a) providing a sample which is to be tested for the presence of hepcidin,
(b) providing a nucleic acid according to the present invention,
(c) reacting the sample with the nucleic acid, preferably in a reaction vessel
whereby step (a) can be performed prior to step (b), or step (b) can be performed prior to step (a).

In a preferred embodiment a further step d) is provided, which consists in detecting whether or not the nucleic acid has reacted with hepcidin. Preferably, the nucleic acid of step b) is immobilised to a surface. The surface may be the surface of a reaction vessel such as a reaction tube, a well of a plate, or the surface of a device contained in such reaction vessel such as, for example, a bead. The immobilisation of the nucleic acid to the surface can be made by any means known to the ones skilled in the art including, but not limited to, non-covalent or covalent linkages. Preferably, the linkage is established via a covalent chemical bond between the surface and the nucleic acid. However, it is also within the present invention that the nucleic acid is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, spiegelmers, and nucleic acids which are at least partially complementary to the nucleic acid. In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method for the dectection of hepcidin is the formation of an immobilised complex of hepcidin and the nucleic acid, whereby more preferably said complex is detected. It is within an embodiment that the hepcidin contained in or as set free from the complex is detected.

A respective detection means which is suitable for the detection of said hepcidin is any detection means which is specific for hepcidin. A particularly preferred detection means is a detection means which is selected from the group comprising nucleic acids, polypeptides, proteins and antibodies.

The method for the detection of hepcidin according to the invention also comprises that the sample is removed from the reaction vessel which has preferably been used to perform step c).

The method of the present invention comprises in a further embodiment also the step of immobilising an interaction partner of hepcidin on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid according to the present invention, whereby such nucleic acid may be labelled or non-labelled. In case such nucleic acid is labelled the nucleic acid comprises a detection label. Such detection label can be directly or indirectly detected. Such detection may also involve the use of a second detection means which is, preferably, also selected from the group comprising nucleic acids, polypeptides, proteins and antibodies in the various embodiments described herein. Such second detection means is preferably specific for the nucleic acid according to the present invention and in case the nucleic acid according to the present invention comprises a detection label, such second detection means is specific for the detection label. In a more preferred embodiment, the second detection means is a molecular beacon. It is also within the present invention that the second detection means or comprises in a preferred embodiment a detection label. The detection label, irrespective of whether it is comprised by the nucleic acid according to the invention or the second detection means, is preferably selected from the group comprising biotin, a bromo-desoxyuridine label, a digoxigenin label, a fluorescence label, a UV-label, a radiolabel, and a chelator molecule. Particularly preferred combinations are as follows:

the detection label attached to the nucleic acid according to the present invention is biotin and the second detection means is an antibody directed against biotin, or wherein the detection label attached to the nucleic acid according to the present invention is biotin and the second detection means is an avidin or an avidin carrrying molecule, or wherein the detection label attached to the nucleic acid according to the present invention is biotin and the second detection means is a streptavidin or a stretavidin carrying molecule, or wherein the detection label attached to the nucleic acid according to the present invention is biotin and the second detection means is a neutravidin or a neutravidin carrying molecule, or wherein the detection label attached to the nucleic acid according to the present invention is a bromo-desoxyuridine and the second detection means is an antibody directed against bromo-desoxyuridine, or wherein the detection label attached to the nucleic acid according to the present invention is digoxigenin and the second detection means is an antibody directed against digoxigenin, or wherein the detection label attached to the nucleic acid according to the present invention is a chelator and the second detection means is a radio-nuclide, whereby it is preferred that said detection label is attached to the nucleic acid according to the present invention.

It is to be acknowledged that these kinds of combination are also applicable to the embodiment where the nucleic acid according to the invention is attached to the surface. In such embodiment it is preferred that the detection label is attached to the second detection means, i.e. preferably the interaction partner.

Finally, it is also within the present invention that the second detection means is detected using a third detection means, preferably the third detection means is an enzyme, more preferably an enzyme showing an enzymatic reaction upon reaction with the second detection means. Alternatively, the third detection means is a means for detecting radiation, more preferably radiation emitted by a radio-nuclide which is attached to either the nucleic acid according to the present invention or the second detection means, preferably the second detection means. Preferably, the third detection means is specifically detecting and/or interacting with the second detection means.

Also, in the embodiment where an interaction partner of hepcidin is immobilised on a surface and the nucleic acid according to the present invention is preferably added to the complex formed between the interaction partner and the hepcidin, the sample can be removed from the reaction, more preferably from the reaction vessel where step c) and/or d) are preformed.

In an embodiment the nucleic acid according to the present invention comprises a fluorescence moiety and whereby the fluorescence of the fluorescence moiety is different upon complex formation between the nucleic acid and hepcidin on the one hand and the nucleic acid and free hepcidin on the other.

In a further embodiment the nucleic acid as used in the method for detecting hepcidin in accordance with the present invention is a derivative of the nucleic acid according to the present invention, whereby the derivative of the nucleic acid comprises at least one fluorescent derivative of adenosine replacing adenosine. In a preferred embodiment the fluorescent derivative of adenosine is ethenoadenosine.

In a further embodiment the complex consisting of the derivative of the nucleic acid according to the present invention and the hepcidin is detected using fluorescence.

In an embodiment of the method a signal is created in step (c) or step (d) and preferably the signal is correlated with the concentration of hepcidin in the sample.

In a preferred embodiment, the method may be performed in 96-well plates, where components are immobilized in the reaction vessels as described above and the wells acting as reaction vessels.

The inventive nucleic acid may further be used as starting material for drug design. Basically there are two possible approaches. One approach is the screening of compound libraries whereby such compound libraries are preferably low molecular weight compound libraries. In an embodiment, the screening is a high throughput screening. Preferably, high throughput screening is the fast, efficient, trial-and-error evaluation of compounds in a target-based assay. In best case the assay format of the target-based assayis based on colorimetric measurement. Libraries as used in connection therewith are known to the one skilled in the art.

Alternatively, the nucleic acid according to the present invention may be used for rational design of drugs. Preferably, rational drug design is the design of a pharmaceutical lead structure. Starting from the 3-dimensional structure of the target which is typically identified by methods such as X-ray crystallography or nuclear magnetic resonance spectroscopy, computer programs are used to search through databases containing structures of many different chemical compounds. The selection is done by a computer, the identified compounds can subsequently be tested in the laboratory.

The rational design of drugs may start from any of the nucleic acid according to the present invention and involves a structure, preferably a three dimensional structure, which is similar to the structure of the inventive nucleic acids or identical to the parts of the structure of the inventive nucleic acids to mediating the binding of the nucleic acid to the target, i.e. hepcidin. In either a further step or as an alternative step in the rational design of drugs the preferably three dimensional structure of those parts of the nucleic acids binding to the hepcidin are mimicked by chemical groups which are different from nucleotides and nucleic acids. By this mimicry a compound different from the nucleic acids according to the invention can be designed. Such compound is preferably a small molecule or a peptide.

In case of screening of compound libraries, such as by using a competitive assay which is known to the ones skilled in the arts, appropriate hepcidin analogues, hepcidin agonists or hepcidin antagonists may be found. Such competitive assays may be set up as follows. The inventive nucleic acid, preferably a spiegelmer which is a target binding L-nucleic acid, is coupled to a solid phase. In order to identify hepcidin analogues labelled hepcidin may be added to the assay. A potential analogue would compete with the hepcidin molecules binding to the spiegelmer which would go along with a decrease in the signal obtained by the respective label.

Screening for agonists or antagonists may involve the use of a cell culture assay as known to the ones skilled in the art.

The kit according to the present invention may comprise at least one or several of the inventive nucleic acids. Additionally, the kit may comprise at least one or several positive or negative controls. A positive control may, for example, be hepcidin, particularly the one which is bound by the inventive nucleic acid, whereby, preferably, the positive control is present in either a liquid or lyophilised form. A negative control may, e.g., be a peptide which is defined in terms of biophysical properties similar to hepcidin, but which is not recognized by the inventive nucleic acids. Furthermore, said kit may further comprise one or several buffers. The various ingredients may be contained in the kit in dried or lyophilised form or may be dissolved or dispersed in a liquid. The kit may also further comprise one or several containers which in turn may contain one or several of the ingredients of the kit. In a still further embodiment, the kit further comprises instructions or an instruction leaflet which provides to the user information on how to use the kit and its various ingredients.

The quantification of the nucleic acid according to the present invention in several humours, tissues and organs of a human or non-human body is essential for the assessment of its pharmacokinetic and pharmacodynamic profile the nucleic acid according to the present invention. For such purpose, any of the detection methods disclosed herein or known to a person skilled in the art using the nucleic acid according to the present invention may be used. In a further aspect of the present invention a sandwich hybridisation assay for the detection of the nucleic acid according to the present invention is provided. In connection with such sandwich hybridisation assay a capture probe and a detection probe are used. The capture probe is essentially complementary to a first part of a nucleic acid according to the present invention and the detection probe is essentially complementary to a second part of the nucleic acid according to the present invention. Both, capture and detection probe, can be formed by DNA nucleotides, modified DNA nucleotides, modified RNA nucleotides, RNA nucleotides, LNA nucleotides and/or PNA nucleotides.

Hence, the capture probe comprises a stretch of nucleotides which is essentially complementary to the 5'-end of a nucleic acid according to the present invention, and the detection probe comprises a stretch of nucleotides which is essentially complementary to the 3'-end of the nucleic acid according to the present invention. In this case the capture probe is immobilised to a surface or matrix via its 5'-end whereby the capture probe can be immobilised directly at its 5'-end or via a linker between its 5'-end and the surface or matrix. However, in principle the linker can be linked to each nucleotide of the capture probe. The linker can be formed by hydrophilic linkers or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides as known to a person skilled in the art.

Alternatively, the capture probe may comprise a stretch of nucleotides essentially complementary to the 3'-end of a nucleic acid according to the present invention and the detection probe comprise a stretch of nucleotides essentially complementary to the 5'-end of the nucleic acid according to the present invention. In this case the capture probe is immobilised to a surface or matrix via its 3'-end whereby the capture probe can be immobilised directly at its 3'-end or via a linker between its 3'-end and the surface or matrix. However, in principle, the linker can be linked to each nucleotide of the stretch of nucleotides that is essentially complementary to the nucleic acid according to the present invention. The linker can be formed by hydrophilic linkers or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides as known to a person skilled in the art.

The number of nucleotides of the capture and detection probe, respectively, that may hybridise to the nucleic acid according to the present invention is variable and can be dependent on the number of nucleotides of the capture probe and/or the detection probe and/or the nucleic acid according to the present invention itself. The total number of nucleotides of the capture probe and of the detection probe that may hybridise to the nucleic acid according to the present invention should be maximal the number of nucleotides that are comprised by the nucleic acid according to the present invention. A minimal number of nucleotides of typically 2 to 10 nucleotides independently on each of of the detection probe and capture probe should allow hybridisation to the 5'-end or 3'-end, respectively, of the nucleic acid according to the present invention.

Moreover the detection probe preferably carries a marker molecule or a label that can be detected as previously described herein. The label or marker molecule can in principle be linked to each nucleotide of the detection probe or each moiety of the detection probe. Preferably, the label or marker is located at the 5'-end or 3'-end of the detection probe, whereby between the nucleotides within the detection probe that are complementary to the nucleic acid according to the present invention, and the label a linker can be inserted. The linker can be formed by hydrophilic linkers or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides as known to a person skilled in the art.

In an embodiment of the method for detecting hepcidin, the detection of the nucleic acid according to the present invention can be carried out as follows:

The nucleic acid according to the present invention is hybridised with one of its ends to a capture probe and with the other end to a detection probe. Afterwards, unbound detection probe, i.e. detection probe that is not bound to the nucleic acid according to the invention, is removed by, e. g., one or several washing steps. The amount of bound detection probe which preferably carries a label or marker molecule, can be measured subsequently as, for example, outlined in more detail in WO/2008/052774 which is incorporated herein by reference.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ.ID. Nos., the chemical nature of the nucleic acid molecules according to the present invention and the target molecules hepcidin as used herein, the actual sequence thereof and the internal reference number is summarized in the following table.

| Seq.-ID | RNA/Peptide | Sequence | Internal Reference |
|---|---|---|---|
| 1 | L-peptide | DTHFPICIFCCGCCHRSKCGMCCKT | Human hepcidin, human hepcidin-25 |
| 2 | L-peptide | DTHFPICIFCCGCCHRSKCGMCCKT | Hepcidin-25 of *Macaca mulatta* (rhesus monkey) |
| 3 | L-peptide | DTHFPICIFCCGCCHRSKCGMCCKT | Hepcidin-25 of *Macaca fascularis* (cynomolgus monkey) |
| 4 | L-peptide | DTHFPICIFCCGCCRKAICGMCCKT | Hepcidin-25 of *Sus scrofa* (pig) |
| 5 | L-peptide | DTNFPICIFCCKCCNNSQCGICCKT | Hepcdin-25 of *Mus musculus* (mouse) |
| 6 | L-peptide | DTNFPICLFCCKCCKNSSCGLCCIT | Hepcidin-25 of *Rattus norvegicus* (rat) |
| 7 | D-peptide | DTHFPICIFCCGCCHRSKCGMCCKT-Biotin | Biotinylated human D-hepcidin-25 |
| 8 | L-peptide | ICIFCCGCCHRSKCGMCCKT | human hepcidin-20 |
| 9 | L-peptide | FPICIFCCGCCHRSKCGMCCKT | human hepcidin-22 |
| 10 | D-RNA | GCACUCGUAAAGUAGAGGGACCCAGUCCGGCGUGAUAGUGCCGAGUGC | 223-C5-001 |
| 11 | D-RNA | GCACUUGUAAAGUAGAGGGACCCAGUCCGGCGUGAUAGUGCCGAGUGC | 223-B5-001 |
| 12 | D-RNA | GCAUUCGUAAAGUAGAGGGACCCAGUCCGGCGUGAUAGUGCCGAGUGC | 223-A5-001 |
| 13 | D-RNA | GCACUCGUAAAGUAGAGGGACCUAGUCCGGCGUGAUAGUGCCGGGUGC | 223-A3-001 |
| 14 | D-RNA | GCACUCGUAAAGUAGAGGGACCUAGUCCGGCGUGAUAGUGCCGAGUGC | 223-F5-001 |
| 15 | D-RNA | GCACUCGUAAAGUAGAGGGACUCAGUCCGGCGUGAUAGUGCCGAGUGC | 223-G4-001 |
| 16 | D-RNA | GCACUCGUAAAGUAGAGGGAUACAGUCCGGCGUGAUAGUGACGAGUGC | 223-A4-001 |
| 17 | D-RNA | CGUGUGUAAAGUAGAGGCAGGUAAUCUGCGGAGUGUUAGUUCCACACG | 229-C2-001 |
| 18 | D-RNA | CGCGUGUAAAGUAGAGGCAGGUAAUCUGCGGAGUGUUAGUUCCACACG | 229-B4-001 |
| 19 | D-RNA | CGUGUGUAAAGUAGAGGCAGGCAAUCUGCGGAGUGUUAGUUCCACACG | 229-E2-001 |
| 20 | D-RNA | CGUGUGUAAAGUAGAGGACAAUUGUCGGCGUGAUAGUGCCACACG | 229-B1-001 |
| 21 | D-RNA | GCUGUGUAAAGUAGAGGACAAUUGUCGGCGUGAUAGUGCCACAGC | 229-B1-002 |
| 22 | D-RNA | CGUGUGUAAAGUAGAGGACAAUAGUCGGCGUGAGAGUGCCACACG | 229-G1-001 |
| 23 | D-RNA | CGUGAAAAGUAGAAACUUGUCGAAAGCAAGUAGCGUGAUAGUGCCACG | 229-C4-001 |
| 24 | D-RNA | CGUGCUGGCGUGAUAGUGCUCCAGGUUCUGGAUAAAGUAGAGAGCACG | 229-D1-001 |
| 25 | D-RNA | CGUGCGAAGGAGUGAUAAGUGUUUCUGACUUUCUUCCAGACUCCCACG | 229-E1-001 |
| 26 | D-RNA | CACUCGUAAAGUAGAGGGACCCAGUCCGGCGUGAUAGUGCCGAGUG | 223-C5-002 |
| 27 | D-RNA | CGCGCGUAAAGUAGAGGGACCCAGUCCGGCGUGAUAGUGCCGCGCG | 223-C5-006 |
| 28 | D-RNA | GCGCGUAAAGUAGAGGGACCCAGUCCGGCGUGAUAGUGCCGCGC | 223-C5-007 |

-continued

| Seq.-ID | RNA/Peptide | Sequence | Internal Reference |
|---|---|---|---|
| 29 | L-RNA | GCACUCGUAAAGUAGAGGGACCCAGUCCGGCGUGAUAG UGCCGAGUGC | 223-C5-001 |
| 30 | L-RNA | GCACUUGUAAAGUAGAGGGACCCAGUCCGGCGUGAUA GUGCCGAGUGC | 223-B5-001 |
| 31 | L-RNA | GCAUUCGUAAAGUAGAGGGACCCAGUCCGGCGUGAUA GUGCCGAGUGC | 223-A5-001 |
| 32 | L-RNA | GCACUCGUAAAGUAGAGGGACCUAGUCCGGCGUGAUA GUGCCGGGUGC | 223-A3-001 |
| 33 | L-RNA | GCACUCGUAAAGUAGAGGGACCUAGUCCGGCGUGAUA GUGCCGAGUGC | 223-F5-001 |
| 34 | L-RNA | GCACUCGUAAAGUAGAGGGACUCAGUCCGGCGUGAUA GUGCCGAGUGC | 223-G4-001 |
| 35 | L-RNA | GCACUCGUAAAGUAGAGGGAUACAGUCCGGCGUGAUA GUGACGAGUGC | 223-A4-001 |
| 36 | L-RNA | CGUGUGUAAAGUAGAGGCAGGUAAUCUGCGGAGUGUU AGUUCCACACG | 229-C2-001 |
| 37 | L-RNA | CGCGUGUAAAGUAGAGGCAGGUAAUCUGCGGAGUGUU AGUUCCACACG | 229-B4-001 |
| 38 | L-RNA | CGUGUGUAAAGUAGAGGCAGGCAAUCUGCGGAGUGUU AGUUCCACACG | 229-E2-001 |
| 39 | L-RNA | CGUGUGUAAAGUAGAGGACAAUUGUCGGCGUGAUAGU GCCACACG | 229-B1-001 |
| 40 | L-RNA | GCUGUGUAAAGUAGAGGACAAUUGUCGGCGUGAUAGU GCCACAGC | 229-B1-002 |
| 41 | L-RNA | CGUGUGUAAAGUAGAGGACAAUAGUCGGCGUGAGAGU GCCACACG | 229-G1-001 |
| 42 | L-RNA | CGUGAAAAGUAGAAACUUGUCGAAAGCAAGUAGCGUG AUAGUGCCACG | 229-C4-001 |
| 43 | L-RNA | CGUGCUGGCGUGAUAGUGCUCCAGGUUCUGGAUAAAG UAGAGAGCACG | 229-D1-001 |
| 44 | L-RNA | CGUGCGAAGGAGUGAUAAGUGUUUCUGACUUUCUUCC AGACUCCCACG | 229-E1-001 |
| 45 | L-RNA | CACUCGUAAAGUAGAGGGACCCAGUCCGGCGUGAUAGU GCCGAGUG | 223-C5-002 |
| 46 | L-RNA | CGCGCGUAAAGUAGAGGGACCCAGUCCGGCGUGAUAGU GCCGCGCG | 223-C5-006 |
| 47 | L-RNA | GCGCGUAAAGUAGAGGGACCCAGUCCGGCGUGAUAGU GCCGCGC | 223-C5-007 |
| 48 | L-RNA | 5'-40-kDa-PEG-GCACUCGUAAAGUAGAGGGACCCAGUCCGGCGUGAUAGU GCCGAGUGC | 223-C5-001-5'-PEG |
| 49 | D-RNA | AGGCGUAAAGUAGAGGGCUGAGCCCGGCGUGUUAGUGC CGCCU | 238-A1-001 |
| 50 | D-RNA | AGGCGUAAAGUAGAGGGACGUAGUCCGGCGUGAUAGUGC CGCCU | 238-E2-001 |
| 51 | D-RNA | CGUGUGUAAAGUAGAGGCAGAUAAUCUGCGGAGUGUUA GUUCCACACG | 237-A7-001 |
| 52 | D-RNA | CGUGAAAAGUAGAAACUUGUCGAAAGCAAGCAGCGUGAU AGUGCCACG | 236-G2-001 |
| 53 | D-RNA | CGUGAAAAGUUGAAAUUUGUUGGAAUCAAGCAGGGAUA UAGUGCCACG | 236-D1-001 |

| Seq.-ID | RNA/Peptide | Sequence | Internal Reference |
|---|---|---|---|
| 54 | D-RNA | AGCGUGUCGUAUGGGAUAAGUAAAUGAGGAGUUGGAGGAAGGGUGCGCU | 238-D2-001 |
| 55 | D-RNA | AGCGUGUCGUAUGGGAUUAAGUAAAUGAGGAGUUGGAGGAAGGGCAUGCU | 238-D4-001 |
| 64 | D-RNA | AGGCUUGGGCGGCCGGGGGACACCAUAUACAGACUACUAUACGAGCCU | 238-A4-001 |
| 65 | D-RNA | AGACUUGGGCAGCCGGGGGACACCAUAUACAGACUACGAUACGAGUCU | 238-E1-001 |
| 66 | D-RNA | CGGGCGCCAUAGACCGUUAUUAAGCACUGUAACUACCGAACCGCGCCCG | 237-A5-001 |
| 67 | D-RNA | CGGGCGCCAUAGACCGUUAACUACAUAACUACCGAACCGUGCCCG | 237-C5-001 |
| 68 | D-RNA | CGGGCGCUACCGAACCCACUAAAACCAGUGCAUAGACCGCGCCCG | 236-F2-001 |
| 69 | D-RNA | CGGGCGCUACCGAACCGUCACGAAGACCAUAGACCGCGCCG | 236-G4-001 |
| 70 | D-RNA | CGAGCGCAACCGAACCUCUACCCAGACAUAGACCGCGCCCG | 236-E3-001 |
| 71 | D-RNA | GCACUCGUAAAGUAGAGGGACCAGUCCGGCGUGAUAGUGCCGAGUGC | 223-C5-008 |
| 72 | D-RNA | GUGUGUAAAGUAGAGGACAAUUGUCGGCGUGAUAGUGCCACAC | 229-B1-003 |
| 73 | D-RNA | GCGUGUAAAGUAGAGGACAAUUGUCGGCGUGAUAGUGCCACGC | 229-B1-004 |
| 74 | D-RNA | GCGCGUAAAGUAGAGGACAAUUGUCGGCGUGAUAGUGCCGCGC | 229-B1-005 |
| 75 | D-RNA | CGUGUGUAAAGUAGAGGACAAUUGUCGGCGUGAUAGUGCCACAC | 229-B1-006 |
| 76 | D-RNA | GCCGUGUAAAGUAGAGGACAAUUGUCGGCGUGAUAGUGCCACGGC | 229-B1-007 |
| 77 | D-RNA | GCGGUGUAAAGUAGAGGACAAUUGUCGGCGUGAUAGUGCCACCGC | 229-B1-008 |
| 78 | D-RNA | GCUGCGUAAAGUAGAGGACAAUUGUCGGCGUGAUAGUGCCGCAGC | 229-B1-009 |
| 79 | D-RNA | GCUGGGUAAAGUAGAGGACAAUUGUCGGCGUGAUAGUGCCCCAGC | 229-B1-010 |
| 80 | D-RNA | GCGGCGUAAAGUAGAGGACAAUUGUCGGCGUGAUAGUGCCGCCGC | 229-B1-011 |
| 81 | D-RNA | GCGCGCGUAUGGGAUUAAGUAAAUGAGGAGUUGGAGGAAGGCGCGC | 238-D4-002 |
| 82 | D-RNA | GCGCGCGUAUGGGAUAAGUAAAUGAGGAGUUGGAGGAAGGCGCGC | 238-D4-003 |
| 83 | D-RNA | GGCGCGUAUGGGAUUAAGUAAAUGAGGAGUUGGAGGAAGGCGCC | 238-D4-004 |
| 84 | D-RNA | GGCGCGUAUGGGAUAAGUAAAUGAGGAGUUGGAGGAAGGCGCC | 238-D4-005 |
| 85 | D-RNA | GGUGUCGUAUGGGAUUAAGUAAAUGAGGAGUUGGAGGAAGGGCAUC | 238-D4-006 |
| 86 | D-RNA | GGUGUCGUAUGGGAUAAGUAAAUGAGGAGUUGGAGGAAGGGCAUC | 238-D4-007 |
| 87 | D-RNA | GCGCCGUAUGGGAUUAAGUAAAUGAGGAGUUGGAGGAAGGGCGC | 238-D4-008 |

| Seq.-ID | RNA/Peptide | Sequence | Internal Reference |
|---|---|---|---|
| 88 | D-RNA | GCGCCGUAUGGGAUAAGUAAAUGAGGAGUUGGAGGAAGGGCGC | 238-D4-009 |
| 89 | D-RNA | GGCGCCGUAUGGGAUUAAGUAAAUGAGGAGUUGGAGGAAGGGCGCC | 238-D4-010 |
| 90 | D-RNA | GGCGCCGUAUGGGAUAAGUAAAUGAGGAGUUGGAGGAAGGGCGCC | 238-D4-011 |
| 91 | D-RNA | GGCGUCGUAUGGGAUUAAGUAAAUGAGGAGUUGGAGGAAGGGCGCC | 238-D4-012 |
| 92 | D-RNA | GGCGUCGUAUGGGAUAAGUAAAUGAGGAGUUGGAGGAAGGGCGCC | 238-D4-013 |
| 93 | D-RNA | GGCUCGGACAGCCGGGGGACACCAUAUACAGACUACGAUACGGGCC | 238-C4-002 |
| 94 | D-RNA | GCUCGGACAGCCGGGGGACACCAUAUACAGACUACGAUACGGGC | 238-C4-003 |
| 95 | D-RNA | CUCGGACAGCCGGGGGACACCAUAUACAGACUACGAUACGGG | 238-C4-004 |
| 96 | D-RNA | GCCCGGACAGCCGGGGGACACCAUAUACAGACUACGAUACGGGC | 238-C4-005 |
| 97 | D-RNA | GGCCGGACAGCCGGGGGACACCAUAUACAGACUACGAUACGGCC | 238-C4-006 |
| 98 | D-RNA | GCGGAGACAGCCGGGGGACACCAUAUACAGACUACGAUAUCCGU | 238-C4-007 |
| 99 | D-RNA | AGGCUGACAGCCGGGGGACACCAUAUACAGACUACGAUAGGCCU | 238-C4-008 |
| 100 | D-RNA | GGCCUGACAGCCGGGGGACACCAUAUACAGACUACGAUAAGGCU | 238-C4-009 |
| 101 | D-RNA | GCGCGGACAGCCGGGGGACACCAUAUACAGACUACGAUACGCGC | 238-C4-010 |
| 102 | D-RNA | GCCGGACAGCCGGGGGACACCAUAUACAGACUACGAUACGGC | 238-C4-011 |
| 103 | D-RNA | GGCGGACAGCCGGGGGACACCAUAUACAGACUACGAUACGCC | 238-C4-012 |
| 104 | D-RNA | GGCCGACAGCCGGGGGACACCAUAUACAGACUACGAUAGGCC | 238-C4-013 |
| 105 | D-RNA | GCGCGACAGCCGGGGGACACCAUAUACAGACUACGAUAGCGC | 238-C4-014 |
| 106 | D-RNA | GGCCGGACAGCCGGAGGACACCAUAUACAGACUACGAUACGGCC | 238-C4-024 |
| 107 | D-RNA | GGCCGGACAGCCGGCGGACACCAUAUACAGACUACGAUACGGCC | 238-C4-025 |
| 108 | D-RNA | GGCCGGACAGCCGGGAGGACACCAUAUACAGACUACGAUACGGCC | 238-C4-062 |
| 109 | L-RNA | 5'UCCAGGUUCUGGA | |
| 110 | L-RNA | AGGCGUAAAGUAGAGGGGCUGAGCCCGGCGUGUUAGUGCCGCCU | 238-A1-001 |
| 111 | L-RNA | AGGCGUAAAGUAGAGGGACGUAGUCCGGCGUGAUAGUGCCGCCU | 238-E2-001 |
| 112 | L-RNA | CGUGUGUAAAGUAGAGGCAGAUAAUCUGCGGAGUGUUAGUUCCACACG | 237-A7-001 |
| 113 | L-RNA | CGUGAAAAGUAGAAACUUGUCGAAAGCAAGCAGCGUGAUAGUGCCACG | 236-G2-001 |
| 114 | L-RNA | CGUGAAAAGUUGAAAUUUGUUGGAAUCAAGCAGGGAUAUAGUGCCACG | 236-D1-001 |

-continued

| Seq.-ID | RNA/Peptide | Sequence | Internal Reference |
|---|---|---|---|
| 115 | L-RNA | AGCGUGUCGUAUGGGAUAAGUAAAUGAGGAGUUGGAGGAAGGGUGCGCU | 238-D2-001 |
| 116 | L-RNA | AGCGUGUCGUAUGGGAUUAAGUAAAUGAGGAGUUGGAGGAAGGGCAUGCU | 238-D4-001 |
| 117 | L-RNA | AGUGUGUCGUAUGGGAUAAGUAAAUGAGGGGUUGGAGGAAGGAUGCGCU | 238-H1-001 |
| 118 | L-RNA | AGUGUGUCAUAUGGGAUAAGUAAAUGAGGAGUUGGAGGAAAGGCAUGCU | 238-A2-001 |
| 119 | L-RNA | AGCGUGCCGGAUGGGAUAAGUAAAUGAGGAGUUGGAGGAAGGGUGCGCU | 238-G2-001 |
| 120 | L-RNA | AGCGUGCCGUAUGGGAUAAGUAAAUGAGGAGUAGGAGGAAGGGUACGCU | 238-G4-001 |
| 121 | L-RNA | AGCGCGCCGUAUGGGAGAAGUAAAUGAGGAGUUGGAGGAAGGGCGCGCU | 238-G3-001 |
| 122 | L-RNA | AGGCUCGGACAGCCGGGGGACACCAUAUACAGACUACGAUACGGGCCU | 238-C4-001 |
| 123 | L-RNA | AGGCUCGGACGGCCGGGGGACACCAUAUACAGACUACUAUACGGGCCU | 238-E3-001 |
| 124 | L-RNA | AGGCCCGGACAGCCGGGGGACACCAUAUACAGACUACUAUACGGGCCU | 238-F2-001 |
| 125 | L-RNA | AGGCUUGGGCGGCCGGGGGACACCAUAUACAGACUACUAUACGAGCCU | 238-A4-001 |
| 126 | L-RNA | AGACUUGGGCAGCCGGGGGACACCAUAUACAGACUACGAUACGAGUCU | 238-E1-001 |
| 127 | L-RNA | CGGGCGCCAUAGACCGUUAUUAAGCACUGUAACUACCGAACCGCGCCCG | 237-A5-001 |
| 128 | L-RNA | CGGGCGCCAUAGACCGUUAACUACAUAACUACCGAACCGUGCCCG | 237-C5-001 |
| 129 | L-RNA | CGGGCGCUACCGAACCCACUAAAACCAGUGCAUAGACCGCGCCCG | 236-F2-001 |
| 130 | L-RNA | CGGGCGCUACCGAACCGUCACGAAGACCAUAGACCGCGCCG | 236-G4-001 |
| 131 | L-RNA | CGAGCGCAACCGAACCUCUACCCAGACAUAGACCGCGCCCG | 236-E3-001 |
| 132 | L-RNA | GCACUCGUAAAGUAGAGGGACCAGUCCGGCGUGAUAGUGCCGAGUGC | 223-C5-008 |
| 133 | L-RNA | GUGUGUAAAGUAGAGGACAAUUGUCGGCGUGAUAGUGCCACAC | 229-B1-003 |
| 134 | L-RNA | GCGUGUAAAGUAGAGGACAAUUGUCGGCGUGAUAGUGCCACGC | 229-B1-004 |
| 135 | L-RNA | GCGCGUAAAGUAGAGGACAAUUGUCGGCGUGAUAGUGCCGCGC | 229-B1-005 |
| 136 | L-RNA | CGUGUGUAAAGUAGAGGACAAUUGUCGGCGUGAUAGUGCCACAC | 229-B1-006 |
| 137 | L-RNA | GCCGUGUAAAGUAGAGGACAAUUGUCGGCGUGAUAGUGCCACGGC | 229-B1-007 |
| 138 | L-RNA | GCGGUGUAAAGUAGAGGACAAUUGUCGGCGUGAUAGUGCCACCGC | 229-B1-008 |
| 139 | L-RNA | GCUGCGUAAAGUAGAGGACAAUUGUCGGCGUGAUAGUGCCGCAGC | 229-B1-009 |

-continued

| Seq.-ID | RNA/Peptide | Sequence | Internal Reference |
|---|---|---|---|
| 140 | L-RNA | GCUGGGUAAAGUAGAGGACAAUUGUCGGCGUGAUAGUGCCCCAGC | 229-B1-010 |
| 141 | L-RNA | GCGGCGUAAAGUAGAGGACAAUUGUCGGCGUGAUAGUGCCGCCGC | 229-B1-011 |
| 142 | L-RNA | GCGCGCGUAUGGGAUUAAGUAAAUGAGGAGUUGGAGGAAGGCGCGC | 238-D4-002 |
| 143 | L-RNA | GCGCGCGUAUGGGAUAAGUAAAUGAGGAGUUGGAGGAAGGCGCGC | 238-D4-003 |
| 144 | L-RNA | GGCGCGUAUGGGAUUAAGUAAAUGAGGAGUUGGAGGAAGGCGCC | 238-D4-004 |
| 145 | L-RNA | GGCGCGUAUGGGAUAAGUAAAUGAGGAGUUGGAGGAAGGCGCC | 238-D4-005 |
| 146 | L-RNA | GGUGUCGUAUGGGAUUAAGUAAAUGAGGAGUUGGAGGAAGGGCAUC | 238-D4-006 |
| 147 | L-RNA | GGUGUCGUAUGGGAUAAGUAAAUGAGGAGUUGGAGGAAGGGCAUC | 238-D4-007 |
| 148 | L-RNA | GCGCCGUAUGGGAUUAAGUAAAUGAGGAGUUGGAGGAAGGGCGC | 238-D4-008 |
| 149 | L-RNA | GCGCCGUAUGGGAUAAGUAAAUGAGGAGUUGGAGGAAGGGCGC | 238-D4-009 |
| 150 | L-RNA | GGCGCCGUAUGGGAUUAAGUAAAUGAGGAGUUGGAGGAAGGGCGCC | 238-D4-010 |
| 151 | L-RNA | GGCGCCGUAUGGGAUAAGUAAAUGAGGAGUUGGAGGAAGGGCGCC | 238-D4-011 |
| 152 | L-RNA | GGCGUCGUAUGGGAUUAAGUAAAUGAGGAGUUGGAGGAAGGGCGCC | 238-D4-012 |
| 153 | L-RNA | GGCGUCGUAUGGGAUAAGUAAAUGAGGAGUUGGAGGAAGGGCGCC | 238-D4-013 |
| 154 | L-RNA | GGCUCGGACAGCCGGGGACACCAUAUACAGACUACGAUACGGGCC | 238-C4-002 |
| 155 | L-RNA | GCUCGGACAGCCGGGGACACCAUAUACAGACUACGAUACGGGC | 238-C4-003 |
| 156 | L-RNA | CUCGGACAGCCGGGGACACCAUAUACAGACUACGAUACGGG | 238-C4-004 |
| 157 | L-RNA | 5'GACAAUAGUC | |
| 158 | L-RNA | GCCCGGACAGCCGGGGACACCAUAUACAGACUACGAUACGGGC | 238-C4-005 |
| 159 | L-RNA | GGCCGGACAGCCGGGGACACCAUAUACAGACUACGAUACGGCC | 238-C4-006 |
| 160 | L-RNA | GCGGAGACAGCCGGGGACACCAUAUACAGACUACGAUAUCCGU | 238-C4-007 |
| 161 | L-RNA | AGGCUGACAGCCGGGGACACCAUAUACAGACUACGAUAGGCCU | 238-C4-008 |
| 162 | L-RNA | GGCCUGACAGCCGGGGACACCAUAUACAGACUACGAUAAGGCU | 238-C4-009 |
| 163 | L-RNA | GCGCGGACAGCCGGGGACACCAUAUACAGACUACGAUACGCGC | 238-C4-010 |
| 164 | L-RNA | GCCGGACAGCCGGGGACACCAUAUACAGACUACGAUACGGC | 238-C4-011 |
| 165 | L-RNA | GGCGGACAGCCGGGGACACCAUAUACAGACUACGAUACGCC | 238-C4-012 |
| 166 | L-RNA | GGCCGACAGCCGGGGACACCAUAUACAGACUACGAUAGGCC | 238-C4-013 |

| Seq.-ID | RNA/Peptide | Sequence | Internal Reference |
|---|---|---|---|
| 167 | L-RNA | GCGCGACAGCCGGGGGACACCAUAUACAGACUACGAUAGCGC | 238-C4-014 |
| 168 | L-RNA | GGCCGGACAGCCGGAGGACACCAUAUACAGACUACGAUACGGCC | 238-C4-024 |
| 169 | L-RNA | GGCCGGACAGCCGGCGGACACCAUAUACAGACUACGAUACGGCC | 238-C4-025 |
| 170 | L-RNA | GGCCGGACAGCCGGGAGGACACCAUAUACAGACUACGAUACGGCC | 238-C4-062 |
| 171 | L-RNA | 5'-NH$_2$-GCUGUGUAAAGUAGAGGACAAUUGUCGGCGUGAUAGUGCCACAGC | 229-B1-002-5'-Amino |
| 172 | L-RNA | 5'-NH$_2$-GCACUCGUAAAGUAGAGGGACCCAGUCCGGCGUGAUAGUGCCGAGUGC | 223-C5-001-5'-Amino |
| 173 | L-RNA | 5'-PEG-GCUGUGUAAAGUAGAGGACAAUUGUCGGCGUGAUAGUGCCACAGC | 229-B1-002-5'-PEG |
| 174 | L-RNA | 5'-PEG-GGCCGGACAGCCGGGGGACACCAUAUACAGACUACGAUACGGCC | 238-C4-006-5'_PEG |
| 175 | L-RNA | 5'-PEG-GCGCGCGUAUGGGAUUAAGUAAAUGAGGAGUUGGAGGAAGGCGCGC | 238-D4-002-5'-PEG |
| 176 | L-RNA | 5'-PEG-GCGCCGUAUGGGAUUAAGUAAAUGAGGAGUUGGAGGAAGGCGC | 238-D4-008-5'-PEG, NOX-H94 |
| 177 | L-RNA | 5'-CCAUACGGCGC-C18-C18-NH$_2$- | 5'CP-11_NOX-H94 |
| 178 | L-RNA | 5'-Biotin-C18-C18-GCGCCCUUCCUCC | 3'DP-13_NOX-H94 |
| 179 | L-RNA | 5'-NH$_2$-GCGCGCGUAUGGGAUUAAGUAAAUGAGGAGUUGGAGGAAGGCGCGC | 238-D4-002-5'-Amino |
| 180 | L-RNA | 5'-NH$_2$-GCGCCGUAUGGGAUUAAGUAAAUGAGGAGUUGGAGGAAGGGCGC | 238-D4-008-5'-Amino |
| 181 | L-RNA | 5'-NH$_2$-GGCCGGACAGCCGGGGGACACCAUAUACAGACUACGAUACGGCC | 238-C4-006-5'-Amino |
| 182 | L-RNA | 5'RKAUGGGAKUAAGUAAAUGAGGRGUWGGAGGAAR | |
| 183 | L-RNA | 5'RKAUGGGAKAAGUAAAUGAGGRGUWGGAGGAAR | |
| 184 | L-RNA | 5'GUAUGGGAUUAAGUAAAUGAGGAGUUGGAGGAAG | |
| 185 | L-RNA | 5'GRCRGCCGGVGGACACCAUAUACAGACUACKAUA | |
| 186 | L-RNA | 5'GRCRGCCGGARGGACACCAUAUACAGACUACKAUA | |
| 187 | L-RNA | 5'GACAGCCGGGGGACACCAUAUACAGACUACGAUA | |
| 188 | L-RNA | 5'WAAAGUWGAR | |
| 189 | L-RNA | 5'RGMGUGWKAGUKC | |
| 190 | L-RNA | 5'GGGCUGAGCCC | |
| 191 | L-RNA | 5'GCAGAUAAUCUGC | |
| 192 | L-RNA | 5'GGACCAGUCC | |
| 193 | L-RNA | 5'GGACCCAGUCC | |
| 194 | L-RNA | 5'GGACCUAGUCC | |

-continued

| Seq.-ID | RNA/Peptide | Sequence | Internal Reference |
|---|---|---|---|
| 195 | L-RNA | 5'GGACUCAGUCC | |
| 196 | L-RNA | 5'GCAGGUAAUCUGC | |
| 197 | L-RNA | 5'GCAGGCAAUCUGC | |
| 198 | L-RNA | 5'GACAAUUGUC | |
| 199 | L-RNA | 5'UAAAGUAGAG | |
| 200 | L-RNA | 5'AAAAGUAGAA | |
| 201 | L-RNA | 5'AAAAGUUGAA | |
| 202 | L-RNA | 5'GGGAUAUAGUGC | |
| 203 | L-RNA | 5'GGCGUGAUAGUGC | |
| 204 | L-RNA | 5'GGAGUGUUAGUUC | |
| 205 | L-RNA | 5'GGCGUGAGAGUGC | |
| 206 | L-RNA | 5'AGCGUGAUAGUGC | |
| 207 | L-RNA | 5'GGCGUGUUAGUGC | |
| 208 | L-RNA | 5'GGACBYAGUCC | |
| 209 | L-RNA | 5'GGAUACAGUCC | |
| 210 | L-RNA | 5'GCAGGYAAUCUGC | |
| 211 | L-RNA | 5'GACAAUWGUC | |
| 212 | L-RNA | 5'ACUUGUCGAAAGCAAGYU | |

The present invention is further illustrated by the figures, examples and the sequence listing from which further features, embodiments and advantages may be taken, wherein FIGS. 1 and 2 shows an alignment of sciences of Type A hepcidin binding nucleic acids (FIG. 1 discloses the D-RNA sequences as SEQ ID NOS 10-20, 22-23, and 49-52, respectively, in order of appearance, and the corresponding L-RNA sequences as SEQ ID NOS 29-39, 41-42, and 110-113, respectively. FIG. 2 discloses the D-RNA sequences as SEQ ID NOS 10, 24-25, and 53, respectively, in order of appearance, and the corresponding L-RNA sequences as SEQ ID NOS 29, 43-44, and 114, respectively);

FIG. 3 shows derivatives of Type A hepcidin binding nucleic acid 223-C5-001 (FIG. 3 discloses the D-RNA sequences as SEQ ID NOS 10, 26-38, and 71, respectively, in order of appearance, and she corresponding L-RNA sequences as SEQ ID NOS 29, 45-47, and 132, respectively);

FIG. 4 shows derivatives of Type A hepcidin binding nucleic acid 229-B1-001 (FIG. 4 discloses the D-RNA sequences as SEQ ID NOS 20-21 and 72-80, respectively, in order of appearance, and the corresponding L-RNA sequences as SEQ ID NOS 39-40 and 133-141, respectively);

FIG. 5 shows an alignment of sequences of Type B hepcidin binding nucleic acids (FIG. 5 discloses the D-RNA sequences as SEQ ID NOS 54-60, respectively, in order of appearance, and the corresponding L-RNA sequences as SEQ ID NOS 115-121, respectively);

FIG. 6 shows derivatives of Type B hepcidin binding nucleic acid 238-D4-001 (FIG. 6 discloses the D-RNA sequences as SEQ ID NOS 55 and 81-92, respectively, in order of appearance, and the corresponding L-RNA sequences as SEQ ID NOS 116 and 142-153, respectively);

FIG. 7 shows an alignment of sequences of Type C hepcidin binding nucleic acids (FIG. 7 discloses the D-RNA sequences as SEQ ID NOS 61-65, respectively, in order of appearance, and the corresponding L-RNA sequences as SEQ ID NOS 122-126, respectively);

FIG. 8 shows derivatives of Type C hepcidin binding nucleic acid 238-C4-001 (FIG. 8 discloses the D-RNA sequences as SEQ ID NOS 61 and 93-108, respectively, in order of appearance, and the corresponding L-RNA sequences as SEQ ID NOS 122, 154-156, and 158-170, respectively);

FIG. 9 shows an alignment of sequences of other hepcidin binding nucleic acids (FIG. 9 discloses the D-RNA sequences as SEQ ID NOS 66-70, respectively, in order of appearance, and the corresponding L-RNA sequences as SEQ ID NOS 127-131, respectively);

FIG. 10 shows data regarding the binding of hepcidin binding nucleic acids 223-C5-001, 229-B1-002, 238-C4-006, 238-D4-001 and 238-D4-008 to human hepcidin-25, cynomolgus hepcidin-25, marmoset hepcidin-25, mouse hepcidin-25 and rat hepcidin-25;

FIG. 11 shows data regarding the binding of hepcidin binding nucleic acids 223-C5-001, 229-B1-002, 238-C4-006, 238-D4-001 and 238-D4-008 to human hepcidin-25, hepcidin-22 and hepcidin-20;

FIG. 12 shows data regarding the binding of hepcidin binding nucleic acids 223-C5-001-5'-PEG, 229-B1-002-5'-PEG, 238-C4-006-5'-PEG, 238-D4-002-5'-PEG and 238-D4-008-5'-PEG to human hepcidin-25;

Figure 14:
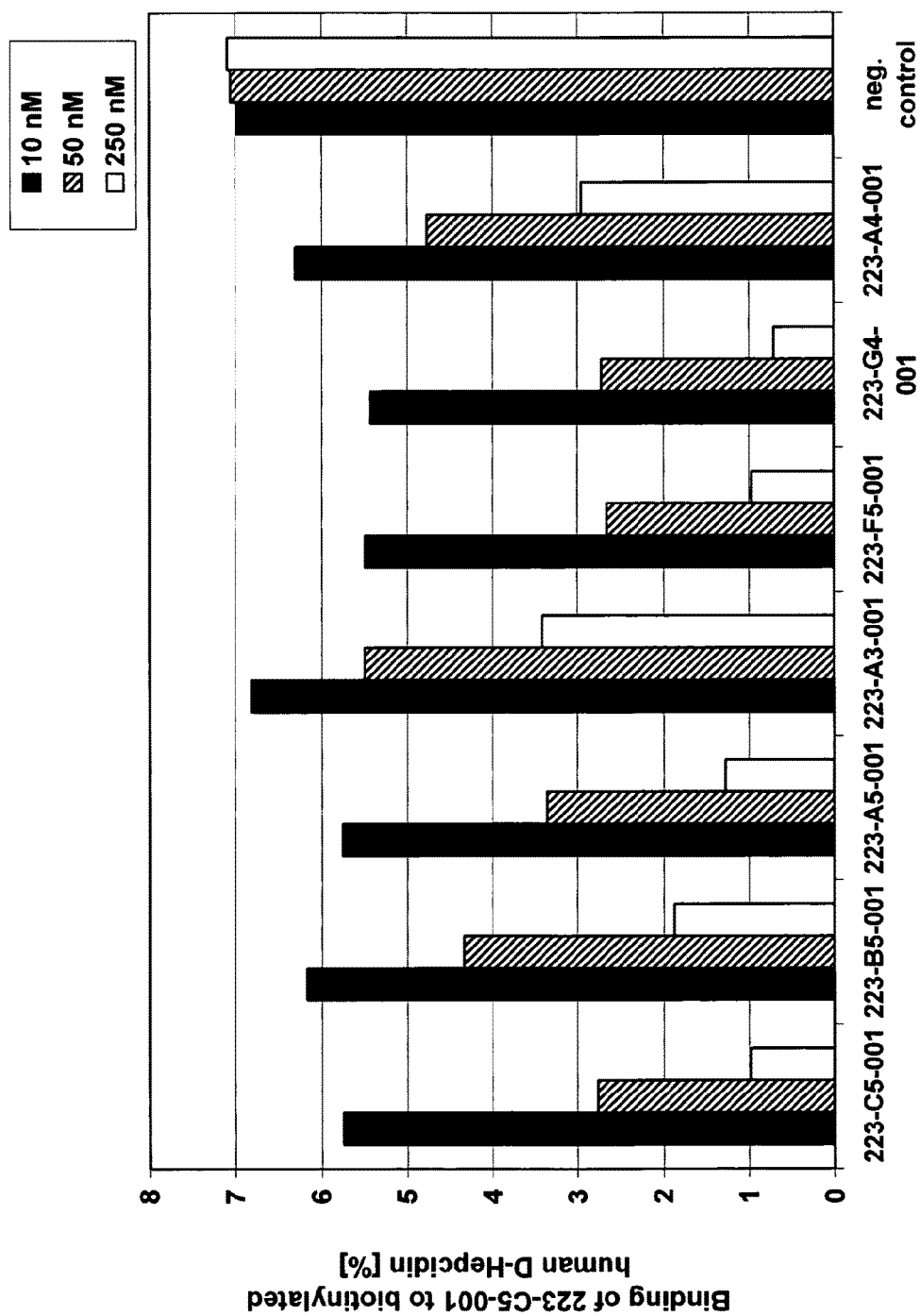
Figure 15:
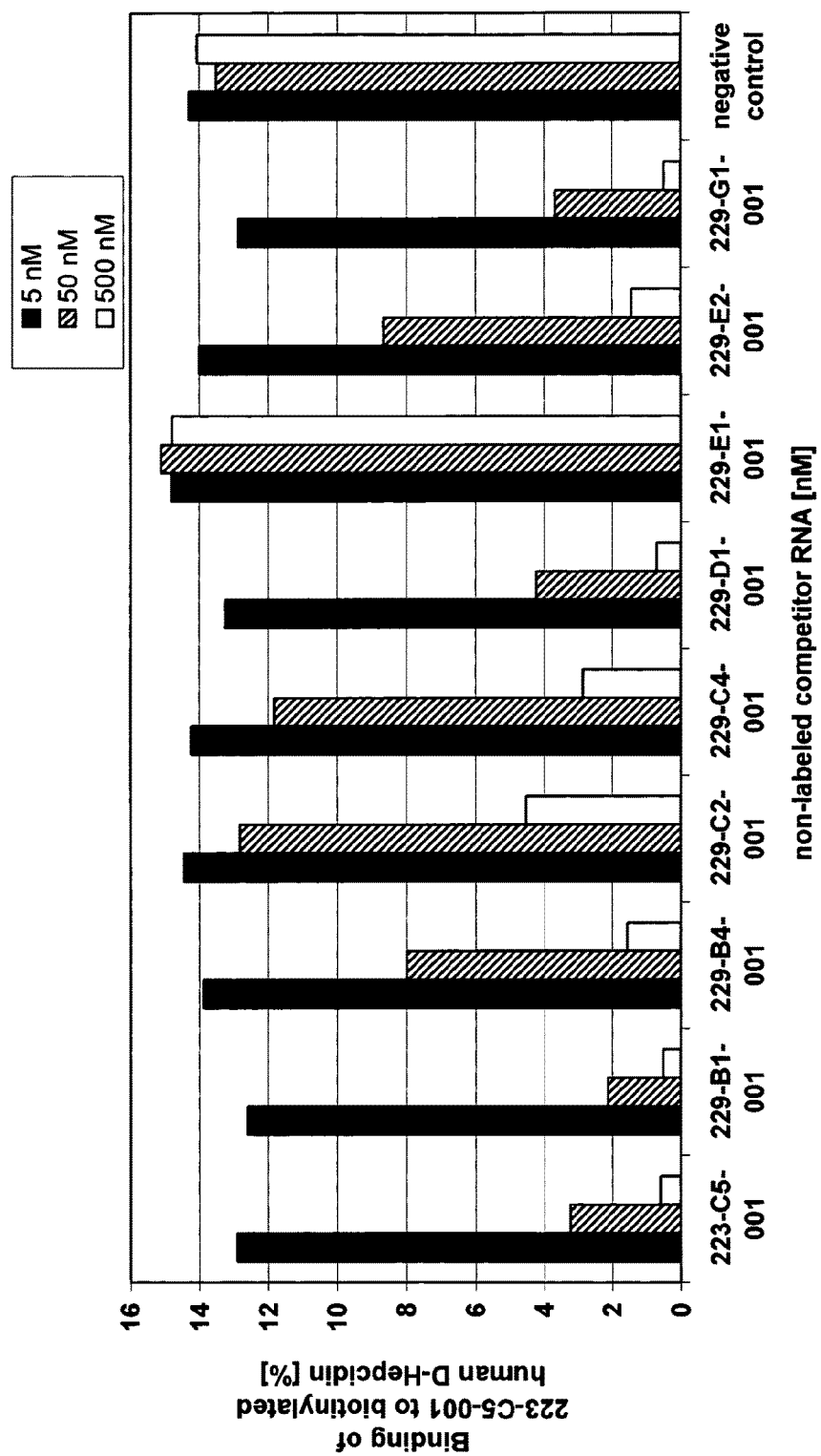

FIGS. 14 and 15 show the results of the ranking experiments to compare the hepcidin binding nucleic acids to each other and to identify the best hepcidin binding nucleic acids, whereby the Type A hepcidin binding nucleic acid 233-C5-001 was labeled and the binding of nucleic acid 233-C5-001 to biotinylated human D-hepcidin-25 at 37° C. was carried out in the presence of 10, 50 or 250 nM non-labeled competitor RNA, the different Type hepcidin binding nucleic acids, respectively, represented as binding of 223-C5-001 over concentration of biotinylated human D-hepcidin-25 ('competitive pull-down assay')

Figure 16:
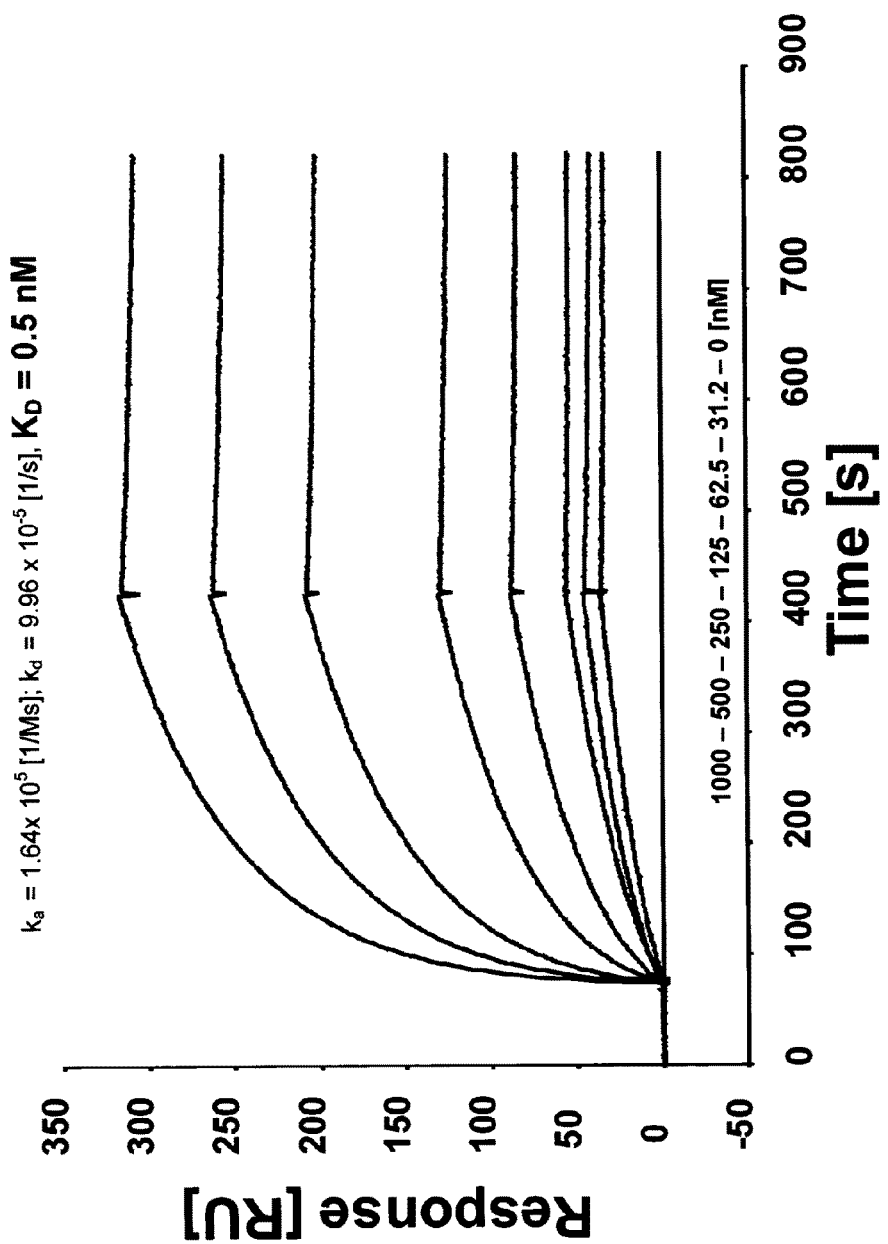
Figure 17:
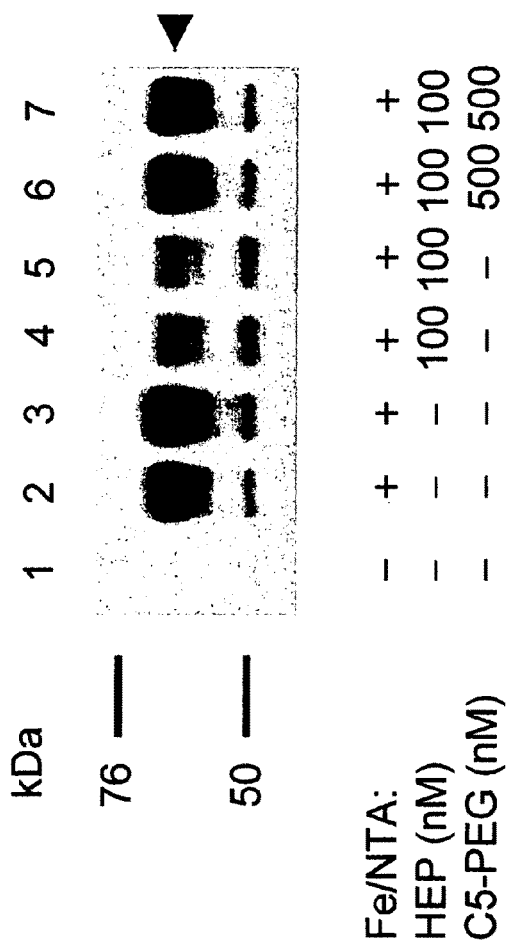
Figure 18:
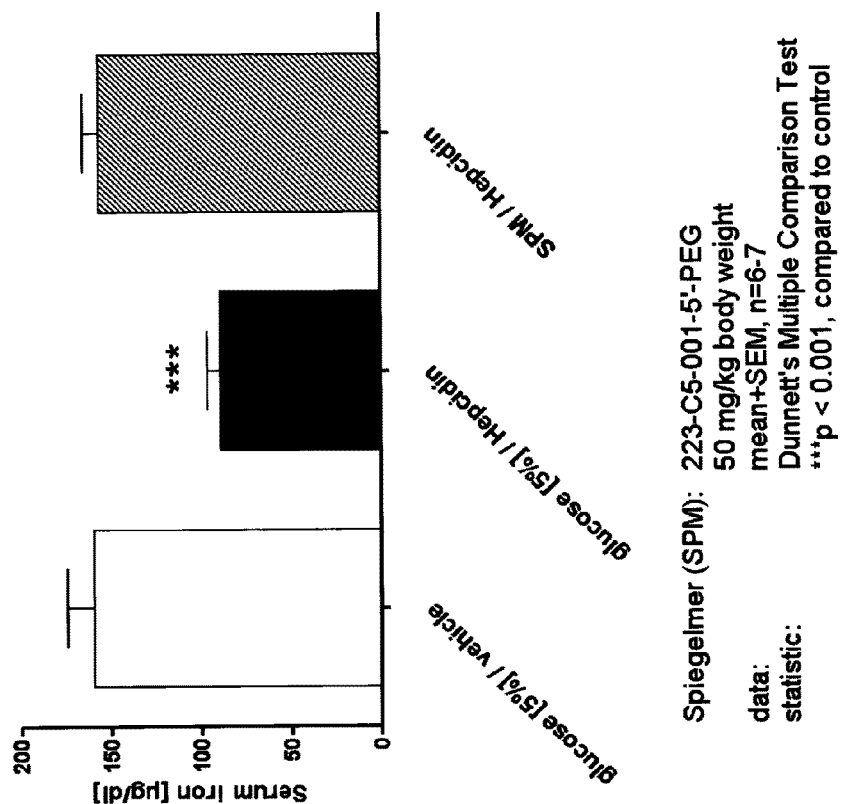
Figure 19:
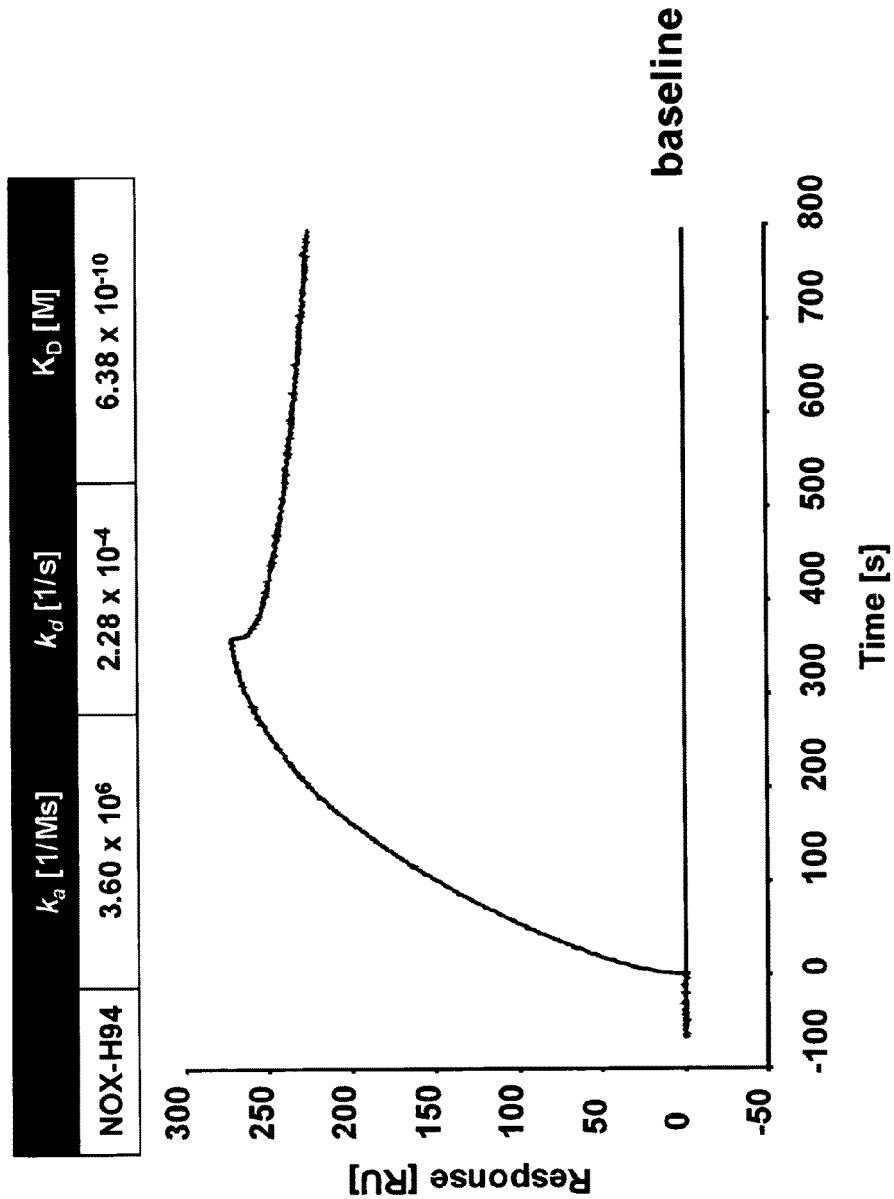
Figure 20:
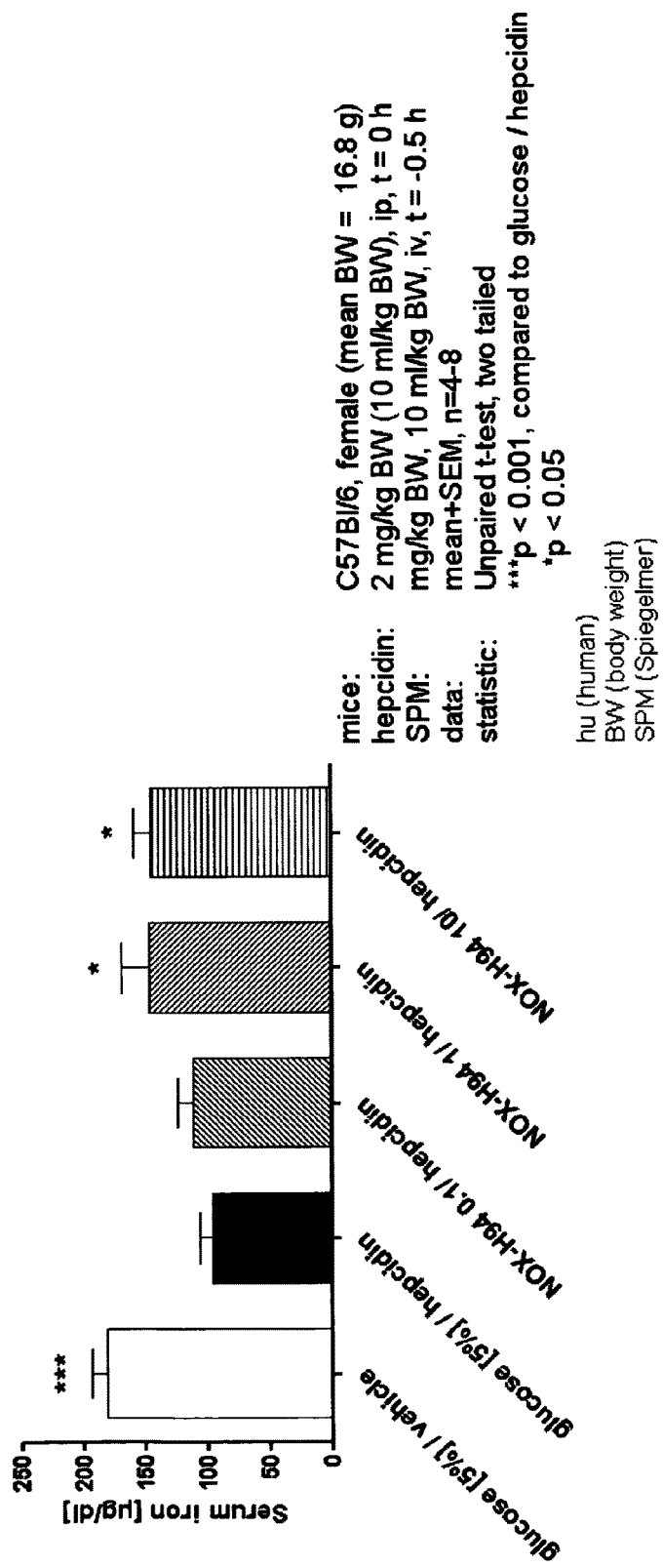
Figure 21:
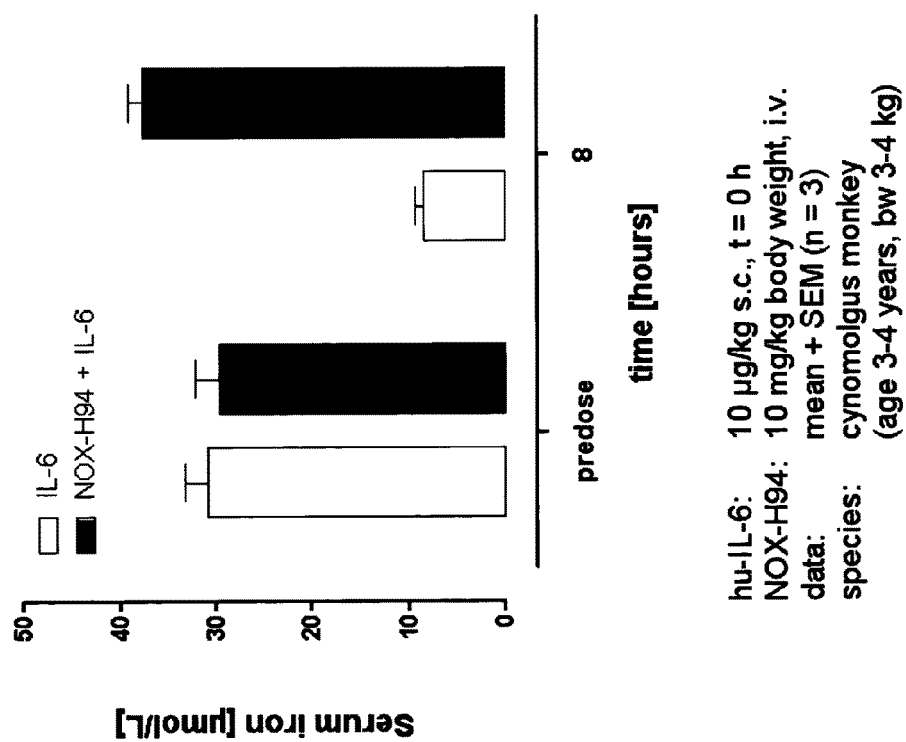

FIG. 16 shows Biacore 2000 sensorgram indicating the $K_D$ value of the aptamer of Type A hepcidin binding nucleic acid 229-B1-001 binding to biotinylated human D-hepcidin-25 at 37° C., whereby the biotinylated human D-hepcidin-25 was immobilized by strepatavidin coupling procedure on a strepatavidin conjugated sensor chip at 37° C., represented as response (RU) over time;

FIG. 17A/17B show the effect of the Spiegelmers 223-C5-001-5'-PEG, 238-D4-008-5'-Amino and 238-D4-008-5'-PEG (=NOX-H94) on the effect of human hepcidin-25 on iron-induced up-regulation of ferroportin, whereby the lysates obtained from J774.1 cells after stimulation with hepcidin human-25) or hepcidin-25 )+Spiegelmer were separated by SDS-gel electrophoresis and analysed by Western Blot using an antibody against mouse ferroportin;

FIG. 18 shows the effect of the Spiegelmer 223-C5-001-5'-PEG on hepcidin activity in vivo, whereby the decrease in serum iron caused by human hepcidin is completely blocked by application of Spiegelmer 223-C5-001-5'-PEG prior to injection of human hepcidin;

FIG. 19 shows Biacore 2000 sensorgram indicating the $K_D$ value of the spiegelmer of hepcidin binding nucleic acid NOX-H94 (=238-D4-008-5'-PEG) binding to biotinylated human L-hepcidin at 37° C., whereby the biotinylated human L-hepcidin was immobilized by strepatavidin coupling procedure on a strepatavidin conjugated sensor chip at 37° C., represented as response (RU) over time;

FIG. 20 shows the effect of the Spiegelmer NOX-H94 (=238-D4-008-5'-PEG) on hepcidin activity in vivo, whereby the decrease in serum iron caused by human hepcidin is completely blocked by application of Spiegelmer NOX-H94 (=238-D4-008-5'-PEG) prior to injection of human hepcidin;

FIG. 21 shows the effect of the Spiegelmer NOX-H94 (=238-D4-008-5'-PEG) in an animal model (cynomolgus monkey) for anaemia of inflammation, whereby IL-6 induces hepcidin secretion subsequently resulting in anemia in non-human primates; within the experiment human IL-6 leads a reduction of serum iron concentration to 27% of the predose value of the vehicle/IL-6 treated monkeys, the decrease in serum iron is completely blocked by application of spiegelmer 238-D4-008-5'-PEG prior to injection of human IL-6.

EXAMPLE 1

Nucleic Acids that Bind Human Hepcidin

Using biotinylated human D-hepcidin-25 as a target, several nucleic acids that bind to human hepcidin, in particular human hepcidin-25, human hepcidin-22 and human hepcidin-20, could be generated: the nucleotide sequences of which are depicted in FIGS. 1 through 9. The nucleic acids were characterized on the aptamer, i. e. D-nucleic acid level using a direct pull-down assay (Example 3), a competitive pull-down assay (Example 3) and/or surface plasmon resonance measurement (Example 4) with biotinylated human D-hepcidin-25 or on the spiegelmer level, i. e. L-nucleic acid with the natural configuration of human hepcidin-25 (human L-hepcidin-25), in a competitive pull-down assay (Example 3), surface plasmon resonance measurement (Example 4), in an in vitro assay (Example 5) and/or an in vivo assay (Example 6 and 7). The spiegelmers and aptamers were synthesized as described in Example 2.

The nucleic acid molecules thus generated exhibit different sequence motifs, whereby three main types were identified and defined as Type A, Type B and Type C hepcidin binding nucleic acids and are depicted in FIGS. 1 through 8.

For definition of nucleotide sequence motifs, the IUPAC abbreviations for ambiguous nucleotides are used:

| | | |
|---|---|---|
| S | strong | G or C; |
| W | weak | A or U; |
| R | purine | G or A; |
| Y | pyrimidine | C or U; |
| K | keto | G or U; |
| M | imino | A or C; |
| B | not A | C or U or G; |
| D | not C | A or G or U; |
| H | not G | A or C or U; |
| V | not U | A or C or G; |
| N | all | A or G or C or U |

If not indicated to the contrary, any nucleic acid sequence or sequence of stretches and boxes, respectively, is indicated in the 5'→3' direction.

1.1 Type A Hepcidin Binding Nucleic Acids

As depicted in FIG. 1, FIG. 2, FIG. 3 and FIG. 4 the Type A hepcidin binding nucleic acids comprise one central stretch of nucleotides, wherein the central stretch of nucleotides comprises at least two stretches of nucleotides—also referred to herein as boxes of nucleotides—defining a potential hepcidin binding motif: the firststretch of nucleotides Box A and the second stretch of nucleotides Box B.

The first stretch of nucleotides Box A and the second stretch of nucleotides Box B are linked to each other by a linking stretch of nucleotides.

Within the linking stretch of nucleotides some nucleotides can hybridize to each other, whereby upon hybridization a double-stranded structure is formed. However, such hybridization is not necessarily given in the molecule.

In general. Type A hepcidin binding nucleic acids comprise at their 5'-end and the 3'-end terminal stretches of nucleotides: the first -terminal stretch of nucleotides and the second terminal stretch of nucleotides. The firstterminal stretch of nucleotides and the second terminal stretch of nucleotides can hybridize to each other, whereby upon hybridization a double-stranded structure is formed. However, such hybridization is not necessarily given in the molecule.

The five stretches of nucleotides of Type A. hepcidin binding nucleic acids Box A, Box B, linking stretch of nucleotides, first terminal stretch of nucleotides and second terminal stretch of nucleotides can be differently arranged to each other: first terminal stretch of nucleotides—Box A—linking stretch of nucleotides—Box B—second terminal stretch of nucleotides or first terminal stretch of nucleotides—Box B—linking stretch of nucleotides—Box A—second terminal stretch of nucleotides.

However, the five stretches of nucleotides of Type A hepcidin binding nucleic acids Box A, Box B, linking stretch of nucleotides, first terminal stretch of nucleotides and second terminal stretch of nucleotides can be also arranged to each other as follows: second terminal stretch of nucleotides—Box A—linking stretch of nucleotides—Box B—first terminal stretch of nucleotides or second terminal stretch of nucleotides—Box B—linking stretch of nucleotides—Box A—first terminal stretch of nucleotides.

The sequences of the defined boxes or stretches of nucleotides may be different between the Type A hepcidin binding nucleic acids which influences the binding affinity to human hepcidin, in particular human hepcidin-25. Based on binding analysis of the different Type A hepcidin binding nucleic acids, the box A and B and their nucleotide sequences as described in the following are individually and more preferably in their entirety essential for binding to human hepcidin, in particular human hepcidin-25.

Figure 13:
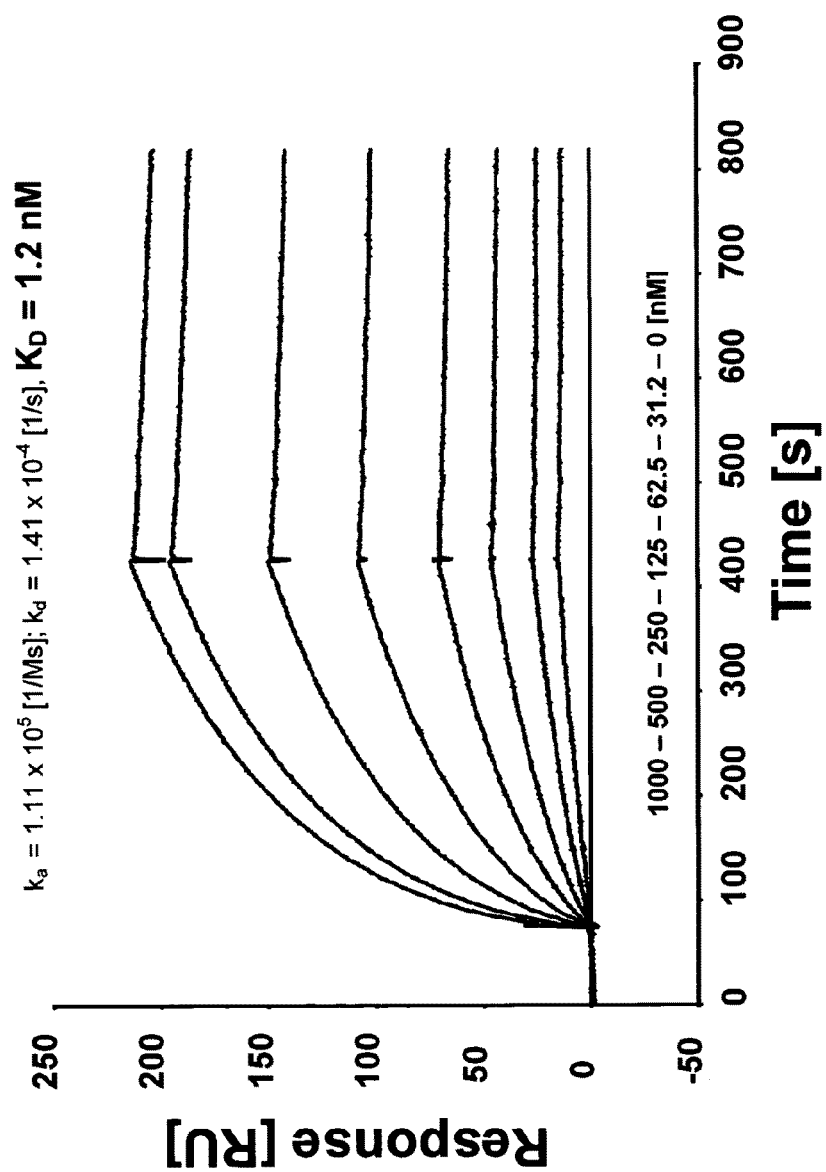
FIG. 13 shows Biacore 2000 sensorgram indicating the $K_D$ value of the aptamer of Type A hepcidin binding nucleic acid 223-C5-001 binding to biotinylated human D-hepcidin-25 at 37° C., whereby the biotinylated human D-hepcidin was immobilized by strepatavidin coupling procedure on a strepatavidin conjugated sensor chip at 37° C., represented as response (RU) over time.

The Type A hepcidin binding nucleic acids according to the present invention are shown in FIGS. 1 to 4. All of them were tested as aptamers and/or spiegelmers for their ability to bind human hepcidin-25, more precisely biotinylated human D-hepcidin-25 and biotinylated human L-hepcidin-24, respectively. The first Type A hepcidin binding nucleic acid that was characterized for its binding affinity to human hepcidin-25 is hepcidin binding nucleic acid 223-C5-001. The equilibrium binding constant $K_D$ for human hepcidin-25 was determined by surface plasmon resonance measurement ($K_D$=1.2 nM determined with the aptamer sequence. FIG. 13; $K_D$2.7 nM determined with the spiegelmer sequence, FIG. 11). In addition to human hepcidin-25, hepcidin binding nucleic acid 223-C5-001 binds to human hepcidin-20 with almost the same binding affinity (FIG. 11).

The derivatives 223-C5-002, 223-C5-007 and 223-C5-008 of Type A hepcidin binding nucleic acid 223-C5-001 showed reduced binding affinity in a competitive pull-down assay in comparison to Type A hepcidin binding nucleic acid 223-C5-001 (FIG. 3). Indeed, hepcidin binding nucleic acid 223-C5-006 showed in the same assay format similar binding to human hepcidin-25 as 223-C5-001 (FIG. 3).

Type A hepcidin binding nucleic acids 223-B5-001, 223-A5-001, 223-A3-001, 223-F5-001, 223-G4-001, 223-A4-001, 229-C2-001, 229-B4-001, 229-E2-001, 229-B1-001 229-G1-001, 229-C4-001, 238-A1-001, 238-E2-001, 237-A7-001, 236-G2-001, 236-D1-001, 229-D1-001 and 229-E1-001 were tested as aptamers in a competitive pull-down assay vs. Type A hepcidin binding nucleic acid 223-C5-001, whereby at first the binding affinity of the radioactively labeled aptamer 223-C5-001 was determined using the direct pull-down assay. No competition of the binding of Type A hepcidin binding nucleic acid 223-C5-001 by the nucleic acid 229-E1-001 could be observed (FIGS. 2 and 15). This observation let assume that nucleic acid 229-E1-001 has no or very low binding affinity to human hepcidin-25. The Type A hepcidin binding nucleic acids 223-B5-001, 223-A5-001, 223-A3-001, 223-A4-001, 229-C2-001, 229-B4-001, 229-E2-001, 229-C4-001, 238-A1-001, 238-E2-001, 237-A7-001, 236-G2-001 and 236-D1-001 showed reduced binding affinity in the competitive pull-down assay in comparison to Type A hepcidin binding nucleic acid 223-C5-001 (FIGS. 1, 14 and 15). Type A hepcidin binding nucleic acids 223-F5-001, 223-G4-001, 229-G1-001 and 229-D1-001 showed similar binding affinity as 223-C5-001 (FIGS. 1, 2, 14 and 15). Better binding affinity for biotinylated human D-hepcidin-25 could be observed for Type A hepcidin binding nucleic acid 229-B1-001 (FIGS. 1 and 15). Therefore Type A hepcidin binding nucleic acid 229-B1-001 was further characterized. The equilibrium binding constant $K_D$ of Type A hepcidin binding nucleic acid 229-B1-001 was determined by surface plasmon resonance measurement ($K_D$=0.5 nM determined with the aptamer sequence. FIG. 16; $K_D$=1.25 nM determined with the spiegelmer sequence, data not shown).

The derivatives 229-B1-003, 229-B1-004, 229-B1-005 and 229-B1-006 of Type A hepcidin binding nucleic acid 229-B1-001 showed reduced binding affinity in a competitive pull-down assay in comparison to Type A hepcidin binding nucleic acid 229-B1-001 (FIG. 4). Indeed, Type A hepcidin binding nucleic acids 229-B1-002, 229-B1-007, 229-B1-008, 229-B1-009, 229-B1-010 and 229-B1-011 showed in the same assay format similar binding as or slightly improved binding to human hepcidin-25 in comparison to 229-B1-001 (FIG. 4).

Type A hepcidin binding nucleic acid 229-B1-002 was further characterized. The equilibrium binding constant $K_D$ of Type A hepcidin binding nucleic acid 229-B1-002 was determined by surface plasmon resonance measurement ($K_D$=1.47 nM determined with the apiegelmer sequence. FIGS. 10 and 11).

Furthermore the binding specificity/selectivity of Type A hepcidin binding nucleic acid 229-B1-002 was tested with the following hepcidin molecules: human hepcidin-25, cynomolgus hepcidin-25, mouse hepcidin-25, rat hepcidin-25, human hepcidin-22 and human hepcidin-20 (FIG. 10 and 11). Type A hepcidin binding nucleic acid 229-B 1-002 shows similar binding to human hepcidin-25, cynomolgus hepcidin-25, human hepcidin-22 and human hepcidin-20 and no binding to mouse hepcidin-25 and rat hepcidin-25 (FIGS. 10 and 11).

Except for Type A nucleic acid 229-E1-001, all Type A hepcidin binding nucleic acids according to the present invention comprise the first stretch Box A. In Type A hepcidin binding nucleic acid 229-D1-001 Box A is linked with its 3'-end to the 5'-end of the second terminal stretch (FIG. 2). In all other Type A hepcidin binding nucleic acids Box A is linked with its 5'-end to the 3'-end of the first terminal stretch (FIG. 1 to 4). Type A hepcidin binding nucleic acids comprising the Box A share the sequence 5' WAAAGUWGAR 3' (SEQ ID NO: 188) for Box A. Beside Type A hepcidin binding nucleic acids 229-C4-001/236-G2-001 and 236-D1-001 that comprise a sequence of 5' AAAAGUAGAA 3' (SEQ ID NO: 200) and 5' AAAAGUUGAA 3' (SEQ ID NO: 201), respectively, for Box A, the sequence of Box A of all other Type A hepcidin binding nucleic acids is 5' UAAAGUAGAG 3' (SEQ ID NO: 199).

Except for Type A hepcidin binding nucleic acid 236-D1-001 (see FIG. 2), all Type A hepcidin binding nucleic acids comprise a Box B with a sequence of 5' RGMGUGWK-AGUKC 3' (SEQ ID NO: 189). Type A hepcidin binding nucleic acid 236-D1-001 comprise a Box B that is different from the consensus sequence of Box of the other Type A hepcidin binding nucleic acids: 5' GGGAUAUAGUGC 3∝ (SEQ ID NO: 202). Because nucleic acid 229-E1-001 comprising no Box A does not or weakly bind to human hepcidin-25 as described supra, let assume, that beside Box B Box A is essential for binding to human hepcidin-25, in particular for high affinity binding to human hepcidin-25. In Type A hepcidin binding nucleic acid 229-D1-001 Box B is linked with its 5'-end to the 3'-end of the first terminal stretch (FIG. 2). In all other Type A hepcidin binding nucleic acids Box B—except for hepcidin binding nucleic acid 229-E1-001—is linked with its 3'-end to the 5'-end of the second terminal stretch (FIGS. 1, 3 and 4). Hepcidin binding nucleic acids with different sequences of Box B showed high binding affinity to human hepcidin-25:

a) 229-B1-001 and derivatives, 223-C5-001 and derivatives, 223-B5-001, 223-A5-001, 223-A3-001, 223-F5-001, 223-G4-001, 223-A4-001, 238-E2: 5' GGCGUGAUAGUGC 3' (SEQ ID NO: 203);

b) 229-B4-001, 229-C2-001, 229-E2-001: 5' GGAGUGUUAGUUC 3' (SEQ ID NO: 204);

c) 229-G1-001: 5' GGCGUGAGAGUGC 3' (SEQ ID NO: 205);

d) 229-C4-001, 236-G2-001: 5' AGCGUGAUAGUGC 3' (SEQ ID NO: 206)

e) 238-A1-001: 5' GGCGUGUUAGUGC 3' (SEQ ID NO: 207)

f) 236-D1-001: 5' GGGAUAUAGUGC 3' (SEQ ID NO: 202).

Hepcidin binding nucleic acids that comprise Box A and Box B are linked to each other by a linking stretch of nucleotides of 10 to 18 nucleotides. The linking stretch of nucleotides comprises in 5'→3' direction a first linking substretch of nucleotides, a second linking substretch of nucleotides and a third linking substretch of nucleotides, whereby preferably the first linking substretch of nucleotides and the third linking substretch of nucleotides optionally hybridize to each other, whereby upon hybridization a double-stranded structure is formed. However, such hybridization is not necessarily given in the molecule. If the nucleotides of the first linking substretch of nucleotides and third linking substretch of nucleotides hybridize to each other they are forming in between a loop of nucleotides (i.e. the second substretch) that do not hybridize to each other. The first substretch of nucleotides and the third substretch of nucleotides of the linking stretch of nucleotides of hepcidin binding nucleic acids comprise three (see 229-B1-001 and derivatives, 229-G2-001), four (see 223-C5-001 and derivatives, 223-B5-001, 223-A5-001, 223-A3-001, 223-F5-001, 223-G4-001, 223-A4-001, 229-C2-001, 229-B4-001, 229-E2-001, 238-A1-001, 238-E2-001, 237-A7-001), five (229-D1-001) or six (229-C4-001, 236-G2-001) nucleotides. Type A binding nucleic acid 236-D1-001 comprises a linking stretch of nucleotides of 18 nucleotides, whereby due to the specific sequence of said linking stretch of nucleotides the linking stretch of nucleotides can not be classified in a first linking substretch of nucleotides, a second linking substretch of nucleotides and a third linking substretch of nucleotides.

As shown for hepcidin binding nucleic acids 223-C5-001 and derivarives thereof, 223-B5-001, 223-A5-001, 223-A3-001, 223-F5-001, 223-G4-001, 238-E2-001 and 223-A4-001 the first substretch of the linking stretch of nucleotides comprises the sequence 5' GGAC 3' or 5' GGAU 3' or 5' GGA 3' and the third substretch of the linking stretch of nucleotides comprises the nucleotide sequence of 5' GUCC 3'. Other combinations of the first and the third substretch of the linking stretch of nucleotides are a) 5' GCAG 3' and 5' CUGC 3' (229-C2-001, 229-B4-001, 229-E2-001, 237-A7-001) or b) 5' GAC 3' and 5' GUC 3' (229-B1-001 and derivatives thereof, 229-G1-001) or c) 5' ACUUGU 3' and 5' GCAAGU 3' (229-C4-001) or d) 5' ACUUGU 3' and 5' GCAAGC 3' (236-G2-001) or e) 5' UCCAG 3' and 5' CUGGA 3' (229-D1-001) or f) 5' GGGC 3' and 5' GCCC 3' (238-A1-001).

As shown in FIGS. 1, 2, 3 and 4 the second substretch of the linking stretch of nucleotides comprises three to five nucleotides, whereby the different sequences are very heterogeneous: 5'CGAAA 3', 5' GCAAU 3', 5'GUAAU 3', 5' AAUU 3', 5' AUAAU 3', 5'AAUA 3', 5' CCA 3', 5' CUA 3', 5' UCA 3', 5' ACA 3', 5' GUU 3', 5' UGA 3' and 5' GUA 3'. The second substretch of the linking stretch of nucleotides of hepcidin binding nucleic acids can be summarized into the following generic sequences: 5' VBAAW 3', 5' AAUW 3' or 5' NBW 3'.

However, the hepcidin binding nucleic acids with the best binding affinity comprise the following sequences for the second substretch of the linking stretch of nucleotides:

a) 5' AAUU 3' (229-B1 and derivatives thereof)

b) 5' CCA 3' (223-C5 and derivatives thereof)

c) 5' CUA 3' (223-F5-001)

d) 5' UCA 3' (223-G4-001)

e) 5' AAUA 3' (229-G1-001).

As described supra, the nucleotide sequence of the first and the third substretch of the linking stretch are related to each other. Moreover, the nucleotide sequence of the second substretch of the linking stretch of nucleotides is related to a specific pair of the first and the third substretch of nucleotides leading to the following sequences or generic sequences of the linking stretch of nucleotides of hepcidin binding nucleic acids:

a) 5' GGACBYAGUCC 3' (SEQ ID NO: 208) (223-C5-001, 223-C5-002, 223-C5-006, 223-C5-007, 223-B5-001, 223-A5-001, 223-A3-001, 223-F5-001, 223-G4-001, 238-E2-001), preferably 5' GGACCCAGUCC 3' (SEQ ID NO: 193), 5' GGACCUAGUCC 3' (SEQ ID NO: 194) or 5' GGACUCAGUCC 3' (SEQ ID NO: 195) or 5' GGACGUAGUCC 3' (SEQ ID NO: 215), more preferably 5' GGACCCAGUCC 3' (SEQ ID NO: 193), 5' GGACCUAGUCC 3' (SEQ ID NO: 194) or 5' GGACUCAGUCC 3' (SEQ ID NO: 195); or b) 5' GGAUACAGUCC 3' (SEQ ID NO: 209) (223-A4-001); or c) 5' GCAGGYAAUCUGC 3' (SEQ ID NO: 210) (229-C2-001, 229-B4-001, 229-E2-001), preferably 5' GCAGGUAAUCUGC 3' (SEQ ID NO: 196) or 5' GCAGGCAAUCUGC 3' (SEQ ID NO: 197) , more preferably 5' GCAGGUAAUCUGC 3' (SEQ ID NO: 196); or d) 5' GACAAUWGUC 3' (SEQ ID NO: 211) (229-B1-001 and derivatives 229-G1-001), preferably 5' GACAAUUGUC 3' (SEQ ID NO: 198) or 5' GACAAUAGUC 3' (SEQ ID NO: 157) ; or e) 5' ACUUGUCGAAAGCAAGY 3' (SEQ ID NO: 216) (229-C4-001, 236-G2-001); or f) 5' UCCAGGUUCUGGA 3' (SEQ ID NO: 109) (229-D1-001); or g) 5' GGGCUGAGCCC 3' (SEQ ID NO: 190) (238-A1-001); or h) 5' GCAGAUAAUCUGC 3' (SEQ ID NO: 191) (237-A7-001); or i) 5'GGACCAGUCC 3'(SEQ ID NO: 192) (223-C5-008).

As mentioned before, the linking stretch of nucleotides of Type A binding nucleic acid 236-D1-001 can not be classified in a first linking substretch of nucleotides, a second finking substretch of nucleotides and a third linking substretch of nucleotides. However, the sequence of the linking stretch of nucleotides of Type A binding nucleic acid 236-D1-001 is 5' AUUUGUUGGAAUCAAGCA 3' (SEQ ID NO: 217) .

The first and second terminal stretches of nucleotides of Type A hepcidin binding nucleic acids comprise four (e.g.229-C4-001), five, (e.g. 223-C5-007), six (e.g.229-B1-001) or seven (e.g. 223-C5-001) nucleotides, whereby the stretches optionally hybridize with each other, whereby upon hybridization a double-stranded structure is formed. This double-stranded structure can consists of four to seven base-pairs. However, such hybridization is not necessarily given in the molecule.

Combining the first and second terminal stretches of nucleotides of all tested hepcidin binding nucleic acids the generic formula for the first terminal stretch of nucleotides and for the second terminal stretch of nucleotides are 5' $X_1X_2X_3$BKBK 3' (first terminal stretch of nucleotides) and 5' $MVVVX_4X_5X_6$ 3' (second terminal stretch of nucleotides), whereby $X_1$ is G or absent, $X_2$ is S or absent, $X_3$ is V or absent, $X_4$ is B or absent, $X_5$ is S or absent, and $X_6$ is C or absent, preferably a) $X_1$ is G, $X_2$ is S, $X_3$ is V, $X_4$ is B, $X_5$ is S, and $X_6$ is C or b) $X_1$ is absent, $X_2$ is S, $X_3$ is V, $X_4$ is B, $X_5$ is S, and $X_6$ is C or d) $X_1$ is G, $X_2$ is S, $X_3$ is V, $X_4$ is B, $X_5$ is S, and $X_6$ is absent or e) $X_1$ is absent, $X_2$ is S, $X_3$ is V, $X_4$ is B, $X_5$ is S, and $X_6$ is absent or f) $X_1$ is absent, $X_2$ is absent, $X_3$ is V, $X_4$ is B, $X_5$ is S, and $X_6$ is absent or g) $X_1$ is absent, $X_2$ is S, $X_3$ is V, $X_4$ is B, $X_5$ is absent, and $X_6$ is absent or f) $X_1$ is absent, $X_2$ is absent, $X_3$ is V or absent, $X_4$ is B or absent, $X_5$ is absent, $X_6$ is absent.

However, the hepcidin binding nucleic acids with the best binding affinity comprise the following combinations of first and second terminal stretches of nucleotides:

a) 223-C5-001, 223-F5-001, 223-G4-001: 5' GCACUCG 3' (first terminal stretch of nucleotides) and 5' CGAGUGC 3' (second terminal stretch of nucleotides);

b) 229-B1-002: 5' GCUGUG 3' (first terminal stretch of nucleotides) and 5' CACAGC 3' (second terminal stretch of nucleotides);

c) 229-B1-001, 229-G1-001: 5' CGUGUG 3' (first terminal stretch of nucleotides) and 5' CACACG 3' (second terminal stretch of nucleotides);

d) 229-D1-001: 5' CGUGCU 3' (first terminal stretch of nucleotides) and 5' AGCACG 3' (second terminal stretch of nucleotides);

e) 223-C5-006: 5' CGCGCG 3' (first terminal stretch of nucleotides) and 5' CGCGCG 3' (second terminal stretch of nucleotides)

f) 229-B1-007: 5' GCCGUG 3' (first terminal stretch of nucleotides) and 5' CACGGC 3' (second terminal stretch of nucleotides)

g) 229-B1-008: 5' GCGGUG 3' (first terminal stretch of nucleotides) and 5' CACCGC 3' (second terminal stretch of nucleotides)

h) 229-B1-009: 5' GCUGCG 3' (first terminal stretch of nucleotides) and 5' CGCAGC 3' (second terminal stretch of nucleotides)

i) 229-B1-010: 5' GCUGGG 3' (first terminal stretch of nucleotides) and 5' CCCAGC 3' (second terminal stretch of nucleotides)

j) 229-B1-011: 5' GCGGCG 3' (first terminal stretch of nucleotides) and 5' CGCCGC 3' (second terminal stretch of nucleotides).

In order to prove the functionality of hepcidin binding nucleic acids as spiegelmers, Type A hepcidin binding nucleic acids 223-C5-001 and 229-B1-002 were synthesized as spiegelmers comprising an Amino-group at its 5'-end. To the amino-modified spiegelmers 223-C5-001-5'-Amino and 229-B1-002-5'-Amino a 40 kDa PEG-moiety was coupled leading to Type A hepcidin binding nucleic acids 223-C5-001-5'-PEG and 229-B1-002-5'-PEG. Synthesis and PEGyation of the spiegelmer is described in Example 2.

The equilibrium binding constant $K_D$ of spiegelmers 223-C5-001-5'-PEG and 229-B1-002-5'-PEG were determined by surface plasmon resonance measurement (FIG. 12):

223-C5-001-5'-PEG: $K_D$=4.44 nM;
229-B1-002-5'-PEG: $K_D$=1.92 nM.

The spiegelmer 223-C5-001-5'-PEG was tested to inhibit/antagonize the function of hepcidin in vitro and in vivo. As shown in Example 5, Spiegelmer 223-C5-001-5'-PEG inhibits the hepcidin-induced downregulation of ferroportin in vitro. The applicability for in vivo use of the Spiegelmer 223-C5-001-5'-PEG was tested in an animal model for anaemia of inflammation, wherein the known properties of human hepcidin-25 to induce a serum iron decrease was uitilized (Example 5).

1.2 Type B Hepcidin Binding Nucleic Acids

As depicted in FIGS. 5 and 6, the Type B hepcidin binding nucleic acids comprise one central stretch of nucleotides defining a potential hepcidin binding motif.

In general, Type B hepcidin binding nucleic acids comprise at their 5'-end and the 3'-end terminal stretches of nucleotides: the first terminal stretch of nucleotides and the second terminal stretch of nucleotides. The first terminal stretch of nucleotides and the second terminal stretch of nucleotides can hybridize to each other, whereby upon hybridization a double-stranded structure is formed. However, such hybridization is not necessarily given in the molecule.

The three stretches of Type B hepcidin binding nucleic acids the first terminal stretch of nucleotides, the central stretch of nucleotides and the second terminal stretch of nucleotides can be differently arranged to each other: first terminal stretch of nucleotides—central stretch of nucleotides—second terminal stretch of nucleotides or second terminal stretch of nucleotides—central stretch of nucleotides—first terminal stretch of nucleotides.

The sequences of the defined stretches may be different between the Type B hepcidin binding nucleic acids which influences the binding affinity to human hepcidin, in particular human hepcidin-25. Based on binding analysis of the different hepcidin binding nucleic acids, the central stretch of nucleotides and its nucleotide sequences as described in the following is individually and more preferably in its entirety essential for binding to human hepcidin-25

The Type B hepcidin binding nucleic acids according to the present invention are shown in FIGS. 5 and 6. All of them were tested as aptamers or spiegelmers for their ability to bind human hepcidin-25, more precisely biotinylated human D-hepcidin-25 and biotinylated human L-hepcidin-25, respectively.

The Type B hepcidin binding nucleic acids 238-D2-001, 238-D4-001, 238-H1-001, 238-A2-001, 238-G2-001, 238-G4-001, 238-G3-001 were tested as aptamers in a competitive pull-down assay vs. Type A hepcidin binding nucleic acid 229-B1-001. Only Type B hepcidin binding nucleic acid 238-G4-001 showed reduced binding affinity in the competitive pull-down assay in comparison to Type A hepcidin binding nucleic acid 229-B1-001 (FIG. 5).

Type B hepcidin binding nucleic acids 238-D2-001, 238-D4-001, 238-H1-001, 238-A2-001, 238-G2-001 and 238-G3-001 showed improved binding affinity in comparison lo Type A hepcidin binding nucleic acid 229-B1-001 (FIG. 5). Type B hepcidin binding nucleic acid 238-D4-001 was further characterized. The equilibrium binding constant $K_D$ of spiegelmer 238-D4-001 was determined by surface plasmon resonance measurement ($K_D$=0.51 nM; FIG. 5).

The derivatives 238-D4-003, 238-D4-005, 238-D4-007, 238-D4-009, 238-D4-010, 238-D4-011, and 238-D4-013 of Type B hepcidin binding nucleic acid 238-D4-001 showed reduced binding affinity in a competitive pull-down assay (or shown by surface plasmon resonance measurement) in comparison to Type B hepcidin binding nucleic acid 238-D4-001

(FIG. 6). Indeed, hepcidin binding nucleic acids 238-D4-002, 238-D4-004, 238-D4-006, 238-D4-008 and 238-D4-012 showed in the same assay format similar binding to human hepcidin as 238-D4-001 (FIG. 6). The equilibrium binding constant $K_D$ of spiegelmers 238-D4-002, 238-D4-006 and 238-D4-008 were determined by surface plasmon resonance measurement. The calculated equilibrium binding constants of the derivatives of 238-D4-001 are in same range as shown for 238-D4-001 itself (FIG. 6).

Furthermore the binding selectivity of Type B hepcidin binding nucleic acids 238-D4-001 and 238-D4-008 were tested with the following hepcidin molecules: human hepcidin-25, cynomolgus hepcidin-25, marmoset hepcidin-25 (only for 238-D4-008), mouse hepcidin-25, rat hepcidin-25, human hepcidin-22 (not for 238-D4-008) and human hepcidin-20 (FIGS. 10 and 11). Type B hepcidin binding nucleic acid 238-D4-001 and 238-D4-008 shows similar binding to human hepcidin-25, human hepcidin-22, human hepcidin-20 and cynomolgus hepcidin-25, weaker binding to marmoset hepcidin-25 and no binding to mouse hepcidin-25 and rat hepcidin-25, (FIGS. 10 and 11).

The Type B hepcidin binding nucleic acids according to the present invention share (he sequence 5' RKAUGG-GAKUAAGUAAAUGAGGRGUWGGAGGAAR 3' (SEQ ID NO: 182) or 5' RKAUGGGAKAAGUAAAUGAGGR-GUWGGAGGAAR 3' (SEQ ID NO: 183) for the central stretch of nucleotides. Type B hepcidin binding nucleic acid 238-D4-001 and its derivatives that showed the same binding affinity to human hepcidin-25 share the consensus sequence comprises the sequence 5' GUAUGGGA-UUAAGUAAAUGAGGAGUUGGAGGAAG 3' (SEQ ID NO: 184) for the central stretch of nucleotides.

The first and second terminal stretches of nucleotides of Type B hepcidin binding nucleic acids comprise five (238-D4-004, 238-D4-005, 238-D4-008, 238-D4-009), six (238-D4-002, 238-D4-003, 238-D4-006, 238-D4-007, 238-D4-010, 238-D4-011, 238-D4-012, 238-D4-013) or eight (238-D2-001, 238-D4-001, 238-H1-001, 238-A2-001, 238-G2-001, 238-G4-001, 238-G3-001) nucleotides, whereby the stretches optionally hybridize with each other, whereby upon hybridization a double-stranded structure is formed. This double-stranded structure can consists of five to eight base-pairs. However, such hybridization is not necessarily given in the molecule.

Combining the first and second terminal stretches of nucleotides of all tested Type B hepcidin binding nucleic acids the generic formula for the first terminal stretch of nucleotides and for the second terminal stretch of nucleotides are 5' $X_1X_2X_3$SBSBC3' (first terminal stretch of nucleotides) and 5' GVBVB$X_4X_5X_6$ 3' (second terminal stretch of nucleotides), wherein $X_1$ is A or absent, $X_2$ is G or absent, $X_3$ is B or absent, $X_4$ is S or absent, $X_5$ is C or absent, and $X_6$ is U or absent, preferably a) $X_1$ is A, $X_2$ is G, $X_3$ is B, $X_4$ is S, $X_5$ is C, and $X_6$ is U or b) $X_1$ is absent, $X_2$ is G, $X_3$ is B, $X_4$ is S, $X_5$ is C, and $X_6$ is U or c) $X_1$ is A, $X_2$ is G, $X_3$ is B, $X_4$ is S, $X_5$ is C, and $X_6$ is absent or d) $X_1$ is absent, $X_2$ is G, $X_3$ is B, $X_4$ is S, $X_5$ is C, and $X_6$ is absent or e) $X_1$ is absent, $X_2$ is absent, $X_3$ is B, $X_4$ is S, $X_5$ is C, and $X_6$ is absent or f) $X_1$ is absent, $X_2$ is G, $X_3$ is B, $X_4$ is S, $X_5$ is absent, and $X_6$ is absent or g) $X_1$ is absent, $X_2$ is absent, $X_3$ is B or absent, $X_4$ is S or absent, $X_5$ is absent, and $X_6$ is absent.

However, the best binding Type B hepcidin binding nucleic acids comprise the following combinations of first and second terminal stretches of nucleotides:

a) 238-D2-001: 5' AGCGUGUC 3' (first terminal stretch of nucleotides) and 5' GGUGCGCU 3' (second terminal stretch of nucleotides).

b) 238-D4-001: 5' AGCGUGUC 3' (first terminal stretch of nucleotides) and 5' GGCAUGCU 3' (second terminal stretch of nucleotides).

c) 238-H1-001: 5' AGUGUGUC 3' (first terminal stretch of nucleotides) and 5' GAUGCGCU 3' (second terminal stretch of nucleotides).

d) 238-A2-001: 5' AGUGUGUC 3' (first terminal stretch of nucleotides) and 5' GGCAUGCU 3' (second terminal stretch of nucleotides).

e) 238-G2-001: 5' AGCGUGCC 3' (first terminal stretch of nucleotides) and 5' GGUGCGCU 3' (second terminal stretch of nucleotides).

f) 238-G3-001: 5' AGCGCGCC 3' (first terminal stretch of nucleotides) and 5' GGCGCGCU V (second terminal stretch of nucleotides).

g) 238-D4-002: 5' GCGCGC 3' (first terminal stretch of nucleotides) and 5' GCGCGC 3' (second terminal stretch of nucleotides)

h) 238-D4-006: 5'GGUGUC 3' (first terminal stretch of nucleotides) and 5' GGCAUC 3' (second terminal stretch of nucleotides)

i) 238-D4-012: 5' GGCGUC 3' (first terminal stretch of nucleotides) and 5' GGCGCC 3' (3'-terminal stretch of nucleotides)

j) 238-D4-008: 5' GCGCC 3' (first terminal stretch of nucleotides) and 5' GGCGC 3' (second terminal stretch of nucleotides)

k) 238-D4-004: 5' GGCGC 3' (first terminal stretch of nucleotides) and 5' GCGCC 3' (second terminal stretch of nucleotides)

In order to prove the Functionality of Type B hepcidin binding nucleic acids as spiegelmers, hepcidin binding nucleic acids 238-D4-002 and 238-D4-008 were synthesized as spiegelmer comprising an Amino-group at its 5'-end. To the amino-modified spiegelmers 238-D4-002-5'-Amino and 238-D4-008-5'-Amino a 40 kDa PEG-moiety was coupled leading to hepcidin binding nucleic acids 238-D4-002-5'-PEG and 238-D4-008-5'PEG. Synthesis and PEGyation of the spiegelmer is described in Example 2.

The equilibrium binding constant $K_D$ of spiegelmers 238-D4-002-5'-PEG and 238-D4-008-5'-PEG were determined by surface plasmon resonance measurement (FIG. 12):

238-D4-002-5'-PEG: 0.53 nM,

238-D4-008-5'-PEG: 0.64 nM.

The spiegelmer 238-D4-008-5'-PEG was tested to inhibit/antagonize the function of hepcidin in vitro and in vivo. As shown in Example 5, Spiegelmer 238-D4-008-5'-PEG inhibits the hepcidin-induced downregulation of ferroportin in vitro. The applicability for in vivo use of the spiegelmer 238-D4-008-5'-PEG was tested in an animal model for anaemia of inflammation, wherein the known properties of human hepcidin-25 to induce a serum iron decrease was uitilized (Example 5, FIG. 20). Moreover, Spiegelmer 238-D4-008-5'-PEG was tested in another animal model (cynomolgus monkey) for anaemia of inflammation, whereby IL-6 induces hepcidin secretion subsequently resulting in anemia in non-human primates. Within the experiment human IL-6 leads a reduction of serum iron concentration (Example 6, FIG. 21).

1.3 Type C Hepcidin Binding Nucleic Acids

As depicted in FIGS. 7 and 8 the Type C hepcidin binding nucleic acids comprise one central stretch of nucleotides defining a potential hepcidin binding motif.

In general, Type C hepcidin binding nucleic acids comprise at their 5end and the 3'-end terminal stretches: the first terminal stretch of nucleotides and the second terminal stretch of nucleotides. The first terminal stretch of nucleotides and the second terminal stretch of nucleotides can hybridize to each other, whereby upon hybridization a double-stranded structure is formed. However, such hybridization is not necessarily given in the molecule.

The three stretches of nucleotides of Type C hepcidin binding nucleic acids first terminal stretch of nucleotides, central stretch of nucleotides and second terminal stretch of nucleotides can be differently arranged to each other: first terminal stretch of nucleotides—central stretch of nucleotides—second terminal stretch of nucleotides or second terminal stretch of nucleotides13 central stretch of nucleotides13 first terminal stretch of nucleotides.

The sequences of the defined stretches may be different between the Type C hepcidin binding nucleic acids which influences the binding affinity to human hepcidin, in particular human-hepcidin-25. Based on binding analysis of the different Type C hepcidin binding nucleic acids, the central stretch of nucleotides and its nucleotide sequences as described in the following is individually and more preferably in its entirety essential for binding to human hepcidin.

Type C hepcidin binding nucleic acids according to the present invention are shown in FIGS. 7 and 8. All of them were tested as aptamers or spiegelmers for their ability to bind human hepcidin-25, more precisely biotinylated human D-hepcidin-25 and biotinylated human L-hepcidin-25.

The Type C hepcidin binding nucleic acids 238-C4-001, 238-E3-001, 238-F2-001, 238-A4-001 and 238-E1-001 were tested as aptamers in a competitive pull-down assay vs. Type A hepcidin binding nucleic acid 229-B1-001. The Type C hepcidin binding nucleic acids showed improved binding affinity in comparison to Type A hepcidin binding nucleic acid 229-B1-001 (FIG. 7). Type C hepcidin binding nucleic acid 238-C4-001 was further characterized. The equilibrium binding constant $K_D$ of the spiegelmer 238-C4-001 was determined by surface plasmon resonance measurement ($K_D$=0.9 nM; FIG. 7).

The derivatives 238-C4-003, 238-C4-004, 238-C4-005, 238-C4-007, 238-C4-008, 238-C4-009, 238-C4-011, 238-C4-012, 238-C4-013, 238-C4-014, 238-C4-024, 238-C4-025 and 238-C4-062 of Type C hepcidin binding nucleic acid 238-C4-001 showed reduced binding affinity in a competitive pull-down assay or by plasmon resonance measurement in comparison to hepcidin binding nucleic acid 238-C4-001 or 238-C4-006 (FIG. 8). Nucleic acid 238-C4-063 showed no binding to hepcidin. Indeed, hepcidin binding nucleic acids 238-C4-002, 238-C4-006 and 238-C4-010 showed in the same assay similar binding to human hepcidin-25 as 238-C4-001 (FIG. 8). The equilibrium binding constant $K_D$ of Spiegelmers 238-C4-002 and 238-C4-006 were determined by surface plasmon resonance measurement. The calculated equilibrium binding constants of the derivatives of 238-C4-001 are in same range as shown for 238-C4-001 itself (FIG. 8).

Furthermore the binding specificty/selectivity of Type C hepcidin binding nucleic acid 238-C4-006 was tested with the following hepcidin molecules: human hepcidin-25, cynomolgus hepcidin-25, marmoset hepcidin-25, mouse hepcidin-25, rat hepcidin-25, human hepcidin-22 and human hepcidin-20 (FIGS. 10 and 11). Type C hepcidin binding nucleic acid 238-C4-006 shows similar binding to human hepcidin-25, human hepcidin-22, human hepcidin-20 and cynomolgus hepcidin-25 and no binding to marmoset hepcidin-25, mouse hepcidin-25 and rat hepcidin-25 (FIGS. 10 and 11).

Except for nucleic acid 238-C4-063 that shows no binding to hepcidin-25, the Type C hepcidin binding nucleic acids according to the present invention share the sequence 5' GRCRGCCGGVGGACACCAUAUACAGACUACKAUA 3' (SEQ ID NO: 185) or 5' GRCRGCCGGVAGGACAC-CAUAUACAGACUACKAUA 3' (SEQ ID NO: 218) for the central stretch of nucleotides. Type C hepcidin binding nucleic acid 238-C4-001 and its derivatives 238-C4-002, 238-C4-005, 238-C4-010 and Type C hepcidin binding nucleic acids 238-E3-001, 238-F2-001, 238-A4-001, 238-E1-001 that all showed the same binding affinity share the consensus sequence 5' GRCRGCCGGGGGACAC-CAUAUACAGACUACKAUA 3' (SEQ ID NO: 214), and preferably the sequence 5' GACAGCCGGGGGACAC-CAUAUACAGACUACGAUA 3' (SEQ ID NO: 187).

The first and second terminal stretches of nucleotides of Type C hepcidin bindig nucleic acids comprise four (238-C4-004, 238-C4-011, 238-C4-012, 238-C4-013, 238-C4-014), five (238-C4-003, 238-C4-005, 238-C4-006, 238-C4-007, 238-C4-008, 238-C4-009, 238-C4-010, 238-C4-024, 238-C4-025, 238-C4-062), six (238-C4-002) or seven (238-C4-001, 238-E3-001, 238-F2-001, 238-A4-001, 238-E1-001) nucleotides, whereby the stretches optionally hybridize with each other, whereby upon hybridization a double-stranded structure is formed. This double-stranded structure can consists of four to seven basepairs. However, such hybridization is not necessarily given in the molecule.

Combining the first and second terminal stretches of nucleotides of all tested Type C hepcidin binding nucleic acids the generic formula for the first terminal stretch of nucleotides and for the second terminal stretch of nucleotides are 5' $X_1X_2X_3$SBSN3' (first terminal stretch of nucleotides) and 5' NSVS$X_4X_5X_6$ 3' (second terminal stretch of nucleotides), wherein $X_1$ is A or absent, $X_2$ is G or absent, $X_3$ is R or absent, $X_4$ is Y or absent, $X_5$ is C or absent, $X_6$ is U or absent, preferably a) $X_1$ is A, $X_2$ is G, $X_3$ is R, $X_4$ is Y, $X_5$ is C, and $X_6$ is U or b) $X_1$ is absent, $X_2$ is G, $X_3$ is R, $X_4$ is Y, $X_5$ is C, and $X_6$ is U or c) $X_1$ is A, $X_2$ is G, $X_3$ is R, $X_4$ is Y, $X_5$ is C, and $X_6$ is absent or d) $X_1$ is absent, $X_2$ is G, $X_3$ is R, $X_4$ is Y, $X_5$ is C, and $X_6$ is absent or e) $X_1$ is absent, $X_2$ is absent, $X_3$ is R, $X_4$ is Y, $X_5$ is C, and $X_6$ is absent or f) $X_1$ is absent, $X_2$ is G, $X_3$ is R, $X_4$ is Y, $X_5$ is absent, and $X_6$ is absent or g) $X_1$ is absent, $X_2$ is absent, $X_3$ is R or absent, $X_4$ is Y or absent, $X_5$ is absent, and $X_6$ is absent.

However, the best binding Type C hepcidin binding nucleic acids comprise the following combinations of first and 3'-terminal stretches of nucleotides:

a) 238-C4-001, 238-E3-001: 5' AGGCUCG 3' (first terminal stretch of nucleotides) and 5' CGGGCCU 3' (second terminal stretch of nucleotides), b) 238-F2-001: 5' AGGCCCG 3' (first terminal stretch of nucleotides) and 5' CGGGCCU 3' (second terminal stretch of nucleotides), c) 238-A4-001: 5' AGGCUUG 3' (first terminal stretch of nucleotides) and 5' CGAGCCU 3' (second terminal stretch of nucleotides), d) 238-E1-001: 5' AGACUUG 3' (first terminal stretch of nucleotides) and 5' CGAGUCU 3' (second terminal stretch of nucleotides), e) 238-C4-002: 5GGCUCG 3' (first terminal stretch of nucleotides) and 5'CGGGCC3' (second terminal stretch of nucleotides), f) 238-C4-006: 5' GGCCG 3' (first terminal stretch of nucleotides) and 5' CGGCC 3' (second terminal stretch of nucleotides)

g) 238-C4-010: 5' GCGCG 3' (first terminal stretch of nucleotides) and 5' CGCGC 3' (second terminal stretch of nucleotides).

In order to prove the functionality of hepcidin binding nucleic acids as spiegelmers, hepcidin binding nucleic acid 238-C4-006 was synthesized as spiegelmer comprising an Amino-group at its 5'-end. To the amino-modified Spiegelmers 238-C4-006-5'-Amino a 40 kDa PEG-moiety was coupled leading to Type C hepcidin binding nucleic acid 238-C4-006-5'-PEG. Synthesis and PEGyation of the spiegelmer is described in Example 2.

The equilibrium binding constant $K_D$ of spiegelmer 238-C4-006-5'-PEG was determined by surface plasmon resonance measurement (FIG. 12): 0.76 nM.

1.4 Other Hepcidin Binding Nucleic Acids

As depicted in FIG. 9 other hepcidin binding nucleic acids that are not related to Type A, B and C hepcidin binding nucleic acids are shown. The binding affinities of these hepcidin nucleic acids were determined by Plasmon resonsace meassurement as well as by competitive binding experiments vs. Type A hepcidin binding nucleic acid 229-G1-001. All nucleic acids showed weaker binding affinity than Type A hepcidin binding nucleic acid 229-G1-001 (FIG. 9).

EXAMPLE 2

Synthesis and Derivatization of Aptamers and Spiegelmers

Small Scale Synthesis

Aptamers (D-RNA nucleic acids) and spiegelmers (L-RNA nucleic acids) were produced by solid-phase synthesis with an ABI 394 synthesizer (Applied Biosystems, Foster City, Calif., USA) using 2'TBDMS RNA phosphoramidite chemistry (Damha and Ogilvie, 1993). rA(N-Bz)-, rC(Ac)-, rG(N-ibu)-, and rU-phosphoramidites in the D- and L-configuration were purchased from ChemGenes, Wilmington, Mass. Aptamers and spiegelmers were purified by gel electrophoresis.

Large Scale Synthesis Plus Modification

Spiegelmers were produced by solid-phase synthesis with an ÄktaPilot100 synthesizer (Amersham Biosciences; General Electric Healthcare, Freiburg) using 2'TBDMS RNA phosphoramidite chemistry (Damha and Ogilvie, 1993). L-rA(N-Bz)-, L-rC(Ac)-, L-rG(N-ibu)-, and L-rU-phosphoramidites were purchased from ChemGenes, Wilmington, Mass. The 5'-amino-modifier was purchased from American International Chemicals Inc. (Framingham, Mass., USA). Synthesis of the unmodified or 5'-Amino-modified spiegelmers were started on L-riboG, L-riboC, L-riboA or L-riboU modified CPG pore size 1000 Å (Link Technology, Glasgow, UK. For coupling (15 min per cycle), 0.3 M benzylthiotetrazole (CMS-Chemicals, Abingdon, UK) in acetonitrile, and 3.5 equivalents of the respective 0.1 M phosphoramidite solution in acetonitrile was used. An oxidation-capping cycle was used. Further standard solvents and reagents for oligonucleotide synthesis were purchased from Biosolve (Valkenswaard, NL). The spiegelmers were synthesized DMT-ON; after deprotection, it was purified via preparative RP-HPLC (Wincott et al., 1995) using Source 15RPC medium (Amersham). The 5'DMT-group was removed with 80% acetic acid (30 min at RT). Subsequently, aqueous 2 M NaOAc solution was added and the spiegelmers was desalted by tangential-flow Filtration using a 5 K regenerated cellulose membrane (Millipore, Bedford, Mass.).

PEGylation of Spiegelmers

In order to prolong the spiegelmer's plasma residence time in vivo, spiegelmers was covalently coupled to a 40 kDa polyethylene glycol (PEG) moiety at 5'-end.

5'-PEGylation of Spiegelmers

For PEGylation (for technical details of the method for PEGylation see European patent application EP 1 306 382), the purified 5'-amino modified spiegelmers were dissolved in a mixture of H2O (2.5 ml), DMF (5 ml), and buffer A (5 ml; prepared by mixing citric acid.$H_2O$ [7 g], boric acid [3.54 g], phosphoric acid [2.26 ml], and 1 M NaOH [343 ml] and adding water to a final volume of 1 l; pH=8.4 was adjusted with 1 M HCl).

The pH of the spiegelmer solution was brought to 8.4 with 1 M NaOH. Then, 40 kDa PEG-NHS ester (Jenkem Technology, Allen, Tex., USA) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M tri ethyl ammonium acetate in H2O) and heated to 95° C. for 15 min. The PEGylated Spiegelmer was then purified by RP-HPLC with Source 15RPC medium (Amersham), using an acetonitrile gradient (buffer B; buffer C: 0.1 M triethylammonium acetate in acetonitrile). Excess PEG eluted at 5% buffer C, PEGylated spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 3

Determination of binding Constants to Hepcidin (Pull-Down Assay)

Direct Pull-Down Assay

The affinity of hepcidin binding nucleic acids was measured as aptamers (D-RNA nucleic acids) to biotinylated human D-Hepcidin-25 (SEQ.ID.No. 7) in a pull down assay format at 37° C. Aptamers were 5'-phosphate labeled by T4 polynucleotide kinase (Invitrogen, Karlsruhe, Germany) using [γ-$^{32}$P]-labeled ATP (Hartmann Analytic, Braunschweig, Germany). The specific radioactivity of labeled aptamers was 200,000-800,000 cpm/pmol. Aptamers were incubated after de- and renaturation at 20 pM concentration at 37° C. in selection buffer (20 mM Tris-HCl pH 7.4; 137 mM NaCl; 5 mM KCl; 1 mM $MgCl_2$; 1 mM $CaCl_2$; 0.1% [w/vol] Tween-20) together with varying amounts of biotinylated human D-hepcidin for 2-12 hours in order to reach equilibrium at low concentrations. Selection buffer was supplemented with 10 µg/ml human serum albumin (Sigma-Aldrich, Steinheim, Germany), and 10 µg/ml yeast RNA (Ambion, Austin, USA) in order to prevent adsorption of binding partners to surfaces of used plasticware or the immobilization matrix. The concentration range of biotinylated human D-hepcidin was set from 32 pM to 500 nM; total reaction volume was 1 ml. Biotinylated human D-hepcidin and complexes of aptamer and biotinylated human D-hepcidin were immobilized on 6 μl NeutrAvidin or Streptavidin Ultralink Plus particles (Thermo Scientific, Rockford, USA) which had been preequilibrated with selection buffer and resuspended in a total volume of 12 μl. Particles were kept in suspension for 30 min at the respective temperature in a thermomixer. Immobilized radioactivity was quantitated in a scintillation counter after detaching the supernatant and appropriate washing. The percentage of binding was plotted against the concentration of biotinylated human D-hepcidin and dissociation constants were obtained by using software algorithms (GRAFIT; Erithacus Software; Surrey U.K.) assuming a 1:1 stoichiometry.

Aptamer Competitive Pull-Down Assay

In order to compare different aptamers of hepcidin binding nucleic acids, a competitive ranking assay was performed. For this purpose the most affine aptamer available was radioactively labeled (see above) and served as reference. After de- and renaturation it was incubated at 37° C. with biotinylated human D-hepcidin in 0.8 ml selection buffer at conditions that resulted in around 5-10 % binding to the biotinylated human D-hepcidin-25 after immobilization on NeutrAvidin agarose or Streptavidin Ultralink Plus (both from Thermo Scientific) and washing without competition. An excess of de- and renatured non-labeled D-RNA aptamer variants was added to different concentrations (e.g. 10, 50 and 250 nM) with the labeled reference aptamer to parallel binding reactions. The aptamers to be tested competed with the reference aptamer for target binding, thus decreasing the binding signal in dependence of their binding characteristics. The aptamer that was found most active in this assay could then serve as a new reference for comparative analysis of further aptamer variants.

Spiegelmer Competitive Pull-Down Assay

In addition, the competitive pull-down assay was performed to analyse the affinity of hepcidin binding spiegelmers. For this purpose spiegelmers binding to biotinylated human L-hepcidin-25 were applied. The addition of two additional guanosine residues in the D-configuration at the 5'-end of the spiegelmers enabled the radioactive labeling of the spiegelmers by T4 polynucleotide kinase (see above). After de- and renaturation the labeled spiegelmer and a set of 5-fold dilutions ranging from 0.032 to 500 nM of competitor molecules (such different species of hepcidin, truncated versions of hepcidin or spiegelmers; see below) were incubated with a constant amount of biotinylated human L-hepcidin in 0.8 ml selection buffer at 37° C. for 2-4 hours. The chosen peptide concentration should cause final binding of approximately 5-10% radiolabeled Spiegelmer at the lowest competitor concentration. In one version of the competitive pull-down assay an excess of de- and renatured non-labeled L-RNA spiegelmer variants served as competitors, whereas unmodified as well as PEGylated forms were tested. In another assay approach non-biotinylated L-hepcidin-25 from various species (such as human L-hepcidin-25, cynomolgus L-hepcidin-25, marmoset L-hepcidin-25 or rat L-hepcidin-25) or non-biotinylated N-terminal truncated L-hepcidin-20 and L-hepcidin-22 competed against the biotinylated L-hepcidin for spiegelmer binding. After immobilization of biotinylated L-hepcidin-25 and the bound Spiegelmers on 1.5-3 μl Streptavidin Ultralink Plus matrix (Thermo Scientific, Rockford, USA), washing and scintillation counting (see above), the normalized percentage of bound radiolabeled Spiegelmer was plotted against the corresponding concentration of competitor molecules. The resulting dissociation constant was calculated employing the GraFit Software.

EXAMPLE 4

Binding Analysis by Surface Plasmon Resonance Measurement

The Biacore 2000 instrument (Biacore AB, Uppsala, Sweden) was used to analyze binding of the aptamers of the hepcidin binding nucleic acids against biotinylated human D-hepcidin-25 and of the spiegelmers of the hepcidin binding nucleic acids against biotinylated human L-hepcidin-20, as well as human, rat and mouse L-hepcidin 25.

The instrument was set to a enduring temperature of 37° C. Before the start of each experiment the Biacore was cleaned using the DESORB method according to the manufacturer's instructions. After docking a maintenance chip, the instrument was consecutively primed with DESORB solution 1 (0.5% sodium dodecyl sulphate, SDS), DESORB solution 2 (50 mM glycine, pH 9.5) and finally degassed MilliQ water. Subsequently the SANATIZE method was run with 0.1M NaOCl and the system was primed afterwards with MilliQ water.

The biotinylated human D-hepcidin 25, human L-hepcidin 20, as well as human, rat and mouse L-hepcidin 25 (all peptides from BACHEM, custom synthesis) were dissolved in water with 1 mg/ml fatty-acid free BSA at a concentration of 1 mM in a screw lock vial and stored at 4° C. until use.

After docking a sensor chip with a carboxymethylated dextran matrix (Sensor Chip CM5, GE, BR-1000-14), the Biacore instrument was primed with MilliQ water followed by HBS-EP buffer (0.01 M HEPES buffer [pH 7.4], 0.15 M NaCl, with 0.005% Surfactant P20; GE, BR-1001-88) and equilibrated until a stable baseline was observed. The flow cells (FCs) were immobilized beginning from flow cell 4 to flow cell 1 to avoid carry-over of peptides to other flow cells.

100 μl of a 1:1 mixture of 0.4M EDC (1-ethy/-3-(5-dimethylaminopropyl) carbodiimide in $H_2O$; GE, BR-1000-50) and 0.1M NHS (N-hydroxysuccinimide in $H_2O$; GE, BR-1000-50) were injected using the QUICKINJECT command at a flow of 10 μl/min. Activation of the flow cell was monitored by an increase in RU after NHS/EDC injection (typically 500-600 RU for CM5 chips). Soluble Neutravidin was dissolved in water to a concentration of 1 mg/ml, diluted in HBS-EP to 50 82 g/ml and subsequently injected using the MANUALINJECT command at a flow of 10 μl/min. The maximal observed amount of covalently immobilized Neutravidin was about 10.000-15.000 RU. The flow cells were blocked with a injection 70 μl of 1 M ethanolamine hydrochloride (GE, BR-1000-50) at a flow of 10 μl/min; typically non-covalently bound peptide/protein is removed by this procedure. Non-covalently coupled Neutravidin was removed by an injection of 10-30 μl of a 50 mM NaOH solution. Biotinylated human D-hepcidin 25, human L-hepcidin 20, as well as human, rat and mouse L-hepcidin 25 was directly diluted to a final concentration of 10-20 nM in HBS-EP buffer and vortexed immediately. 1000 μl of this sample was transferred to Ø 9 mm glass vial (Glass Vials, Ø 9 mm, GE, BR-1002-07) and injected using the MANUALINJECT command at a flow of 10 μl/min. For binding experiments up to 5000 response units (RU) of biotinylated human D-hepcidin 25, human L-hepcidin 20, as well as human, rat and mouse L-hepcidin 25 and for kinetic evaluations 500-1500 RU were immobilized on the flow cell. Subsequently the flow cell was washed with 1 M NaCl (Ambion, Cat.No.AM9759) to avoid carry over of biotinylated human D-hepcidin 25, human L-hepcidin 20, as well as human, rat and mouse L-hepcidin 25 due to unspecific interaction of biotinylated human D-hepcidin 25, human L-hepcidin 20, as well as human, rat and mouse L-hepcidin 25 with the Biacore tubing and other surfaces. FC1 served as blocked control flow cell.

Finally all sensor flow cells (beginning from FC1 to FC4) were blocked by injecting 20 μl of a saturated biotin solution (Biotin, Sigma-Aldrich B-4501 Lot 68H1373) diluted 1:10 in HBS-EP buffer at a flow of 20 μl/ min. The sensor chip was primed twice with degased running buffer (20 mM Tris pH 7.4; 150 mM NaCl; 5 mM KCl, 1 mM $MgCl_2$, 1 mM $CaCl_2$ and 0.1% Tween20) and equilibrated at 30 μl/min until the baseline appeared stable.

Typically for analytical purpose, the aptamers/spiegefmers of hepcidin binding nucleic acids were diluted in water to a stock concentration of 100 μM (quantification by UV measurement), heated up to 95° C. for 30 seconds in a water bath or thermo mixer and snap cooled on ice to assure a homogenous dissolved solution.

Kinetic parameters and dissociation constants were evaluated by a series of aptamer injections at concentrations of 1000, 500, 250, 125, 62.5, 31.25, 15.63 , 7.8, 3.9 and 0 nM diluted in running buffer. In all experiments, the analysis was performed at 37° C. using the Kinject command defining an association time of 360 and a dissociation time of 360 seconds at a flow of 30 μl/ min. The assay was double referenced, whereas FC1 served as (blocked) surface control (bulk contribution of each aptamer concentration) and a series of buffer injections without analyte determined the bulk contribution of the buffer itself Data analysis and calculation of dissociation constants (KD) was done with the BIAevaluation 3.0 software (BIACORE AB, Uppsala, Sweden) using the Langmuir 1:1 stochiometric fitting algorithm.

EXAMPLE 5

Inhibition of Human and Mouse Hepcidin-Induced Downregulation of Ferroportin by Hepcidin-Binding Spiegelmers Method J774.1 cells (mouse monocytes-macrophages, obtained from DSMZ, Braunschweig) are cultivated at 37° C. and 5% $CO_2$ in Dulbecco's modified Eagle's medium (DMEM) with Glutamax (Invitrogen, Karlsruhe, Germany) which contains 10% fetal calf serum, 100 units/ml penicillin and 100 μg/ml streptomycin. For the experiments cells were seeded in 12-well plates at a density of $7.3 \times 10^5$ cells/well ($2 \times 10^5$ cells/$cm^2$) in 2 ml medium and cultivated for several hours at 37° C. and 5% $CO_2$. After cell attachment cells were loaded with iron by addition of 20 μl of a Fe-NTA-solution prepared by mixing 1 part 0.3 M $FeCl_3$ in $H_2O$ with 2 parts 0.3 M NTA (nitrilotriacetate) in $H_2O$ followed by 1:10 dilution with DMEM. Cells are cultivated overnight as described. The next day stimulation solutions were prepared in DMEM, containing human hepcidin and when indicated spiegermei (see below the spiegelmers that were added) each at 5× the intended final concentration and preincubated at 37° C. for 30 min. 0.5 ml of the solutions were added to each well of the 12-well plate. After 3 hours stimulation, the medium was removed and the cells were quickly washed once with 1 ml ice-cold phosphate buffered saline (PBS). Cells were then scraped off the wells in 1 ml cold PBS and collected in pre-cooled Eppendorf tubes. After centrifugation for 5 min at 500 g at 4° C. the supernatants were removed and the pellets resuspended in 75 μl of lysis buffer (Tris/HCl, pH 7.5, 150 mM NaCl, 1 mM EDTA, 1% Triton X-100 and protease-inhibitors (protease inhibitor cocktail tablets, Roche #11873580001). Cell suspensions were frozen on dry ice, thawed, thoroughly vortexed and centrifuged for 10 min at 1000 g at 4° C. The lysate supernatants were collected and stored at −80° C. until further analysis.

Protein determination was performed using the bicinchoninic acid method. Lysate amounts containing 20 μg protein were mixed with 2× sample buffer (125 mM Tris/HCl, pH 6.8; 20% glycerol; 4% SDS; 0.02% bromophenolblue) and incubated at 37° C. for 10 min. Proteins were separated on 10% SDS-polyacrylamide gels and then transferred by electroblotting onto HybondECL nitrocellulose or Hybond-P PVDF membranes (GE Healthcare, Munich, Germany). After blotting, the membranes were stained with Ponceau-red (0.2% in 3% trichloroacetic acid) for control of protein loading and transfer. Ferroportin was detected with a rabbit anti-mouse ferroportin antibody (Alpha Diagnostics, #MTP11-A) and a anti-rabbit-IgG-HRP-conjugate (New England Biolabs, Frankfurt a.M., Germany) using LumiGlo® chemiluminescent reagent (CellSignaling Technology, Frankfurt a.M., Germany) and Hyperfilm™ ECL chemiluminescence films (GE Healthcare, Munich, Germany).

Result

Lysates obtained from J774.1 cells after stimulation with human hepcidin or hepcidin+the respective spiegelmer were separated by SDS-gel electrophoresis and analysed by Western Blot using an antibody against mouse ferroportin.

Treatment of J774.1 cells with Fe/NTA led to a substantial up-regulation of ferroportin expression. This effect is considerably reversed by stimulation of cells with 100 nM human hepcidin-25 for 3 hours. This hepcidin effect is blocked when hepcidin was pre-incubated with spiegelmers 226-C5-001-5'-PEG, 238-D4-008-5'-Amino and 238-D4-008-5'-PEG (=NOX-H94).

FIG. 17A: Ferroportin (arrowhead), which is barely detectable in untreated cells (lane 1), is up-regulated by treatment with Fe/NTA (lanes 2, 3). 100 nM human hepcidin-25 (HEP) lead to down regulation of ferroportin (lanes 4, 5) and this effect can be strongly inhibited by spiegelmer 226-C5-001 (C5-PEG) (lanes 6, 7).

Figure 17B:
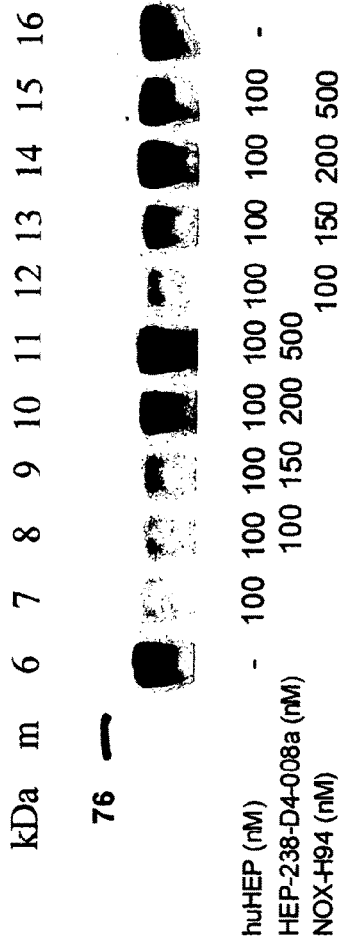

FIG. 17B: Human hepcidin leads to down regulation of ferroportin in Fe/NTA treated J774.1 cells (lanes 6, 7). This effect of human hepcidin-25 can be strongly inhibited by spiegelmer NOX-H94 (lanes 12 -15) and by spiegelmer HEP-238-D4-008a, which is the amino-modified oligonucleotide intermediate of 238-D4-008-5'-PEG (=NOX-H94) (lanes 8-11).

EXAMPLE 6

Activity of a Hepcidin Binding Spiegelmer In Vivo

The current concept of anemia of chronic diseases is that hepcidin synthesis and release is stimulated by pro-inflammatory cytokines, especially IL-6, in hepatocytes. Hepcidin than binds to the different cell types expressing the iron transporter ferroportin. This interaction induces an internalisation and a degradation of the hepcidin-ferroportin complex followed by a serum iron decrease. A chronic reduction of serum iron negatively impairs erythropoiesis and finally manifests in anemia. The known property of human hepcidin-25 to induce a serum iron decrease in mice (Rivera, 2005) was utilized as a model for anaemia of inflammation. To test the activity of Spiegelmers in vivo a state of hypoferremia was induced in C57BL/6 mice with human-hepcidin-25. To characterise the spiegelmers in this model, animals received a prophylactic treatment with the Spiegelmer to block the effect of hu-hepcidin.

Method

Female C57BL/6 mice (Elevage Janvier, France, six weeks old, n=6-7 per group) received a single intravenous injection of a anti-hepcidin spiegelmer (10-20 ml/kg body weight) or vehicle (5% glucose, 10-20 ml/kg body weight). After thirty minutes synthetic human hepcidin-25 (Bachem, Weil am Rhein, Germany, Cat No. H-5926) at a dose of 1-2 mg/kg body weight was injected intraperitoneally (10 ml/kg body weight). Blood was collected two hours after the hepcidin injection. Serum and plasma samples were obtained for iron determination and complete blood count, respectively. For each animal the serum iron, haemoglobin, hematocrit, white blood cell count, erythrocyte count, thrombocyte count, mean corpuscular volume, and mean corpuscular haemoglobin values were determined.

Results

Injection of synthetic human—hepcidin-25 leads to a rapid reduction of serum iron. Two hours after injection the serum iron concentration was reduced to 56 % of the value of the vehicle treated mice. These in vivo findings are in line with the data published by Rivera et al. (Ribera et al.), who reported a reduction to ca. 25% in a very similar experiment with a higher hepcidin dose. The decrease in serum iron is completely blocked (98% of control) by application of spiegelmer 223-C5-001-5'-PEG prior to injection of human hepcidin as depicted in FIG. 9. The same effect was observed with 239-D4-008-5'-PEG as depicted in FIG. 20.

EXAMPLE 7

Activity of a Hepcidin Binding Spiegelmer in Cynomomolgus Monkeys Stimulated with Human Interleukin-6

The dominant role of Interleukin-6 (IL-6) in anemia of chronic diseases was demonstrated with the IL-6 receptor antibody tocilizumab. Treatment with this antibody showed efficacy in patients with Castleman disease (Nishimoto, 2008) and also in an arthritis model in cynomolgus monkeys (Hashizume, 2009). The known property of IL-6 to induce hepcidin secretion subsequently resulting in anemia in non-human primates was utilized as another model for anaemia of inflammation (Asano, 1990; Klug 1994). Instead of the parameter haemoglobin the serum iron content was selected as endpoint to show efficacy of anti-hepcidin spiegelmers. A state of hypoferremia was induced in cynomolgus monkeys with human-recombinant IL-6. This model was important to show that anti-hepcidin spiegelmers also bind the endogenous hepcidin, as in all other experiments a synthetic human hepcidin was used. To test the activity of spiegelmers in vivo a state of hypoferremia was induced in cynomolgus monkeys with human-recombinant IL-6. To characterise the spiegelmers in this model, animals received a prophylactic treatment with the Spiegelmer to block the effect of cynomolgus-hepcidin.

Method

Male cynomolgus monkeys (Roberto C. Hartelust, Tilburg, The Netherlands) 34 to 38 months old, n=3 per group) received a single intravenous injection of a anti-hepcidin spiegelmer (1 ml/kg body weight) or vehicle (5% glucose, 1 ml/kg body weight). After thirty minutes recombinant human IL-6 (Miltenyi Biotech, Bergisth Gladbach, Germany) at a dose of 10 µg/kg body weight was injected sub cutaneously (1 ml/kg body weight). Blood was collected eight hours after the IL-6 injection. Serum and plasma samples were obtained for iron determination and complete blood count, respectively. For each animal the serum iron, haemoglobin, hematocrit, white blood cell count, erythrocyte count, thrombocyte count, mean corpuscular volume, and mean corpuscular haemoglobin values were determined.

Results

Injection of recombinant human IL-6 leads to a reduction of serum iron. Eight hours after injection the serum iron concentration was reduced to 27% of the predose value of the vehicle/IL-6 treated monkeys. The decrease in serum iron is completely blocked by application of spiegelmer 238-D4-008-5'-PEG prior to injection of human IL-6 as depicted in FIG. 21.

REFERENCES

Abboud S, Haile D J (2000) A novel mammalian iron-regulated protein involved in intracellular iron metabolism. J Biol Chem 275(26): 19906-19912

Altschul S F, Gish W, Miller W, Myers E W, Lipmann D J (1990), Basic local alignment search Tool J Mol Biol 215 (3): 403-10.

Altschul S F, Madden T L, Schaffer A A, Zhang J, Zhang Z, Miller W, Lipman D J (1997). Gapped BLAST and PSI-BLAST: a new generation of protein database search programs. Nucleic Acid Research 25(17):3389-402.

Andrews N C (2008) Forging a field: the golden age of iron biology. Blood 112(2): 219-230

Asano S, Okano A, Ozawa K, Nakahata T, Ishibashi T, Koike K, Kimura H, Tanioka Y, Shibuya A, Hirano T (1990) In vivo effects of recombinant human interleukin-6 in primates: stimulated production of platelets. Blood 75(8): 1602-1605

Constante M, Jiang W, Wang D, Raymond V A, Bilodeau M, Santos M M (2006) Distinct requirements for Hfe in basal and induced hepcidin levels in iron overload and inflammation. Am J Physiol Gastrointest Liver Physiol 291(2): G229-237

De Domenico I, Ward D M, Langelier C, Vaughn M B, Nemeth E, Sundquist W I, Ganz T, Musci G, Kaplan J (2007) The molecular mechanism of hepcidin-mediated ferroportin down-regulation. Mol Biol Cell 18(7): 2569-2578

Donovan A, Brownlie A, Zhou Y, Shepard J, Pratt S J, Moynihan J, Paw B H, Drejer A, Barut B, Zapata A, Law T C, Brugnara C, Lux S E, Pinkus G S, Pinkus J L, Kingsley P D, Palis J, Fleming M D, Andrews N C, Zon L I (2000) Positional cloning of zebrafish ferroportinl identifies a conserved vertebrate iron exporter. Nature 403(6771): 776-781

Eaton B E et (1995) Chem Biol 2:633 Eaton B E, Gold L, Hicke B J. Janjic N, Jucker F M, Sebosta D P, Tarasow T M, Willis M C, Zichi D A (1997) Bioorg Med Chem 5:1087.

Frazer D M, Wilkins S J, Millard K N, McKie A T, Vulpe C D, Anderson G J (2004) Increased hepcidin expression and hypoferraemia associated with an acute phase response are not affected by inactivation of HFE. Br J Haematol 126(3): 434-436

Hashizume M, Uchiyama Y, Horai N, Tomosugi N, Mihara M (2009) Tocilizumab, a humanized anti-interleukin-6 receptor antibody, improved anemia in monkey arthritis by suppressing IL-6-induced hepcidin production. Rheumatol Int July 29, DOI 10.1007/s00296-009-1075-4.

Hunter H N, Fulton D B, Ganz T, Vogel H J (2002) The solution structure of human hepcidin, a peptide hormone with antimicrobial activity that is involved in iron uptake and hereditary hemochromatosis. J Biol Chem 277(40): 37597-37603

Klug S, Neubert R, Stahlmann R, Thiel R, Ryffel B, Car B D, Neubert D (1994) Effects of recombinant human interleukin 6 (rhIL-6) in marmosets (Callithrix jacchus). 1. General toxicity and hematological changes. Arch Toxicol 68(10): 619-31

Klussmann, S. (eds.); The Aptamer Handbook, 1. Edition—February 2006, Wiley-VCH, Weinheim Krause A, Neitz S, Magert H J, Schulz A, Forssmann W G, Schulz-Knappe P, Adermann K (2000) LEAP-1, a novel highly disulfide-bonded human peptide, exhibits antimicrobial activity. FEBS Lett 480(2-3): 147-150

McKie A T, Marciani P, Rolfs A, Brennan K, Wehr K, Barrow D, Miret S, Bomford A, Peters T J, Farzaneh F, Hediger M A, Hentze M W, Simpson R J (2000) A novel duodenal iron-regulated transporter, IREG1, implicated in the basolateral transfer of iron to the circulation. Mol Cell 5(2): 299-309

Needleman & Wunsch (1970), A general method applicable to the search for similarities in the amino acid sequence of two proteins. J Mol Biol 48(3): 443-53.

Nemeth E, Rivera S, Gabayan V, Keller C, Taudorf S, Pedersen B K, Ganz T (2004a) IL-6 mediates hypofenemia of inflammation by inducing the synthesis of the iron regulatory hormone hepcidin. J Clin Invest 113(9): 1271-1276

Nemeth E, Turtle M S, Powelson J, Vaughn M B, Donovan A, Ward D M, Ganz T, Kaplan J (2004b) Hepcidin regulates cellular iron efflux by binding to ferroportin and inducing its internalization. Science 306(5704): 2090-2093

Nicolas G, Bennoun M, Devaux I, Beaumont C, Grandchamp B, Kahn A, Vaulont S (2001) Lack of hepcidin gene expression and severe tissue iron overload in upstream stimulatory factor 2 (USF2) knockout mice. Proc Natl Acad Sci USA 98(15): 8780-8785

Nicolas G, Bennoun M, Porteu A, Mativet S, Beaumont C, Grandchamp B, Sirito M, Sawadogo M, Kahn A, Vaulont S (2002a) Severe iron deficiency anemia in transgenic mice expressing liver hepcidin. Proc Natl Acad Sci USA 99(7): 4596-4601

Nicolas G, Chauvet C, Viatte L, Danan J L, Bigard X, Devaux I, Beaumont C, Kahn A, Vaulont S (2002b) The gene encoding the iron regulatory peptide hepcidin is regulated by anemia, hypoxia, and inflammation. J Clin Invest 110(7): 1037-1044

Nicolas G, Viatte L, Lou D Q, Bennoun M, Beaumont C, Kahn A, Andrews N C, Vaulont S (2003) Constitutive hepcidin expression prevents iron overload in a mouse model of hemochromatosis. Nat Genet 34(1): 97-101

Nishimoto N, Terao K, Mima T, Nakahara H, Takagi N, Kakehi T (2008) Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease. Blood 112(10): 3959-3964.

Park C H, Valore E V, Waring A J, Ganz T (2001) Hepcidin, a urinary antimicrobial peptide synthesized in the liver. J Biol Chem 276(11): 7806-7810

Pearson & Lipman (1988), Improved tools for biological sequence comparison. Proc Nat. AcadSci USA 85:2444.

Pigeon C, Ilyin G, Courselaud B, Leroyer P, Turlin B, Brissot P, Loreal O (2001) A new mouse liver-specific gene, encoding a protein homologous to human antimicrobial peptide hepcidin, is overexpressed during iron overload. J Biol Chem 276(11): 7811-7819

Rivera S, Nemeth E, Gabayan V, Lopez M A, Farshidi D, Ganz T (2005) Synthetic hepcidin causes rapid dose-dependent hypoferremia and is concentrated in ferroportin- containing organs. Blood 106(6): 2196-2199

Roetto A, Papanikolaou G, Politou M, Alberti F, Girelli D, Christakis J, Loukopoulos D, Camaschella C (2003) Mutant antimicrobial peptide hepcidin is associated with severe juvenile hemochromatosis. Nat Genet 33(1): 21-22

Smith & Waterman (1981), Adv. Appl.Math. 2:482

Valore E V, Ganz T (2008) Posttranslational processing of hepcidin in human hepatocytes is mediated by the prohormone convertase furin. Blood Cells Mol Dis 40(1): 132-138

Weiss G (2008) Iron metabolism in the anemia of chronic disease. Biochim Biophys Acta Weiss G, Goodnough L T (2005) Anemia of chronic disease. N Engl J Med 352(10): 1011-1023

The features of the present invention disclosed in the specification, the claims, the sequence listing and/or the drawings may both separately and in any combination thereof be material for realizing the invention in various forms thereof.

The invention claimed is:

1. A nucleic acid that binds hepcidin, comprising SEQ ID NO:148 or a homolog thereof with homology of at least 85% to SEQ ID NO:148.

2. The nucleic acid according to claim 1, wherein the nucleic acid is an antagonist of hepcidin.

3. The nucleic acid according to claim 1, wherein the nucleic acid is an inhibitor of the hepcidin-ferroportin system.

4. The nucleic acid according to claim 1, wherein the nucleic acid binds human hepcidin-25, human hepcidin-22, human hepcidin-20, monkey hepcidin-25, monkey hepcidin-22 or monkey hepcidin-20.

5. The nucleic acid according to claim 1, wherein the hepcidin has amino acid sequence of SEQ ID NO: 1.

6. The nucleic acid according to claim 1, wherein the nucleic acid comprises a modification group.

7. The nucleic acid according to claim 6, wherein the modification group is selected from the group consisting of linear poly (ethylene) glycol (PEG), branched poly (ethylene) glycol (PEG), hydroxyethyl starch (HES), a peptide, a protein, a polysaccharide, a sterol, polyoxypropylene, polyoxyamidate and poly (2-hydroxyethyl)-L-glutamine.

8. The nucleic acid according to claim 7, wherein the linear or branched PEG comprises a molecular weight of from about 20,000 to about 120,000 Da.

9. The nucleic acid according to claim 7, wherein the HES comprises a molecular weight of from about 10,000 to about 200,000 Da.

10. The nucleic acid according to claim 6, wherein the modification group is coupled to the nucleic acid by a linker.

11. The nucleic acid according to claim 1, wherein nucleotides of or nucleotides comprising the nucleic acid are L-nucleotides.

12. The nucleic acid of claim 6, wherein said modification group is a linear or a branched PEG.

13. The nucleic acid of claim 6, wherein said modification group is at a terminus of said nucleic acid.

14. The nucleic acid of claim 6, wherein said modification group is at the 5' terminus of said nucleic acid.

15. A pharmaceutical composition comprising the nucleic acid according to claim 1 and pharmaceutically acceptable excipients, pharmaceutically acceptable carriers, pharmaceutically active agents or combinations thereof.

16. A complex comprising the nucleic acid according to claim 1 and hepcidin.

17. A method for the detection of the nucleic acid according to claim 1 in a sample, wherein the method comprises the steps of:
   a) providing a sample containing the nucleic acid according to claim 1;
   b) providing a capture probe, wherein the capture probe is at least partially complementary to a first part of the nucleic acid according to claim 1, and a detection probe, wherein the detection probe is at least partially complementary to a second part of the nucleic acid according to claim 1;
   c) allowing the capture probe and the detection probe to react either simultaneously or in any order sequentially with the nucleic acid according to claim 1 to form a complex;
   d) optionally detecting whether or not the capture probe is hybridized to the nucleic acid according to claim 1 provided in step a); and
   e) detecting the complex formed in step c).

* * * * *